United States Patent [19]
Kuberasampath et al.

[11] Patent Number: 5,849,686
[45] Date of Patent: Dec. 15, 1998

[54] MORPHOGEN-INDUCED LIVER REGENERATION

[75] Inventors: Thangavel Kuberasampath, Medway; David C. Rueger, Hopkinton; Hermann Oppermann, Medway, all of Mass.; Roy H. L. Pang, Etna, N.H.; Charles M. Cohen, Medway, Mass.

[73] Assignee: Creative BioMolecules, Inc.

[21] Appl. No.: 445,468

[22] Filed: May 22, 1995

Related U.S. Application Data

[63] Continuation of Ser. No. 165,541, Dec. 9, 1993, abandoned, which is a continuation of Ser. No. 946,238, Sep. 16, 1992, abandoned, which is a continuation-in-part of Ser. No. 752,764, Aug. 30, 1991, abandoned, which is a continuation-in-part of Ser. No. 667,274, Mar. 11, 1991, abandoned, said Ser. No. 946,238, Sep. 16, 1992, abandoned, is a continuation-in-part of Ser. No. 938,336, Aug. 28, 1992, abandoned, and Ser. No. 938,337, Aug. 28, 1992, abandoned, each is a continuation-in-part of Ser. No.753,059, Aug. 30, 1991, abandoned, which is a continuation-in-part of Ser. No. 667,274.

[51] Int. Cl.⁶ .......................... A61K 38/18; A61K 38/17; C07K 14/51
[52] U.S. Cl. ..................... 514/2; 514/8; 514/12; 435/69.1; 435/172.3
[58] Field of Search ................... 514/2, 8, 12; 435/69.1, 435/172.3

[56] References Cited

U.S. PATENT DOCUMENTS

| | | | |
|---|---|---|---|
| 4,309,412 | 1/1982 | Ishikawa et al. | 424/78.37 |
| 4,396,601 | 8/1983 | Salzer et al. | 424/94.5 |
| 4,775,675 | 10/1988 | Gyorqydeak et al. | 514/307 |
| 4,868,116 | 9/1989 | Morgan et al. | 435/240.2 |
| 4,870,009 | 9/1989 | Evans et al. | 435/69.4 |
| 4,877,864 | 10/1989 | Wang et al. | 514/12 |
| 4,968,590 | 11/1990 | Kuberasampath et al. | 530/326 |
| 4,975,526 | 12/1990 | Kuberasampath et al. | 530/350 |
| 4,980,286 | 12/1990 | Morgan et al. | 435/172.3 |
| 4,983,581 | 1/1991 | Antoniades et al. | 514/12 |
| 5,002,965 | 3/1991 | Ramwell et al. | 424/423 |
| 5,011,691 | 4/1991 | Oppermann et al. | 424/423 |
| 5,013,649 | 5/1991 | Wang et al. | 435/69.1 |
| 5,061,620 | 10/1991 | Tsukamoto et al. | 435/7.21 |
| 5,075,229 | 12/1991 | Hanson et al. | 435/172.3 |
| 5,106,626 | 4/1992 | Parsons et al. | 424/423 |
| 5,108,753 | 4/1992 | Kuberasampath et al. | 424/422 |
| 5,108,989 | 4/1992 | Amento et al. | 514/12 |
| 5,141,905 | 8/1992 | Rosen et al. | 435/69.1 |

FOREIGN PATENT DOCUMENTS

| | | |
|---|---|---|
| 0148155 | 7/1985 | European Pat. Off. |
| 0416578 | 3/1991 | European Pat. Off. |
| 88/00205 | 1/1988 | WIPO |
| 88/03785 | 6/1988 | WIPO |
| 89/09787 | 10/1989 | WIPO |
| 89/09788 | 10/1989 | WIPO |
| 89/10409 | 11/1989 | WIPO |
| 90/03733 | 4/1990 | WIPO |
| 90/10018 | 9/1990 | WIPO |
| 90/12603 | 11/1990 | WIPO |
| 90/12604 | 11/1990 | WIPO |
| 91/18558 | 12/1991 | WIPO |

OTHER PUBLICATIONS

Bowie et al. 1990. Science 247:1306–1310.
Massagué (1987) Cell, vol. 49, pp. 437–438.
Pepinsky et al. (1988) Journal of Biological Chemistry, vol. 263, pp. 18961–18964.
Lefer et al. (1990) Science 249:61–64.
Sporn et al. (1989) Journal of the American Medical Association, vol. 262, pp. 938–941.
Wahl et al. (1989) Immunology Today, vol. 10, pp. 258–261.
Anderson, *Science*, 226:401–409 (1984).
Anderson, *Science*, 256:808–813 (1992).
Behringer et al., *Nature*, 345:167–170 (1990).
Cate et al., *Cell*, 45:685–698 (1986).
Celeste et al., *PNAS*, 87:9843–9847 (1990).
Cone et al., *PNAS*, 81:6349–6353 (1984).
Dichek et al., *Trans. Ass. Am. Physicians,* 103:73–79 (1990).
Fausto et al., *Clinical Applications of TGF–β,* Wiley, Chichester, 165–177 (1991).
Green et al., *Nature,* 347:391–394 (1990).
Karson, *J. Reprod. Med.*, 37:508–514 (1992).
Lee, *Molecular Endocrinology,* 4:1034–1040 (1990).
Lee, *PNAS,* 88:4250–4254 (1991).
Lyons et al., *PNAS,* 86:4554–4558 (1989).
Lyons et al., *Genes & Development,* 3:1657–1668 (1989).
Mason et al., *Nature,* 318:659–663 (1985).
Mason et al., *Mol. Endocrinology,* 3:1352–1358 (1989).
Mercola et al., *New Engl. Journ. Med.,* 303:(22) 1297–1300 (1980).
Miller et al., *Cancer Research,* 42:3589–3594 (1987).
Ozkaynak et al., *Embo J.,* 9:2085–2093 (1990).
Ozkaynak et al., *Biochem, Biophys. Res. Comm.,* 179:116–123 (1991).
Padgett et al., *Nature,* 325:81–84 (1987).
Panganiban et al., *Mol. and Cell. Biol.,* 10:2669–2677 (1990).
Sampath et al., *J. Biol. Chem,* 265:13198–13205 (1990).
Sampath et al., *PNAS,* 80:6591–6595 (1983).
Schubert et al., *Nature,* 344:868–870 (1990).
Smith et al., *Nature,* 345:729–731 (1990).
Sokol et al., *Science,* 249:561–564 (1990).
Van Thiel et al. *Gastro. Clinics N. America,* 17:1–18 (1988).
Wang et al., *PNAS,* 87:2220–2224 (1990).
Wang et al., *PNAS,* 85:9484–9488 (1988).

(List continued on next page.)

*Primary Examiner*—Vasu S. Jagannathan
*Assistant Examiner*—Elizabeth C. Kemmerer
*Attorney, Agent, or Firm*—Testa, Hurwitz & Thibeault,LLP

[57] ABSTRACT

Disclosed are therapeutic treatment methods, compositions and devices for maintaining liver function in a mammal, including methods, compositions and devices for regenerating lost or damaged hepatic tisse, enhancing viability and integration of hepatic tissue and organ transplants, and correcting liver function deficiencies. The methods, compositions and devices on this invention all provide a therapeutically effective morphogen concentration to the hepatic cells to be treated.

19 Claims, 6 Drawing Sheets

OTHER PUBLICATIONS

Weeks, *Cell*, 51:861–867 (1987).
Wharton et al., *PNAS*, 88:9214–9218 (1991).
Wozney et al., *Science*, 242:1528–1533 (1988).
Yannas, *Angew. Chem. Int. Ed. Engl.*, 29:20–35 (1990).
Rosen et al.; Wang et al. and Wozney et al., *Calcified Tissue Int* 42 (Suppl.): A35(136), A37(146,147) 3 Abstracts (1988).
Rosen et al., *Connect Tissue Res*, 20 (1–4):313–9 (1999).
Wozney et al., *Progress In Growth Factor Research*, 1:267–280 (1990).
2 Abstracts Rosen et al., Celeste et al., *J Cell Biochem Suppl.*, 0 (14 Part E): 33(004, 54(105) (1990).
Katagiri et al., *Biochem Biopys Res*, (172(1):295–299 (1990).
Wozney et al., *Journal Of Cell Science Suppl.*, 13:149–156 (1990).

Takuwa et al., *Biochem Biophys Res Comm*, 174(1):96–101 (1991).
Yamaguchi et al., *J Cell Biol*, 113 (3):681–7 (1991).
Abstract Q–105 D'Alessandro et al., *Journal Of Cellular Biochemistry*, (1991).
Abstract Q–111, *Journal Of Cellular Biochemistry*, (1991).
Thies et al., *Endocrinology*, 130 (3):1318–1324 (1992).
Wozney et al., *Mol Reprod Dev*, 32 (2):160–167 (1992).
Rogers et al., *Mol Biol Cell*, 3 (2):189–196 (1992).
3 Abstracts Wozney et al.; Celeste et al.; and Rosen et al., *J Cell Biochem Suppl*, 0 (16 Part F): 76(WO26); 100(W502); 103(W513) (1996).
Israel et al., *Growth Factors*, 7:139–150 (1992).
Padgett et al., *Proc. Natl. Acad. Sci. USA*, 90:2905–2909 (1993).

MORPHOGEN-INDUCED LIVER REGENERATION

CROSS REFERENCE TO RELATED APPLICATIONS

This is a continuation of U.S. Ser.No. 08/165,541, filed Dec. 9, 1993 (now abandoned) which is a continuation of U.S. Ser. No. 07/946,238, filed on Sep. 16, 1992 (now abandoned). Prior U.S. Ser.No. 07/946,238 was a continuation-in-part of (1) U.S. Ser .No. 07/752,764, filed Aug. 30, 1991 (now abandoned), which was a continuation-in-part of U.S. Ser.No. 07/667,274, filed Mar. 11, 1991 (now abandoned); (2) U.S. Ser. No. 07/938,336, filed Aug. 28, 1992 (now abandoned) and (3) U.S. Ser. No. 07/938,337, filed Aug. 28, 1992 (now abandoned). U.S. Ser. No. 07/937, 337 was a continuation-in-part of U.S. Ser. No. 07/753,059, filed Aug. 30, 1991, (now abandoned), which was a continuation-in-part of abandoned U.S. Ser. No. 07/667,274, filed Mar. 11, 1991 (now abandoned) Ths disclosures of each of the aforementioned applications are incorporated herein by reference.

FIELD OF THE INVENTION

The present invention relates generally to liver treatment methods.

BACKGROUND OF THE INVENTION

The present invention relates to methods and compositions for regenerating lost or damaged liver tissue in vivo and to methods and compositions for maintaining normal liver function which may be reduced or lost as a result of such tissue damage. The invention further relates to methods and compositions for correcting one or more liver function deficiencies in a mammal, particularly a human.

The liver is the largest visceral organ in the body and consists of two main lobes, a larger right lobe and a smaller left lobe. The right lobe also contains two smaller segments referred to as the cuadata and quadrata lobes. The liver has a dual blood supply, consisting of the hepatic artery and the portal vein. The hepatic lymphatics drain principally into lymph nodes of the porta hepatis and celiac axis.

The liver is responsible for a wide variety of functions, broadly characterized as metabolic, storage, synthetic, catabolic and excretory. Specifically, the liver is the central organ of glucose homeostasis, responsible for both storing excess blood glucose as glycogen and restoring blood glucose by glycogenolysis and gluconeogenesis and by converting free fatty acids to triglycerides and lipoproteins. The liver also stores triglycerides, iron, copper and lipid-soluble vitamins and synthesizes many of the binding proteins for iron, copper and Vitamin A.

In addition, most serum proteins, with the exception of immunoglobulins, are synthesized in the liver, including albumin, the principal source of plasma osmotic pressure, blood clotting factors such as prothrombin, fibrinogen and Factor VIII, as well as complement and other acute phase reactants involved in an immune response. The liver also functions as a catabolic site for hormones, serum proteins, and other endogenous proteins, as well as acting as the detoxification site for foreign compounds, including drugs (pharmaceuticals), industrial chemicals, environmental contaminants, and various bacterial metabolism byproducts. Finally, the liver excretes bile, which provides a repository for the products of hemecatabolism and also is vital for fat absorption in the small intestine.

Not surprisingly, liver function disorders, whether resulting from a particular protein deficiency or from hepatic tissue damage and/or loss, has serious and far-reaching consequences. For example, reduced albumin levels in chronic liver disease contribute to the development of edema and ascites; liver failure also is characterized by severe and often life-threatening bleeding, due to the reduced production of essential blood clotting factors. Hepatic failure also can induce neurological dysfunction, characterized broadly as hepatic encephalopathy, as well as associated renal failure, jaundice, pulmonary complications, and a host of disorders associated with hormonal imbalances.

Unlike most other organs in the body the liver has a defined regenerative capacity following hepatic tissue damage or cell death. Specifically, while hepatocytes do not proliferate actively following fetal and post natal liver growth, normally quiescent hepatocytes do divide in response to cell death or loss of liver tissue. However, where tissue damage is extensive and/or chronic, permanent tissue damage can result, reducing the organ's viability and functional capacity. Permanent hepatic tissue damage typically is characterized by extensive necrosis and/or fibrogenesis or scarring (cirrhosis). Another source of nonreparative damage results from hepatic neoplasms and metastatic carcinomas.

Where either the mass of liver cells is sufficiently diminished or their function sufficiently impaired, hepatic failure ensues. The etiology of hepatic failure may be metabolic (e.g., altered bilirubin metabolism or fatty acid storage), infectious (e.g., induced by viral hepatitis, hepatic schistomiasis, syphilis, or ascariaris), toxic (e.g., induced by ethanol, ammonia, phenol, and other environmental toxins, fatty acids, drugs and/or their metabolites), autoimmune, ischemic or nutritional (e.g., alcoholic liver disease).

Another source of hepatic failure results from malignant tumors. The tumor cells may be derived from hepatic tissue cells (as in hepatocellular carcinoma, bileduct carcinomas, hepatoblastomas or hemangiosarcoma) or may be derived from distant tissue as part of a metastatic cancer. In fact, metastatic cancers are by far the most common malignant neoplasms of the liver, most notably derived from cancers of the gastrointestinal tract, breast and lung.

Another source of diminished liver function arises from hepatic protein deficiencies, which may result from a genetic defect (so called "inborn errors of metabolism") or may be induced by, for example, a pharmaceutical, infectious agent byproduct, or the like. For example, hemophilia is believed to be associated with diminished Factor VIII production. Similarly, Wilson's disease, a copper metabolism disorder, is associated with deficient ceruloplasmin production by the liver. Altered production of albumin in the liver affects bilirubin metabolism. Deficiency of $\alpha_1$-antitrypsin, also normally produced in the liver, can result in fatal neonatal hepatitis.

To date, the only viable treatment for hepatic failure or for patients at risk for hepatic failure due to, for example, chronic acute hepatitis, biliary atresia, idiopathic cirrhosis, primary biliary cirrhosis, sclerosing cholangitis, inborn errors of metabolism or malignancy, is liver transplantation. To date, liver transplantation also is the only viable alternative for correcting significant liver function deficiencies that result from inborn errors of metabolism. Liver transplantation as a treatment method suffers from donor scarcity, particularly of pediatric livers, technical surgical complexity, postoperative complications including organ rejection, and continuing difficulties in maintaining organ viability throughout the transplant process.

Selective cell transplantation of only those parenchymal elements necessary to replace lost function has been proposed as an alternative to whole or partial organ transplantation that avoid major surgery with its attendant blood loss, anesthetic difficulties, and complications (P. S.Russell, *Ann. Surg.* 201(3), 255–262 (1985). Replacing only those cells which supply the needed function reduces problems with passenger leukocytes, antigen presenting cells, and other cell types which may promote the rejection process. The ability to expand cell numbers with proliferation of cells in culture, in theory, allows autotransplantation of one's own tissue. In addition, transplantable cells may be used as part of a gene therapy to correct a liver protein deficiency, and/or as in vivo drug delivery vehicles. WO88/03785 published Jun. 2, 1988, and WO90/12640 published Nov. 1, 1990, both describe methods for attaching hepatocytes to matrices and implanting the matrices at sites in vivo that are capable of providing the cells with adequate nutrition or gas exchange, such as within mesentery folds or the odentum. To date, the existing protocols suffer from a variety of limitations. Typically, partial hepatectomy is required to stimulate cell proliferation of the synthetic tissue in vivo. In addition, cell implantation typically is accompanied by significant cell loss, requiring a substantial seed cell population for implantation, which may further require lengthy in vitro incubation periods. The delay in in vivo integration of the implanted cell-matrix structure also places significant restrictions on the matrix scaffold composition. Finally, the implanted cell-matrix structures also are at risk for destruction by the implant host's immune response mechanisms.

It is an object of this invention to provide methods and compositions for regenerating lost or damaged hepatic tissue in vivo in an existing liver without requiring organ or tissue transplant. Another object is to provide means for maintaining normal liver function following hepatic tissue injury or in anticipation of such injury. Another object is to provide means for enhancing or increasing a depressed liver function level which may result from a tissue injury or disease. Still another object is to provide methods and compositions for correcting a liver function deficiency in a mammal. Yet another object is to provide gene therapy protocols and compositions useful for correcting a protein deficiency in a mammal. Yet another object is to enhance integration of a liver tissue implant. These and other objects and features of the invention will be apparent from the description, drawings and claims which follow.

SUMMARY OF THE INVENTION

The present invention provides methods and compositions for maintaining liver function in a mammal. The invention provides means for correcting one or more liver function deficiencies in a mammal that may arise, for example, from an inborn metabolism defect, and means for regenerating lost or damaged hepatic tissue in a mammal, including means for protecting the tissue from damage thereto. The invention also provides means for enhancing the viability of a hepatic tissue or organ to be transplanted and means for enhancing the integration of the transplanted tissue. The methods and compositions of this invention include providing to hepatic cells a therapeutically effective concentration of a morphogenic protein ("morphogen", as defined herein) upon hepatocellular injury, or in anticipation of such injury, or following diagnosis of a liver function defect in a mammal, for a time and at a concentration sufficient to maintain or regain liver function in vivo.

In one aspect, the invention features compositions and therapeutic treatment methods that include administering to a mammal a therapeutically effective amount of a morphogenic protein ("morphogen"), as defined herein, upon hepatocellular injury, or in anticipation of such injury, or following diagnosis of a liver function deficiency, for a time and at a concentration sufficient to maintain normal and/or to regain lost liver function in vivo, including regenerating lost or damaged hepatic tissue, and/or inhibiting additional damage thereto. The morphogens described herein also are capable of enhancing the level of a liver function which may be depressed as a result of a tissue injury or disease.

In another aspect, the invention features compositions and therapeutic treatment methods for maintaining liver function in a mammal in vivo which include administering to the mammal, upon hepatocellular injury or in anticipation of such injury, or following diagnosis of a liver function deficiency, a compound that stimulates in vivo a therapeutically effective concentration of an endogenous morphogen within the body of the mammal sufficient to increase or enhance the level of a depressed liver function, and/or to maintain normal and/or regain lost liver function, including regenerating damaged or lost hepatic tissue and/or inhibiting additional damage thereto. These compounds are referred to herein as morphogen-stimulating agents, and are understood to include substances which, when administered to a mammal, act on cells of tissue(s) or organ(s) that normally are responsible for, or capable of, producing a morphogen and/or secreting a morphogen, and which cause the endogenous level of the morphogen to be altered. The agent may act, for example, by stimulating expression and/or secretion of an endogenous morphogen.

While the methods and compositions described herein are particularly related to liver organ therapies, as will be appreciated by those skilled in the art, and as described in the now abaondoned parents of the instant application, including U.S.Ser. No. 667,274, U.S. Ser. No. 752,764, U.S. Ser. No. 753,059, U.S. Ser. No. 07/938,336 and U.S. Ser. No. 07/938,337, the methods and compositions of this invention can be applied, without undue experimentation, to other organ applications, including but not limited to, the pancreas, lung, kidney and heart. Accordingly, the methods and compositions disclosed herein can be used to advantage in the repair, regeneration, transplantation and/or function level enhancement of damaged or lost tissue such as, for example, damaged lung tissue resulting from emphysema, cirrhotic kidney or pancreatic tissue, damaged heart or blood vessel tissue, as may result from cardiomyopathies and/or atherothrombotic or cardioembolic strokes, damaged stomach tissue resulting from ulceric perforations or their repair, damaged neural tissue as may result from physical injury, degenerative diseases such as Alzheimer's disease or multiple sclerosis or strokes, and damaged dental and/or periodental tissue as may result from disease or mechanical injury. The methods and compositions also may be used to protect these tissues from anticipated injury, including unavoidably or deliberately induced injury, as may occur in a surgical or other clinical procedure. In addition to the tissue regenerative properties provided herein, the gene therapy and drug delivery protocols described herein may be used to particular advantage in pancreatic tissue, renal tissue and lung tissue contexts.

As embodied herein, the expression "maintaining normal liver function" means both regaining or restoring liver function lost due to a hepatocellular injury or inborn metabolic defect, as well as protecting the hepatic tissue at risk of damage from hepatocellular injury. "Depressed liver function" level refers to a diminished or deficient liver function as a result of a tissue injury or disease. The expression "enhance viability of" transplant hepatic tissue or organ, as used herein, means protection from, reduction of and/or elimination of reduced or lost tissue or organ function as a result of tissue necrosis and/or fibrosis associated with transplantation, particularly immune response-mediated tissue necrosis and/or fibrosis. "Alleviating" means protection from, reduction of and/or elimination of undesired tissue destruction, particularly immune response-mediated tissue destruction. "Transplanted" living tissue includes both tissue grafts and cellular transplants, as in the case of transplanted isolated progenitor or stem cells, for example, which may be implanted alone or in association with a temporary scaffolding. Tissues may be autologous or allogenic tissue and/or synthetic tissue created, for example, by culturing hepatic cells in the presence of an artificial matrix. "Morphogenically permissive environment" is understood to mean an environment competent to allow tissue morphogenesis to occur. Finally, "symptom alleviating cofactor" refers to one or more pharmaceuticals which may be administered together with the therapeutic agents of this invention and which alleviate or mitigate one or more of the symptoms typically associated with liver tissue and/or liver function loss. Exemplary cofactors include antibiotics, antiseptics, non-steroidal anti-inflammatory agents, and the like.

In one aspect of the invention, the methods and compositions of this invention are useful in the replacement of diseased, damaged or lost hepatic tissue in a mammal, particularly when the damaged tissue interferes with normal tissue or organ function. Where hepatic tissue has been lost, remaining hepatocytes are capable only of compensatory cell division to return the organ volume essentially to its original size. As determined by extensive experimental partial hepatectomy studies wherein part of all of a liver lobe is excised, this compensatory growth does not involve true morphogenisis, and the lost tissue is not itself regenerated. Rather, the intact lobe is capable only of tissue augmentation to compensate for the lost mass. By contrast, recent studies on toxin-induced tissue damage does suggest that this repair involves morphogenesis, particularly the infiltration and proliferation of progenitor cells. As described in Example 3 and 4, below, endogenous morphogen expression is enhanced following toxin-induced hepatic tissue damage, and not following partial hepatectomy.

When the proteins described herein are provided to, or their expression stimulated at, a hepatic tissue locus, the developmental cascade of tissue morphogenesis is induced, capable of stimulating the migration, proliferation and differentiation of hepatic progenitor cells, to regenerate viable hepatic tissue, including inducing the necessary associated vascularization (see below). Thus, in one embodiment the invention provides methods and compositions for regenerating lost or substantially irreparably damaged hepatic tissue. The morphogen preferably is provided directly to the locus of tissue regeneration, e.g., by injection of the morphogen dispersed in a biocompatible, injectable solution, or by topical administration, as by painting or spraying a morphogen-containing solution on the tissue. Preferably, the locus has been surgically prepared by removing existing necrotic or cirrhotic tissue. Alternatively, morphogen may be provided locally by means of an osmotic pump implanted in the peritoneal cavity. At least one morphogen (OP-1, comprising e.g. Seq. ID No. 5) is known to be expressed by hepatic tissue during liver formation. Accordingly, in the alternative, and/or in addition, an agent capable of stimulating expression and/or secretion of an endogenous morphogen may be administered. As yet another alternative, progenitor hepatocytic cells may be stimulated ex vivo by exposure to a morphogen or morphogen-stimulating agent, and the stimulated cells, now primed for proliferation and differentiation, then provided to the hepatic tissue locus. A morphogen or a morphogen-stimulating agent also may be implanted with the cells. Alternatively, a suitable local morphogen concentration may be maintained by means of, for example, an osmotic pump. In all these cases the existing tissue provides the necessary matrix requirements, providing a suitable substratum for the proliferating and differentiating cells in a morphogenically permissive environment, as well as providing the necessary signals for directing the tissue-specificity of the developing tissue.

When the morphogens (or progenitor cells stimulated by these morphogens) are provided at a tissue-specific locus (e.g., by systemic injection or by implantation or injection at a tissue-specific locus, or by administration of an agent capable of stimulating morphogen expression in vivo), the existing tissue at that locus, whether diseased or damaged, has the capacity of acting as a suitable matrix. Alternatively, a formulated matrix may be externally provided together with the stimulated progenitor cells or morphogen, as may be necessary when the extent of injury sustained by the damaged tissue is large. The matrix should be a biocompatible, suitably modified acellular matrix having dimensions such that it allows the influx, differentiation, and proliferation of migratory progenitor cells, and is capable of providing a morphogenically permissive environment (see infra). Currently preferred matrices also are biodegradable. Where morphogen and/or progenitor cells are to be implanted and the existing liver tissue is insufficient to provide the necessary matrix components, the formulated matrix preferably is tissue-specific.

Formulated matrices may be generated from a fibrin clot or dehydrated organ-specific tissue, prepared for example, by treating the tissue with solvents to substantially remove the non-structural components from the tissue. Alternatively, the matrix may be formulated synthetically using one or more biocompatible, preferably in vivo biodegradable, structural carrier materials such as collagen, laminin, and/or hyaluronic acid which also may be in association with suitable tissue-specific cell attachment factors. Other biocompatible, in vivo biodegradable components, including synthetic polymers, including polybutyric, polylactic, polyglycolic acids, polyanhydrides and/or copolymers thereof. Currently preferred structural materials contain collagens. Currently preferred cell attachment factors include glycosaminoglycans and proteoglycans. The matrix further may be treated with an agent or agents to increase the number of pores and/or micropits on its surfaces, so as to enhance the influx, proliferation and differentiation of migratory progenitor cells from the body of the mammal.

In many instances, the loss of hepatic tissue function results from fibrosis or scar tissue formation, formed in response to an initial or repeated injury to the tissue. The degree of scar tissue formation generally depends on the regenerative properties of the injured tissue, and on the degree and type of injury. In liver, repeated tissue damage results in liver cirrhosis which destroys normal hepatic architecture by fiberous septa, causing vascular disorganization and perfusion deficits that impair liver function and unchecked, lead to hepatic failure. Thus, in another aspect, the invention provides methods and compositions that may be used to prevent and/or substantially inhibit the formation of scar tissue in hepatic tissue by providing the morphogens, or morphogen-stimulated cells, to a newly injured tissue locus (see below).

The morphogens of this invention also may be used to increase or regenerate a liver progenitor or stem cell population in a mammal. For example, progenitor cells may be isolated from an individual's bone marrow, stimulated ex vivo for a time and at a morphogen concentration sufficient to induce the cells to proliferate, and returned to the bone marrow. Other sources of progenitor cells that may be suitable include biocompatible cells obtained from a cultured cell line, stimulated in culture, and subsequently provided to the body. Alternatively, the morphogen may be provided systemically, or implanted, injected or otherwise provided to a progenitor cell population in an individual to induce its mitogenic activity in vivo. For example, an agent capable of stimulating morphogen expression in the progenitor cell population of interest may be provided to the cells in vivo, for example systemically, to induce mitogenic activity.

In still another aspect of the invention, the morphogens also may be used to support the growth and maintenance of differentiated cells, inducing existing differentiated cells to continue expressing their phenotype. It is anticipated that this activity will be particularly useful in the treatment of liver disorders where loss of liver function is caused by cells becoming metabolically senescent or quiescent. Application of the protein directly to the cells to be treated, or providing it by systemic injection, can be used to stimulate these cells to continue expressing their phenotype, thereby significantly reversing the effects of the dysfunction. Alternatively, administration of an agent capable of stimulating morphogen expression in vivo also may be used. In addition, the morphogens of this invention also may be used in gene therapy protocols to stimulate the growth of quiescent cells, thereby potentially enhancing the ability of these cells to incorporate exogenous DNA.

In another aspect of the invention, the method disclosed is useful for redifferentiating transformed cells, particularly transformed cells of parenchymal origin, such that the morphogen-treated cells are induced to display a morphology characteristic of untransformed cells. As specifications of now-abandoned parent applications described in the U.S. Ser. No 752,764 and USSN 922,813, filed Aug. 28, 1992 and incorporated herein by reference, the morphogens previously have been found to induce redifferentiation of transformed embryonic cells and cells of neuronal origin to a morphology characteristic of untransformed cells. Morphogen treatment preferably induces cell rounding and cell aggregation (clumping), cell-cell adhesion, and CAM production. The methods described herein are anticipated to substantially inhibit or reduce hepatocytic cell tumor formation and/or proliferation in liver tissue. It is anticipated that the methods of this invention will be useful in substantially reducing the effects of various carcinomas and sarcomas of liver tissue origin, including hepatocellular carcinomas, bileduct carcinomas, hepatoblastomas, and hemangiosarcomas. In addition, the method also is anticipated to aid in inhibiting neoplastic lesions caused by metastatic tissue. Metastatic tumors are one of the most common neoplasms of the liver, as they can reaching the liver through the bloodstream or lymph nodes. Metastatic tumors may damage hepatic function for example, by distorting normal liver tissue architecture, blocking or inhibiting blood flow, and/or by stimulating the body's immune response.

In another aspect of the invention, the morphogens described herein are useful for providing hepatocellular protective effects to alleviate liver tissue damage associated with the body's immune/inflammatory response to an initial injury to the tissue. As described in detail in abandoned parent applications U.S. Ser. No. 07/753,059, U.S. Ser. No. 07/938,336 and 07/938,337 such a response may follow acute or chronic trauma to hepatic tissue, caused, for example, by an autoimmune dysfunction, neoplastic lesion, infection, chemical or mechanical trauma, disease or by partial or complete interruption of blood flow to hepatocytes, for example following ischemia or hypoxia, or by other trauma to the liver or surrounding material. For example, portal hypertension is a significant liver disease caused by reduced blood flow through the portal vein and is characterized by tissue necrosis and cirrhosis. Application of the morphogen directly to the cells to be treated, or providing the morphogen to the mammal systemically, for example, intravenously or indirectly by oral administration, may be used to alleviate and/or inhibit the immunologically related response to a hepatic tissue injury. Alternatively, administration of an agent capable of stimulating morphogen expression and/or secretion in vivo, preferably at the site of injury, also may be used. Where the injury is to be unavoidably or deliberately induced, as during surgery or other aggressive clinical treatment, the morphogen or agent may be provided prior to induction of the injury to provide a cytoprotective effect to the liver tissue at risk.

Similarly, hepatic tissues and organs for transplantation also are subject to the tissue destructive effects associated with the recipient host body's inflammatory response following transplantation. It is currently believed that the initial destructive response is due in large part to reperfusion injury to the transplanted organ after it has been transplanted to the organ recipient.

Accordingly, the success of liver or hepatic tissue transplantation depends greatly on the preservation of the tissue activity (e.g., tissue or organ viability) at the harvest of the organ, during storage of the harvested organ, and at transplantation. To date, preservation of organs such as lungs, pancreas, heart and liver remains a significant stumbling block to the successful transplantation of these organs. U.S. Pat. No. 4,952,409 describes a superoxide dismutase-containing liposome to inhibit reperfusion injury. U.S. Pat. No. 5,002,965 describes the use of ginkolides, known platelet activating factor antagonists, to inhibit reperfusion injury. Both of these factors are described as working primarily by inhibiting the release of and/or inhibiting the damaging effects of free oxygen radicals. A number of patents also have issued on the use of immunosuppressants for inhibiting graft rejection. A representative listing includes U.S. Pat. Nos. 5,104,858, 5,008,246 and 5,068,323. A significant problem with many immunosuppressants is their low therapeutic index, requiring the administration of high doses that can have significant toxic side effects.

Thus, in another aspect of the invention, where a partial or complete organ transplant is desired, the morphogen may be administered to transplant tissue to enhance the viability of the tissue, to alleviate the tissue damage associated with immune response-mediated tissue destruction and/or to provide a cytoprotective effect to tissue at risk for such damage. Exemplary transplant tissues include hepatic tissue grafts which may be allogenic, autologous and/or synthetic (e.g., cultured cells attached to an artificial matrix), and whole or partial livers. Where the transplant tissue (e.g., liver, lung, kidney, pancreas, heart, etc.) is to be harvested from a donor host, the morphogen also preferably is provided to the tissue prior to, or concomitant with the tissue harvest, e.g., as a prophylactic, to provide a cytoprotective effect to the tissue.

In another aspect of the invention, the morphogens described herein also may be used in a gene therapy protocol and/or as part of a drug delivery protocol to correct a protein deficiency in a mammal, resulting, for example, from a genetic disorder or other dysfunction to the protein-producing tissue. Specifically, the methods and compositions of this invention are contemplated for use in providing to the mammal an in vivo protein-producing mechanism for correcting any protein deficiency in the mammal. These proteins include proteins normally expressed and/or secreted by hepatic tissue and which play a role in liver-related functions, proteins normally expressed and secreted by the liver and which function elsewhere in the body, and proteins not normally expressed by hepatic tissue. Cells competent for expressing one or more proteins necessary to overcome the protein deficiency in vivo may be stimulated to proliferate ex vivo, and then implanted at a morphogenically permissive site at a liver-specific tissue locus in vivo. The competent cells may be attached to a scaffold-like structure prior to implantation. Alternatively, the competent cells may be attached to a synthetic or formulated matrix and implanted together with a morphogen at an extra-hepatic site in vivo, such as within the folds of the mesentery, or other associated vascularized tissue locus capable of providing the necessary nutrients and gas exchange to the cells. A detailed description of useful extra-hepatic loci are described, for example, in WO90/12604, published Nov. 1, 1990 to Vacanti et al., the disclosure of which is incorporated herein by reference. Exposing primary hepatocytes to a morphogen stimulates their proliferation (see below), thereby enhancing their cellular viability upon implantation, accelerating tissue development, and reducing the original cell population required to seed the matrix. In addition, implantation with a morphogen eliminates the need for partial hepatectomy to stimulate proliferation, and enhances cellular viability by inhibiting the inflammatory/immune response typically associated with such a procedure, overcoming the significant hepatocyte cell loss typically seen in this procedure.

Cells competent for correcting a protein deficiency include allogenic primary hepatocytes, preferably from a serotypically compatible individual and competent for expressing the protein or proteins of interest, and autologous cells transfected with the genetic material necessary to express the protein of interest. For example, primary hepatocytes may be removed from the patient by biopsy, transfected using standard recombinant DNA technology, proliferated, attached to a matrix and reimplanted together with a morphogen. Preferably the morphogen is provided to the cells during transfection and proliferation to enhance the mitogenic activity (and nucleic acid uptake) of these cells. In a currently preferred embodiment, morphogen is adsorbed to the matrix surface to which the cells are attached and the complex implanted as a single entity ("cell-matrix structure".)

In any treatment method of the invention, "administration of morphogen" refers to the administration of the morphogen, either alone or in combination with other molecules. For example, the mature form of the morphogen may be provided in association with its precursor "pro" domain, which is known to enhance the solubility of the protein. Alternatively, the pro form of the morphogen (e.g., defined, for example, by amino acid residues 30–431 of OP1, Seq. I.D. No. 16, see below) may be used. Other useful molecules known to enhance protein solubility include casein and other milk components, as well as various serum proteins. Additional useful molecules which may be associated with the morphogen or morphogen-stimulating agent include tissue targeting molecules capable of directing the morphogen or morphogen-stimulating agent to hepatic tissue. Tissue targeting molecules envisioned to be useful in the treatment protocols of this invention include antibodies, antibody fragments or other binding proteins which interact specifically with surface molecules on nerve tissue cells. Still another useful tissue targeting molecule may include part or all of the morphogen precursor "pro" domain.

Associated tissue targeting or solubility-enhancing molecules also may be covalently linked to the morphogen using standard chemical means, including acid-labile linkages, which likely will be preferentially cleaved in the acidic environment of bone remodeling sites.

The morphogens and morphogen-stimulating agents also may be provided to the liver tissue together with other molecules ("cofactors") known to have a beneficial effect in treating damaged hepatic tissue, particularly cofactors capable of mitigating or alleviating symptoms typically associated with hepatic tissue damage and/or loss. Examples of such cofactors include antiseptics, antibiotics, tetracycline, aminoglycosides, macrolides, penicillins and cephalosporins, and other, non-steroidal anti-inflammatory agents.

Among the morphogens useful in this invention are proteins originally identified as osteogenic proteins, such as the OP-1 (comprising, e.g., the sequence shown in Seq. ID No. 5 or 6), OP-2 (comprising, e.g., the sequence shown in Seq. ID No. 7 or 8) and CBMP2 (comprising, e.g., the sequence shown in Seq. ID No. 9 or 10) proteins, as well as amino acid sequence-related proteins such as DPP (from Drosophila; comprising, e.g., the sequence shown in Seq. ID No. 11, Vgl (from Xenopus; comprising, e.g., the sequence shown in Seq. ID No. 12), Vgr-1 (from mouse; comprising, e.g., the sequence shown in Seq. ID No. 13, see U.S. Pat. No. 5,011,691 to Oppermann et al.), GDF-1 (from mouse; comprising, e.g., the sequence shown in Seq. ID No. 14, see Lee (1991) PNAS 88:4250–4254), all of which are presented in Table), and the recently identified 60A protein (from Drosophila comprising, e.g., the sequence shown in, Seq. ID No. 24, see Wharton et al. (1991) PNAS 88:9214–9218). The members of this family, which include members of the TGF-β super-family of proteins, share substantial amino acid sequence homology in their C-terminal regions. The proteins are translated as a precursor, having an N-terminal signal peptide sequence, typically less than about 30 residues, followed by a "pro" domain that is cleaved to yield the mature sequence. The "pro" form of the protein, includes both the pro domain and the mature domain, and forms a soluble species that apprears to be the primary form secreted from cultured mammalian cells. The signal peptide is cleaved rapidly upon translation, at a cleavage site that can be predicted in a given sequence using the method of Von Heijne ((1986) *Nucleic Acids Research* 14:4683–4691). Table I, below, describes the various morphogens identified to date, including their nomenclature as used herein, their Seq. ID references, and publication sources for the amino acid sequences for the full length proteins not included in the Seq. Listing. The disclosure of these publications is incorporated herein by reference.

TABLE I

| | |
|---|---|
| "OP-1" | Refers generically to the group of morphogenically active proteins expressed from part or all of a DNA sequence encoding OP-1 protein, including allelic and species variants thereof, e.g., human OP-1 ("hOP-1", Seq. ID No. 5, mature protein amino acid sequence), or mouse OP-1 ("mOP-1", Seq. ID No. 6, mature |

TABLE I-continued

| | |
|---|---|
| | protein amino acid sequence.) The conserved seven cysteine skeleton is defined by residues 38 to 139 of Seq. ID Nos. 5 and 6. The cDNA sequences and the amino acids encoding the full length proteins are provided in Seq. Id Nos. 16 and 17 (hOP1) and Seq. ID Nos. 18 and 19 (mOP1.) The mature proteins are defined by residues 293–431 of Seq. ID No. 17 (hOP1) and 292–430 of Seq. ID. 19 (mOP1). The "pro" regions of the proteins, cleaved to yield the mature, morphogenically active proteins are defined essentially by residues 30–292 of Seq. ID No. 17 (hOPl) and residues 30–291 of Seq. ID No. 10 (mOP1). |
| "OP-2" | refers generically to the group of active proteins expressed from part or all of a DNA sequence encoding OP-2 protein, including allelic and species variants thereof, e.g., human OP-2 ("hOP-2", Seq. ID No. 7, mature protein amino acid sequence) or mouse OP-2 ("mOP-2", Seq. ID No. 8, mature protein amino acid sequence). The conserved seven cysteine skeleton is defined by residues 38 to 139 of Seq. ID Nos. 7 and 8. The cDNA sequences and the amino acids encoding the full length proteins are provided in Seq. ID Nos. 20 and 21 (hOP2) and Seq. ID Nos. 22 and 23 (mOP2.) The mature proteins are defined essentially by residues 264–402 of Seq. ID No. 21 (hOP2) and 261–399 of Seq. ID No. 23 (mOP2). The "pro" regions of the proteins, cleaved to yield the mature, morphogenically active proteins likely are defined essentially by residues 18–263 of Seq. ID No. 21 (hOP2) and residues 18–260 of Seq. ID No. 23 (mOP2) (Another cleavage site also occurs 21 residues upstream in both OP-2 proteins). |
| "CBMP2" | refers generically to the morphogenically active proteins expressed from a DNA sequence encoding the CBMP2 proteins, including allelic and species variants thereof, e.g., human CBMP2A, Seq ID No. 9) or human CBMP2B DNA, Seq. ID No. 10). The amino acid sequence for the full length proteins, referred to in the literature respectively as BMP2A and BMP2B, or as BMP2 and BMP4, appear in Wozney, et al. (1988) Science 242:1528–1534. The pro domain for BMP2 (BMP2A) likely includes residues 25–248 or 25–282 of the published prepro-polypeptide sequence; the mature protein, residues 249–396 or 283–396 of the published sequence. The pro domain for BMP4 (BMP2B) likely includes residues 25–256 or 25–292 of the published sequence; the mature protein, residues 257–408 of the published sequence or 293–408. |
| "DPP(fx)" | refers to protein sequences encoded by the Drosophila DPP gene and defining the conserved seven cysteine skeleton thereof (Seq. ID No. 11). The amino acid sequence for the full length protein appears in Padgett, et al (1987) Nature 325: 81–84. The pro domain likely extends from the signal peptide cleavage site to residue 456; the mature protein likely is defined by residues 457–588 of the published sequence. |
| "Vgl(fx)" | refers to protein sequences encoded by the Xenopus Vgl gene and defining the conserved seven cysteine skeleton thereof (Seq. ID No. 12). The amino acid sequence for the full length protein appears in |

TABLE I-continued

| | |
|---|---|
| | Weeks (1987) Cell 51: 861–867. The prodomain likely extends from the signal peptide cleavage site to residue 246 of the published sequence; the mature protein likely is defined by residues 247–360 of the published sequence. |
| "Vgr-1(fx)" | refers to protein sequences encoded by the murine Vgr-1 gene and defining the conserved seven cysteine skeleton thereof (Seq. ID No. 13). The amino acid sequence for the full length protein appears in Lyons, et al, (1989) PNAS 86: 4554-4558. The prodomain likely extends from the signal peptide cleavage site to residue 299 of the published sequence; the mature protein likely is defined by residues 300–438 as published. |
| "GDF-1(fx)" | refers to protein sequences encoded by the human GDF-1 gene and defining the conserved seven cysteine skeleton thereof (Seq. ID No. 14). The cDNA and encoded amino sequence for the full length protein is provided in Seq. ID. Nos. 32 and 33 respectively. The prodomain likely extends from the signal peptide cleavage site to residue 214 of Seq. ID No. 33; the mature protein likely is defined by residues 215–372 of Seq. ID No. 33. |
| "60A" | refers generically to the morphogenically active proteins expressed from part or all of a DNA sequence encoding the Drosophila 60A proteins. The cDNA and encoded full length amino acid sequence for the "60A(fx)" refers to the protein sequences defining the conserved seven cysteine skeleton thereof (residues 354 to 455 of Seq. ID No. 24). The prodomain likely extends from the signal peptide cleavage site to residue 324 of Seq. ID No. 24; the mature protein likely is defined by residues 325–455 of Seq. ID No. 24. |
| "BMP3(fx)" | refers to protein sequences encoded by the human BMP3 gene and defining the conserved seven cysteine skeleton thereof (Seq. ID No. 26). The amino acid sequence for the full length protein appears in Wozney et al. (1988) Science 242: 1528–1534. The pro domain likely extends from the signal peptide cleavage site to residue 290 of the published sequence; the mature protein likely is defined by residues 291–472 as published. |
| "BMP5(fx)" | refers to protein sequences encoded by the human BMP5 gene and defining the conserved seven cysteine skeleton thereof (Seq. ID No. 27). The amino acid sequence for the full length protein appears in Celeste, et al. (1991) PNAS 87: 9843–9847. The pro domain likely extends from the signal peptide cleavage site to residue 316 of the published sequence; the mature protein likely is defined by residues 317–454 as published. |
| "BMP6(fx)" | refers to protein sequences encoded by the human BMP6 gene and defining the conserved seven cysteine skeleton thereof (Seq. ID No. 28). The amino acid sequence for the full length protein appears in Celeste, et al. (1990) PNAS 87: 9843–5847. The pro domain likely includes extends from the signal peptide cleavage site to residue 374 of the published sequence; the mature sequence likely includes residues 375–513 as published. |

The OP-2 proteins (comprising, e.g., Seq. ID Nos. 7 and 8) have an additional cysteine residue in this region (e.g., see residue 41 of Seq. ID Nos. 7 and 8), in addition to the conserved cysteine skeleton in common with the other proteins in this family. The GDF-1 protein (comprising, e.g., Seq. ID No. 14), has a four amino acid insert within the conserved skeleton (residues 44–47 of Seq. ID No. 14) but this insert likely does not interfere with the relationship of the cysteines in the folded structure. In addition, the CBMP2 proteins (comprising, e.g., Seq. ID Nos. 9 and 10) are missing one amino acid residue within the cysteine skeleton.

The morphogens are inactive when reduced, but are ctive as oxidized homodimers and when oxidized in combination with other morphogens of this invention. Thus, as defined herein, a morphogen is a dimeric protein comprising a pair of polypeptide chains, wherein each polypeptide chain comprises at least the C-terminal six cysteine skeleton defined by residues 43–139 of Seq. ID No. 5, including functionally equivalent arrangements of these cysteines (e.g., amino acid insertions or deletions which alter the linear arrangement of the cysteines in the sequence but not their relationship in the folded structure), such that, when the polypeptide chains are folded, the dimeric protein species comprising the pair of polypeptide chains has the appropriate three-dimensional structure, including the appropriate intra- or inter-chain disulfide bonds such that the protein is capable of acting as a morphogen as defined herein. Specifically, the morphogens generally are capable of all of the following biological functions in a morphogenically permissive environment: stimulating proliferation of progenitor cells; stimulating the differentiation of progenitor cells; stimulating the proliferation of differentiated cells; and supporting the growth and maintenance of differentiated cells, including the "redifferentiation" of transformed cells. In addition, it is also anticipated that these morphogens are capable of inducing redifferentiation of committed cells under appropriate environmental conditions.

In one preferred aspect, the morphogens of this invention comprise one of two species of generic amino acid sequences: Generic Sequence 1 (Seq. ID No. 1) or Generic Sequence 2 (Seq. ID No. 2); where each Xaa indicates one of the 20 naturally-occurring L-isomer, α-amino acids or a derivative thereof. Generic Sequence 1 comprises the conserved six cysteine skeleton and Generic Sequence 2 comprises the conserved six cysteine (at residue 36 of Seq. ID No. 2) skeleton plus the additional cysteine identified in OP-2 (comprising, e.g., Seq. ID No. 6 or 7). In another preferred aspect, these sequences further comprise the following additional sequence at their N-terminus:

Cys Xaa Xaa Xaa Xaa (Seq. ID No. 15)
1                 5

Preferred amino acid sequences within the foregoing generic sequences include: Generic Sequence 3 (Seq. ID No. 3), Generic Sequence 4 (Seq. ID No. 4), Generic Sequence 5 (Seq. ID No. 30) and Generic Sequence 6 (Seq. ID No. 31). These Generic Sequences accommodate the homologies shared among the various preferred members of this morphogen family identified in Table II, as well as the amino acid sequence variation among them. Specifically, Generic Sequences 3 and 4 are composite amino acid sequences of the following proteins presented in Table II: human OP-1 (hOP-1, comprising, e.g., Seq. ID Nos. 5 and 16–17), mouse OP-1 (mOP-1, comprising, e.g., Seq. ID Nos. 6 and 18–19), human and mouse OP-2 (comprising, e.g., Seq. ID Nos. 7, 8, and 20–22), CBMP2A (Seq. ID No. 9), CBMP2B (comprising, e.g., Seq. ID No. 10), DPP (from Drosophila comprising, e.g, Seq. ID No. 11), Vgl, (from Xenopus comprising, e.g., Seq. ID No. 12), Vgr-1 (from mouse comprising, e.g., Seq. ID No. 13), and GDF-1 (from mouse comprising, e.g., Seq. ID No. 14.) The generic sequences include both the amino acid identity shared by the sequences in Table II, as well as alternative residues for the variable positions within the sequence. Note that these generic sequences allow for an additional cysteine at position 41 or 46 in Generic Sequences 3 or 4 (Seq. ID Nos. 3 or 4), respectively, providing an appropriate cysteine skeleton where inter- or intramolecular disulfide bonds can form, and contain certain critical amino acids which influence the tertiary structure of the proteins.

Generic Sequence 3 (Seq. ID No. 3)

Leu Tyr Val Xaa Phe
1           5

Xaa Xaa Xaa Gly Trp Xaa Xaa Trp Xaa
              10

Xaa Ala Pro Xaa Gly Xaa Xaa Ala
15                  20

Xaa Tyr Cys Xaa Gly Xaa Cys Xaa
        25              30

Xaa Pro Xaa Xaa Xaa Xaa Xaa
              35

Xaa Xaa Xaa Asn His Ala Xaa Xaa
        40                  45

Xaa Xaa Leu Xaa Xaa Xaa Xaa Xaa
              50

Xaa Xaa Xaa Xaa Xaa Xaa Xaa Cys
55                      60

Cys Xaa Pro Xaa Xaa Xaa Xaa Xaa
              65

Xaa Xaa Xaa Leu Xaa Xaa Xaa
70              75

Xaa Xaa Xaa Xaa Val Xaa Leu Xaa
              80

Xaa Xaa Xaa Xaa Met Xaa Val Xaa
85                  90

Xaa Cys Gly Cys Xaa
        95 wherein each Xaa is independently selected from a group of one or more specified amino acids defined as follows: "Res." means "residue" and Xaa at res.4=(Ser, Asp or Glu); Xaa at res.6=(Arg, Gln, Ser or Lys); Xaa at res.7=(Asp or Glu); Xaa at res.8=(Leu or Val); Xaa at res.11=(Gln, Leu, Asp, His or Asn); Xaa at res.12=(Asp, Arg or Asn); Xaa at res.14=(Ile or Val); Xaa at res.15=(Ile or Val); Xaa at res.18=(Glu, Gln, Leu, Lys, Pro or Arg); Xaa at res.20=(Tyr or Phe); Xaa at res.21=(Ala, Ser, Asp, Met, His, Leu or Gln); Xaa at res.23=(Tyr, Asn or Phe); Xaa at res.26=(Glu, His, Tyr, Asp or Gln); Xaa at res.28=(Glu, Lys, Asp or Gln); Xaa at res.30=(Ala, Ser, Pro or Gln); Xaa at res.31=(Phe, Leu or Tyr); Xaa at res.33=(Leu or Val); Xaa at res.34=(Asn, Asp, Ala or Thr); Xaa at res.35=(Ser, Asp, Glu, Leu or Ala); Xaa at res.36=(Tyr, Cys, His, Ser or Ile); Xaa at res.37=(Met, Phe, Gly or Leu); Xaa at res.38=(Asn or Ser); Xaa at res.39=(Ala, Ser or Gly); Xaa at res.40=(Thr, Leu or Ser); Xaa at res.44=(Ile or Val); Xaa at res.45=(Val or Leu); Xaa at res.46=(Gln or Arg); Xaa at res.47=(Thr, Ala or Ser); Xaa at res.49=(Val or Met); Xaa at res.50=(His or Asn); Xaa at res.51=(Phe, Leu, Asn, Ser, Ala or Val); Xaa at res.52=(Ile, Met, Asn, Ala or Val); Xaa at res.53=(Asn, Lys, Ala or Glu); Xaa at res.54=(Pro or Ser); Xaa at res.55=(Glu, Asp, Asn, or Gly); Xaa at res.56=(Thr, Ala, Val, Lys, Asp, Tyr, Ser or Ala); Xaa at res.57=(Val, Ala or Ile); Xaa at res.58=(Pro or Asp); Xaa at res.59=(Lys or Leu); Xaa at res.60=(Pro or Ala); Xaa at res.63=(Ala or Val); Xaa at res.65=(Thr or Ala); Xaa at res.66=(Gln, Lys, Arg or Glu); Xaa at res.67=(Leu, Met or Val); Xaa at res.68=(Asn, Ser or Asp); Xaa at res.69=(Ala, Pro or Ser); Xaa at res.70=(Ile, Thr or Val); Xaa at res.71=(Ser or Ala); Xaa at res.72=(Val or Met); Xaa at res.74=(Tyr or Phe); Xaa at res.75=(Phe, Tyr or Leu); Xaa at res.76=(Asp or Asn); Xaa at res.77=(Asp, Glu, Asn or Ser); Xaa at res.78=(Ser, Gln, Asn or Tyr); Xaa at res.79=(Ser, Asn, Asp or Glu); Xaa at res.80=(Asn, Thr or Lys); Xaa at res.82=(Ile or Val); Xaa at res.84=(Lys or Arg); Xaa at res.85=(Lys, Asn, Gln or His); Xaa at res.86=(Tyr or His); Xaa at res.87=(Arg, Gln or Glu); Xaa at res.88=(Asn, Glu or Asp); Xaa at res.90=(Val, Thr or Ala); Xaa at res.92=(Arg, Lys, Val, Asp or Glu); Xaa at res.93=(Ala, Gly or Glu); and Xaa at res.97=(His or Arg);

Generic Sequence 4 (Seq. ID No. 4)

Cys Xaa Xaa Xaa Xaa Leu Tyr Val Xaa Phe
1           5                   10

Xaa Xaa Xaa Gly Trp Xaa Xaa Trp Xaa
                15

Xaa Ala Pro Xaa Gly Xaa Xaa Ala
20              25

Xaa Tyr Cys Xaa Gly Xaa Cys Xaa
        30              35

Xaa Pro Xaa Xaa Xaa Xaa Xaa
            40

Xaa Xaa Xaa Asn His Ala Xaa Xaa
        45              50

Xaa Xaa Leu Xaa Xaa Xaa Xaa Xaa
                55

Xaa Xaa Xaa Xaa Xaa Xaa Xaa Cys
    60                  65

Cys Xaa Pro Xaa Xaa Xaa Xaa Xaa
            70

Xaa Xaa Xaa Leu Xaa Xaa Xaa
75              80
Xaa Xaa Xaa Xaa Val Xaa Leu Xaa
            85

Xaa Xaa Xaa Xaa Met Xaa Val Xaa
90                  95

Xaa Cys Gly Cys Xaa
        100 wherein each Xaa is independently selected from a group of one or more specified amino acids as defined by the following: "Res." means "residue" and Xaa at res.2=(Lys or Arg); Xaa at res.3=(Lys or Arg); Xaa at res.4=(His or Arg); Xaa at res.5=(Glu, Ser, His, Gly, Arg or Pro); Xaa at res.9=(Ser, Asp or Glu); Xaa at res.11=(Arg, Gln, Ser or Lys); Xaa at res.12=(Asp or Glu); Xaa at res.13=(Leu or Val); Xaa at res.16(Gln, Leu, Asp, His or Asn); Xaa at res.17=(Asp, Arg, or Asn); Xaa at res.19=(Ile or Val); Xaa at res.20=(Ile or Val); Xaa at res.23=(Glu, Gln, Leu, Lys, Pro or Arg); Xaa at res.25=(Tyr or Phe); Xaa at res.26=(Ala, Ser, Asp, Met, His, Leu, or Gln); Xaa at res.28=(Tyr, Asn or Phe); Xaa at res.31=(Glu, His, Tyr, Asp or Gln); Xaa at res.33=Glu, Lys, Asp or Gln); Xaa at res.35=(Ala, Ser or Pro); Xaa at res.36=(Phe, Leu or Tyr); Xaa at res.38=(Leu or Val); Xaa at res.39=(Asn, Asp, Ala or Thr); Xaa at res.40=(Ser, Asp, Glu, Leu or Ala); Xaa at res.41=(Tyr, Cys, His, Ser or Ile); Xaa at res.42=(Met, Phe, Gly or Leu); Xaa at res.44=(Ala, Ser or Gly); Xaa at res.45=(Thr, Leu or Ser); Xaa at res.49=(Ile or Val); Xaa at res.50=(Val or Leu); Xaa at res.51=(Gln or Arg); Xaa at res.52=(Thr, Ala or Ser); Xaa at res.54=(Val or Met); Xaa at res.55=(His or Asn); Xaa at res.56=(Phe, Leu, Asn, Ser, Ala or Val); Xaa at res.57=(Ile, Met, Asn, Ala or Val); Xaa at res.58=(Asn, Lys, Ala or Glu); Xaa at res.59=(Pro or Ser); Xaa at res.60=(Glu, Asp, or Gly); Xaa at res.61=(Thr, Ala, Val, Lys, Asp, Tyr, Ser or Ala); Xaa at res.62=(Val, Ala or Ile); Xaa at res.63=(Pro or Asp); Xaa at res.64=(Lys or Leu); Xaa at res.65=(Pro or Ala); Xaa at res.68=(Ala or Val); Xaa at res.70=(Thr or Ala); Xaa at res.71=(Gln, Lys, Arg or Glu); Xaa at res.72=(Leu, Met or Val); Xaa at res.73=(Asn, Ser or Asp); Xaa at res.74=(Ala, Pro or Ser); Xaa at res.75=(Ile, Thr or Val); Xaa at res.76=(Ser or Ala); Xaa at res.77=(Val or Met); Xaa at res.79=(Tyr or Phe); Xaa at res.80=(Phe, Tyr or Leu); Xaa at res.81=(Asp or Asn); Xaa at res.82=(Asp, Glu, Asn or Ser); Xaa at res.83=(Ser, Gln, Asn or Tyr); Xaa at res.84=(Ser, Asn, Asp or Glu); Xaa at res.85=(Asn, Thr or Lys); Xaa at res.87=(Ile or Val); Xaa at res.89=(Lys or Arg); Xaa at res.90=(Lys, Asn, Gln or His); Xaa at res.91=(Tyr or His); Xaa at res.92=(Arg, Gln or Glu); Xaa at res.93=(Asn, Glu or Asp); Xaa at res.95=(Val, Thr or Ala); Xaa at res.97=(Arg, Lys, Val, Asp or Glu); Xaa at res.98=(Ala, Gly or Glu); and Xaa at res.102=(His or Arg).

Similarly, Generic Sequence 5 (Seq. ID No. 30) and Generic Sequence 6 (Seq. ID No. 31) accommodate the homologies shared among all the morphogen protein family members identified in Table II. Specifically, Generic Sequences 5 and 6 are composite amino acid sequences of human OP-1 (hOP-1, comprising, e.g., Seq. ID Nos. 5 and 16–17), mouse OP-1 (mOP-1comprising, e.g., Seq. ID Nos. 6 and 18–19), human and mouse OP-2 (comprising, e.g., Seq. ID Nos. 7, 8, and 20–22), CBMP2A (comprising, e.g., Seq. ID No. 9), CBMP2B (comprising, e.g., Seq. ID No. 10), DPP (from Drosophila comprising, e.g., Seq. ID No. 11), Vgl, (from Xenopus comprising, e.g., Seq. ID No. 12), Vgr-1 (from mouse comprising, e.g., Seq. ID No. 13), and GDF-1 (from mouse comprising, e.g., Seq. ID No. 14), human BMP3 (comprising, e.g., Seq. ID No. 26), human BMP5 (comprising, e.g., Seq. ID No. 27), human BMP6 (comprising, e.g., Seq. ID No. 28) and 60(A) (from Drosophila comprising, e.g., Seq.

ID Nos. 24–25). The generic sequences include both the 25 amino acid identity shared by these sequences in the C-terminal domain, defined by the six and seven cysteine skeletons (Generic Sequences 5 and 6, respectively), as well as alternative residues for the variable positions within the sequence. As for Generic Sequences 3 and 4 (Seq ID. Nos. 2 and 4), Generic Sequences 5 and 6 (Seq. ID Nos. 30 and 31) allow for an additional cysteine at position 41 (Generic Sequence 5) or position 46 (Generic Sequence 6), providing an appropriate cysteine skeleton where inter- or intramolecular disulfide bonds can form, and containing certain critical amino acids which influence the tertiary structure of the proteins.

Generic Sequence 5 (Seq. ID No. 30)

Leu Xaa Xaa Xaa Phe
1               5

Xaa Xaa Xaa Gly Trp Xaa Xaa Trp Xaa
                10

Xaa Xaa Pro Xaa Xaa Xaa Xaa Ala
15                  20

-continued
Generic Sequence 5 (Seq. ID No. 30)

```
Xaa Tyr Cys Xaa Gly Xaa Cys Xaa
    25              30
Xaa Pro Xaa Xaa Xaa Xaa Xaa
            35
Xaa Xaa Xaa Asn His Ala Xaa Xaa
        40              45
Xaa Xaa Xaa Xaa Xaa Xaa Xaa
            50
Xaa Xaa Xaa Xaa Xaa Xaa Cys
55              60
Cys Xaa Pro Xaa Xaa Xaa Xaa
            65
Xaa Xaa Xaa Leu Xaa Xaa Xaa
70                  75
Xaa Xaa Xaa Xaa Val Xaa Leu Xaa
            80
Xaa Xaa Xaa Xaa Met Xaa Val Xaa
85                  90
Xaa Cys Xaa Cys Xaa
        95
``` wherein each Xaa is independently selected from a group of one or more specified amino acids defined as follows: "Res." means "residue" and Xaa at res.2=(Tyr or Lys); Xaa at res.3=Val or Ile); Xaa at res.4=(Ser, Asp or Glu); Xaa at res.6=(Arg, Gln, Ser, Lys or Ala); Xaa at res.7=(Asp, Glu or Lys); Xaa at res.8=(Leu, Val or Ile); Xaa at res.11=(Gln, Leu, Asp, His, Asn or Ser); Xaa at res.12=(Asp, Arg, Asn or Glu); Xaa at res.14=(Ile or Val); Xaa at res.15=(Ile or Val); Xaa at res.16(Ala or Ser); Xaa at res.18=(Glu, Gln, Leu, Lys, Pro or Arg); Xaa at res.19=(Gly or Ser); Xaa at res.20=(Tyr or Phe); Xaa at res.21=(Ala, Ser, Asp, Met, His, Gln, Leu or Gly); Xaa at res.23=(Tyr, Asn or Phe); Xaa at res.26=(Glu, His, Tyr, Asp, Gln or Ser); Xaa at res.28=(Glu, Lys, Asp, Gln or Ala); Xaa at res.30=(Ala, Ser, Pro, Gln or Asn); Xaa at res.31=(Phe, Leu or Tyr); Xaa at res.33=(Leu, Val or Met); Xaa at res.34=(Asn, Asp, Ala, Thr or Pro); Xaa at res.35=(Ser, Asp, Glu, Leu, Ala or Lys); Xaa at res.36=(Tyr, Cys, His, Ser or Ile); Xaa at res.37=(Met, Phe, Gly or Leu); Xaa at res.38=(Asn, Ser or Lys); Xaa at res.39=(Ala, Ser, Gly or Pro); Xaa at res.40=(Thr, Leu or Ser); Xaa at res.44=(Ile, Val or Thr); Xaa at res.45=(Val, Leu or Ile); Xaa at res.46=(Gln or Arg); Xaa at res.47=(Thr, Ala or Ser); Xaa at res.48=(Leu or Ile); Xaa at res.49=(Val or Met); Xaa at res.50=(His, Asn or Arg); Xaa at res.51=(Phe, Leu, Asn, Ser, Ala or Val); Xaa at res.52=(Ile, Met, Asn, Ala, Val or Leu); Xaa at res.53=(Asn, Lys, Ala, Glu, Gly or Phe); Xaa at res.54=(Pro, Ser or Val); Xaa at res.55=(Glu, Asp, Asn, Gly, Val or Lys); Xaa at res.56=(Thr, Ala, Val, Lys, Asp, Tyr, Ser, Ala, Pro or His); Xaa at res.57=(Val, Ala or Ile); Xaa at res.58=(Pro or Asp); Xaa at res.59=(Lys, Leu or Glu); Xaa at res.60=(Pro or Ala); Xaa at res.63=(Ala or Val); Xaa at res.65=(Thr, Ala or Glu); Xaa at res.66=(Gln, Lys, Arg or Glu); Xaa at res.67=(Leu, Met or Val); Xaa at res.68=(Asn, Ser, Asp or Gly); Xaa at res.69=(Ala, Pro or Ser); Xaa at res.70=(Ile, Thr, Val or Leu); Xaa at res.71=(Ser, Ala or Pro); Xaa at res.72=(Val, Met or Ile); Xaa at res.74=(Tyr or Phe); Xaa at res.75=(Phe, Tyr, Leu or His); Xaa at res.76=(Asp, Asn or Leu); Xaa at res.77=(Asp, Glu, Asn or Ser); Xaa at res.78=(Ser, Gln, Asn, Tyr or Asp); Xaa at res.79=(Ser, Asn, Asp, Glu or Lys); Xaa at res.80=(Asn, Thr or Lys); Xaa at res.82=(Ile, Val or Asn); Xaa at res.84=(Lys or Arg); Xaa at res.85=(Lys, Asn, Gln, His or Val); Xaa at res.86=(Tyr or His); Xaa at res.87=(Arg, Gln, Glu or Pro); Xaa at res.88=(Asn, Glu or Asp); Xaa at res.90=(Val, Thr, Ala or Ile); Xaa at res.92=(Arg, Lys, Val, Asp or Glu); Xaa at res.93=(Ala, Gly, Glu or Ser); Xaa at res.95=(Gly or Ala) and Xaa at res.97=(His or Arg).

Generic Sequence 6 (Seq. ID No. 31)

```
Cys Xaa Xaa Xaa Xaa Leu Xaa Xaa Xaa Phe
1               5                   10
Xaa Xaa Xaa Gly Trp Xaa Xaa Trp Xaa
            15
Xaa Xaa Pro Xaa Xaa Xaa Xaa Ala
20                  25
Xaa Tyr Cys Xaa Gly Xaa Cys Xaa
        30              35
Xaa Pro Xaa Xaa Xaa Xaa Xaa
            40
Xaa Xaa Xaa Asn His Ala Xaa Xaa
        45              50
Xaa Xaa Xaa Xaa Xaa Xaa Xaa
            55
Xaa Xaa Xaa Xaa Xaa Xaa Cys
60                  65
Cys Xaa Pro Xaa Xaa Xaa Xaa
            70
Xaa Xaa Xaa Leu Xaa Xaa Xaa
75                  80
Xaa Xaa Xaa Xaa Val Xaa Leu Xaa
            85
Xaa Xaa Xaa Xaa Met Xaa Val Xaa
90                  95
Xaa Cys Xaa Cys Xaa
        100
``` wherein each Xaa is independently selected from a group of one or more specified amino acids as defined by the following: "Res." means "residue" and Xaa at res.2=(Lys, Arg, Ala or Gln); Xaa at res.3=(Lys, Arg or Met); Xaa at res.4=(His, Arg or Gln); Xaa at res.5=(Glu, Ser, His, Gly, Arg, Pro, Thr, or Tyr); Xaa at res.7=(Tyr or Lys); Xaa at res.8=(Val or Ile); Xaa at res.9=(Ser, Asp or Glu); Xaa at res.11=(Arg, Gln, Ser, Lys or Ala); Xaa at res.12=(Asp, Glu, or Lys); Xaa at res.13=(Leu, Val or Ile); Xaa at res.16=(Gln, Leu, Asp, His, Asn or Ser); Xaa at res.17=(Asp, Arg, Asn or Glu); Xaa at res.19=(Ile or Val); Xaa at res.20=(Ile or Val); Xaa at res.21=(Ala or Ser); Xaa at res.23=(Glu, Gln, Leu, Lys, Pro or Arg); Xaa at res.24=(Gly or Ser); Xaa at res.25=(Tyr or Phe); Xaa at res.26=(Ala, Ser, Asp, Met, His, Gln, Leu, or Gly); Xaa at res.28=(Tyr, Asn or Phe); Xaa at res.31=(Glu, His, Tyr, Asp, Gln or Ser); Xaa at res.33=Glu, Lys, Asp, Gln or Ala); Xaa at res.35=(Ala, Ser, Pro, Gln or Asn); Xaa at res.36=(Phe, Leu or Tyr); Xaa at res.38=(Leu, Val or Met); Xaa at res.39=(Asn, Asp, Ala, Thr or Pro); Xaa at res.40=(Ser, Asp, Glu, Leu, Ala or Lys); Xaa at res.41=(Tyr, Cys, His, Ser or Ile); Xaa at res.42=(Met, Phe, Gly or Leu); Xaa at res.43=(Asn, Ser or Lys); Xaa at res.44=(Ala, Ser, Gly or Pro); Xaa at res.45=(Thr, Leu or Ser); Xaa at res.49=(Ile, Val or Thr); Xaa at res.50=(Val, Leu or Ile); Xaa at res.51=(Gln or Arg); Xaa at res.52=(Thr, Ala or Ser); Xaa at res.53=(Leu or Ile); Xaa at res.54=(Val or Met); Xaa at res.55=(His, Asn or Arg); Xaa at res.56=(Phe, Leu, Asn, Ser, Ala or Val); Xaa at res.57=(Ile, Met, Asn, Ala, Val or Leu); Xaa at res.58=(Asn, Lys, Ala, Glu, Gly or Phe); Xaa at res.59=(Pro, Ser or Val); Xaa at res.60=(Glu, Asp, Gly, Val or Lys); Xaa at res.61=(Thr, Ala, Val, Lys, Asp, Tyr, Ser, Ala, Pro or His); Xaa at res.62=(Val, Ala or Ile); Xaa at res.63=(Pro or Asp); Xaa at res.64=(Lys, Leu or Glu); Xaa at res.65=(Pro or Ala); Xaa at res.68=(Ala or Val); Xaa at res.70=(Thr, Ala or Glu); Xaa at res.71=(Gln, Lys, Arg or Glu); Xaa at res.72=(Leu, Met or Val); Xaa at res.73=(Asn, Ser, Asp or Gly); Xaa at res.74=(Ala, Pro or Ser); Xaa at res.75=(Ile, Thr, Val or Leu); Xaa at res.76=(Ser, Ala or Pro); Xaa at res.77=(Val, Met or Ile); Xaa at res.79=(Tyr or Phe); Xaa at res.80=(Phe, Tyr, Leu or His); Xaa at res.81=(Asp, Asn or Leu); Xaa at res.82=(Asp, Glu, Asn or Ser); Xaa at res.83=(Ser, Gln, Asn, Tyr or Asp); Xaa at res.84=(Ser, Asn, Asp, Glu or Lys); Xaa at res.85=(Asn, Thr or Lys); Xaa at res.87=(Ile, Val or Asn); Xaa at res.89=(Lys or Arg); Xaa at res.90=(Lys, Asn, Gln, His or Val); Xaa at res.91=(Tyr or His); Xaa at res.92=(Arg, Gln, Glu or Pro); Xaa at res.93=(Asn, Glu or Asp); Xaa at res.95=(Val, Thr, Ala or Ile); Xaa at res.97=(Arg, Lys, Val, Asp or Glu); Xaa at res.98=(Ala, Gly, Glu or Ser); Xaa at res.100=(Gly or Ala); and Xaa at res.102=(His or Arg).

Particularly useful sequences for use as morphogens in this invention include the C-terminal domains, e.g., the C-terminal 96–102 amino acid residues of vgl (Seq. ID No. 12), Vgr-1 (Seq. ID No. 13), DPP (Seq. ID No. 11), OP-1 (Seq. ID No. 5 or 6), OP-2 (Seq. ID No. 7 or 8), CBMP-2A (Seq. ID No. 9), CBMP-2B (Seq. ID No. 10), GDF-1 (Seq. ID No. 14) Table II, below, as well as proteins comprising the C-terminal domains of 60A (residues 354–455 of Seq. ID No. 25), BMP3 (Seq. ID No. 26), BMP5 (Seq. ID No. 27) and BMP6 (Seq. ID No. 28) see also Table II,, all of which include at least the conserved six or seven cysteine skeleton. In addition, biosynthetic constructs designed from the generic sequences, such as COP-1, 3–5, 7, 16, disclosed in U.S. Pat. No. 5,011,691, also are useful. Other sequences include the inhibins/activin proteins (see, for example, U.S. Pat. Nos. 4,968,590 and 5,011,691). Accordingly, other useful sequences are those sharing at least 70% amino acid sequence homology or "similarity", and preferably 80% homology or similarity with any of the sequences above. These are anticipated to include allelic and species variants and mutants, and biosynthetic muteins, as well as novel members of this morphogenic family of proteins. Particularly envisioned in the family of related proteins are those proteins exhibiting morphogenic activity and wherein the amino acid changes from the preferred sequences include conservative changes, e.g., those as defined by Dayoff et al., *Atlas of Protein Sequence and Structure;* vol. 5, Suppl. 3, pp. 345–362, (M. O. Dayoff, ed., Nat'l BioMed. Research Fdn., Washington, D.C. 1979). As used herein, potentially useful sequences are aligned with a known morphogen sequence using the method of Needleman et al. ((1970) *J.Mol.Biol.* 48:443–453) and identities calculated by the Align program (DNAstar, Inc.). "Homology" or "similarity" as used herein includes allowed conservative changes as defined by Dayoff et al.

The currently most preferred protein sequences useful as morphogens in this invention include those having greater than 60% identity, preferably greater than 65% identity, with the amino acid sequence defining the conserved six cysteine skeleton of hOP1 (e.g., residues 43–139 of Seq. ID No. 5). These most preferred sequences include both allelic and species variants of the OP-1 and OP-2 proteins (comprising, respectively, e.g., Seq. ID Nos. 5–8), including the Drosophila 60A protein (comprising e.g., Seq. ID NO. 25). Accordingly, in another preferred aspect of the invention, useful morphogens include active proteins comprising species of polypeptide chains having the generic amino acid sequence herein referred to as "OPX"(Seq. ID No. 29), which accommodates the homologies between the various identified species of OP1 and OP2 (comprising the sequences shown in Seq. ID Nos. 5–8(Seq. ID No. 29).

The morphogens useful in the methods, composition and devices of this invention include proteins comprising any of the polypeptide chains described above, whether isolated from naturally-occurring sources, or produced by recombinant DNA or other synthetic techniques, and includes allelic and species variants of these proteins, naturally-occurring or biosynthetic mutants thereof, as well as various truncated and fusion constructs. Deletion or addition mutants also are envisioned to be active, including those which may alter the conserved C-terminal cysteine skeleton, provided that the alteration does not functionally disrupt the relationship of these cysteines in the folded structure. Accordingly, such active forms are considered the equivalent of the specifically described constructs disclosed herein. The proteins may include forms having varying glycosylation patterns, varying N-termini, a family of related proteins having regions of amino acid sequence homology, and active truncated, chimeric and/or mutated forms of native or biosynthetic proteins, produced by expression of recombinant DNA in host cells.

The morphogenic proteins can be expressed from intact, chimeric and/or truncated cDNA or from synthetic DNAs in procaryotic or eucaryotic host cells, and purified, cleaved, refolded, and dimerized to form morphogenically active compositions. Currently preferred host cells include *E. coli* or mammalian cells, such as CHO, COS or BSC cells. A detailed description of the morphogens useful in the methods, compositions and devices of this invention is disclosed in commonly owned U.S. patent application Ser. Nos. 752,764, filed Aug. 30, 1991 (now abandoned), and 667,274, filed Mar. 11, 1991 (now abandoned), the disclosure of which are incorporated herein by reference.

Thus, in view of this disclosure, skilled genetic engineers can isolate genes from cDNA or genomic libraries of various different species which encode appropriate amino acid sequences, or construct DNAs from oligonucleotides, and then can express them in various types of host cells, including both procaryotes and eucaryotes, to produce large quantities of active proteins capable of maintaining liver function in a mammal, including correcting liver function deficiencies and stimulating hepatic tissue regeneration and repair in a variety of mammals, including humans.

The foregoing and other objects, features and advantages of the present invention will be made more apparent from the following detailed description of the invention.

BRIEF DESCRIPTION OF THE DRAWINGS

The foregoing and other objects and features of this invention, as well as the invention itself, may be more fully understood from the following description, when read together with the accompanying drawings, in which.

DETAILED DESCRIPTION OF THE INVENTION

Figure 1:
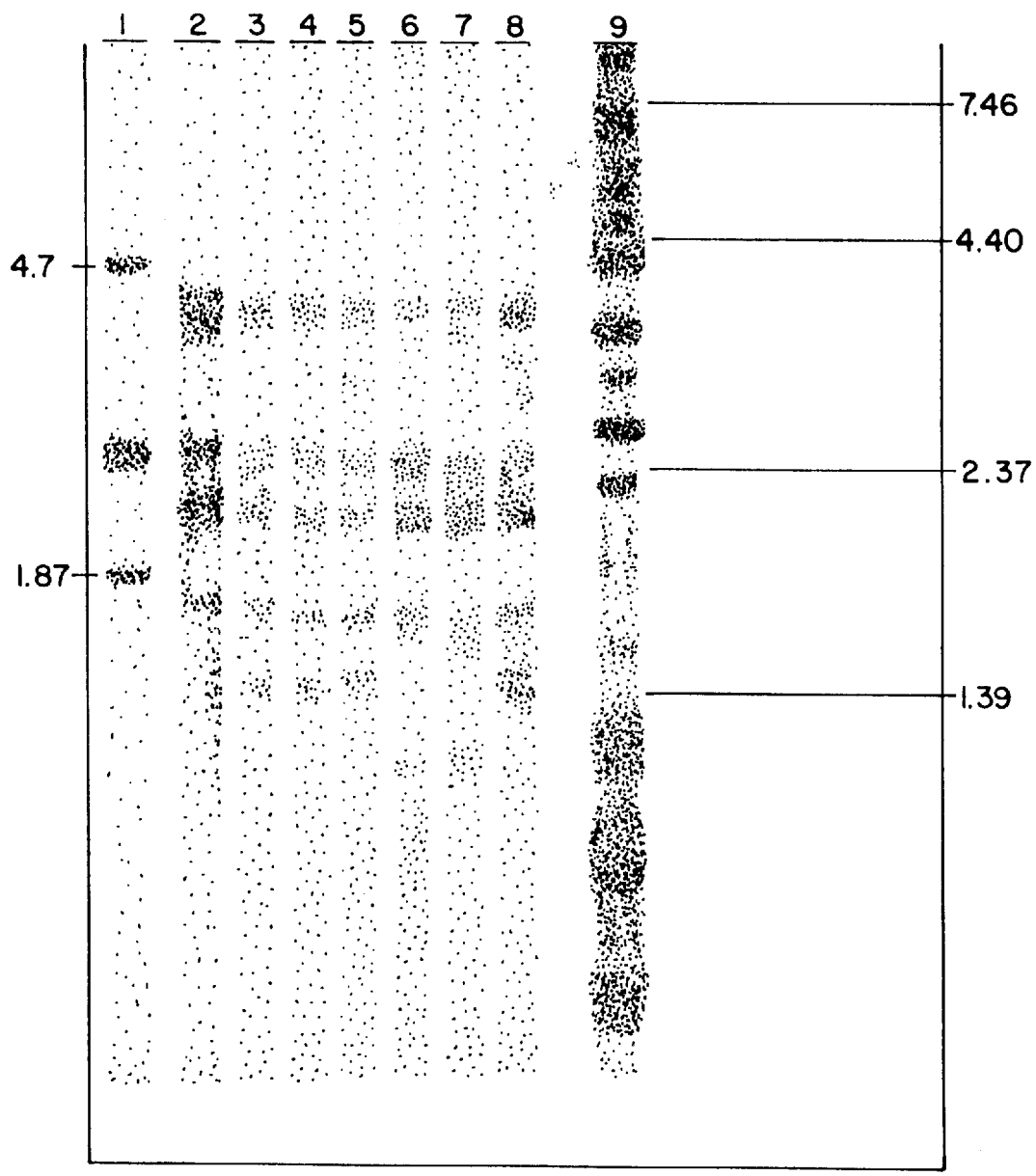
FIG. 1 is a photograph of a Northern blot identifying OP-1-specific mRNA expression in developing liver tissue in embryonic and postnatal mouse.

It now has been discovered that the proteins described herein are effective agents for maintaining liver function in a mammal. As described herein, these proteins ("morphogens") are capable of inducing hepatic tissue regeneration and repair under conditions where true tissue morphogenesis typically does not occur, including stimulating the proliferation and differentiation of hepatocytic progenitor cells. The proteins also are capable of providing a cytoprotective effect to alleviate the tissue destructive effects associated with immunologically-related hepatic tissue damage. Accordingly, the proteins may be used as part of a protocol for regenerating damaged or lost hepatic tissue, correcting a liver function deficiency, and enhancing the viability of a tissue or organ to be transplanted in a mammal. The morphogens also may be used in a gene therapy protocol to correct a protein deficiency in a mammal.

Provided below are detailed descriptions of suitable morphogens useful in the methods, compositions and devices of this invention, as well as methods for their administration and application, and numerous, nonlimiting examples which 1) illustrate the suitability of the morphogens and morphogen-stimulating agents described herein as therapeutic agents for maintaining liver function in a mammal; and 2) provide assays with which to test candidate morphogens and morphogen-stimulating agents for their efficacy. Specifically, the examples demonstrate the expression distribution of endogenous morphogen (Example 1), the expression of endogenous morphogen during liver formation in a developing embryo (Example 2), the ability of morphogens to induce proliferation of primary hepatocytes (Example 3), morphogen-induced liver tissue morphogenesis following partial hepatectomy (Example 4); endogenous morphogen expression during hepatic tissue repair following toxin-induced tissue damage (Examples 5); the inhibitory effect of morphogens on the body's cellular and humoral immune response (Example 6); effect of morphogen on fibrogenesis (Example 7); morphogen utility in liver diagnostic procedures (Example 8), and a screening assay for testing candidate morphogen-stimulating agents (Example 9).

I. Useful Morphogens

As defined herein a protein is morphogenic if it is capable of inducing the developmental cascade of cellular and molecular events that culminate in the formation of new, organ-specific tissue and comprises at least the conserved C-terminal six cysteine skeleton or its functional equivalent (see supra). Specifically, the morphogens generally are capable of all of the following biological functions in a morphogenically permissive environment: stimulating proliferation of progenitor cells; stimulating the differentiation of progenitor cells; stimulating the proliferation of differentiated cells; and supporting the growth and maintenance of differentiated cells, including the "redifferentiation" of transformed cells. Details of how the morphogens useful in the method of this invention first were identified, as well as a description on how to make, use and test them for morphogenic activity are disclosed in U.S. Ser. No. 667,274, filed Mar. 11, 1991 and U.S. Ser. No. 752,764, filed Aug. 30, 1991, both now abandoned the disclosures of which are hereby incorporated by reference. A candidate morphogen or morphogen composition can be evaluated for in vivo morphogenic utility generally according to the procedures set forth in U.S. Ser. No. 07/752,764 commonly owned, abandoned. The proteins and compositions may be injected or surgically implanted in a mammal, following any of a number of procedures well known in the art. For example, surgical implant bioassays may be performed essentially following the procedure of Sampath et al. (1983) PNAS 80:6591–6595.

Histological sectioning and staining is preferred to determine the extent of morphogenesis in vivo, particularly in tissue repair procedures. Excised implants are fixed in Bouins Solution, embedded in paraffin, and cut into 6–8 μm sections. Staining with toluidine blue or hemotoxylin/eosin demonstrates clearly the ultimate development of the new tissue. Twelve day implants are usually sufficient to determine whether the implants contain newly induced tissue.

Successful implants exhibit a controlled progression through the stages of induced tissue development allowing one to identify and follow the tissue-specific events that occur. For example, in endochondral bone formation the stages include:

(1) leukocytes on day one;

(2) mesenchymal cell migration and proliferation on days two and three;

(3) chondrocyte appearance on days five and six;

(4) cartilage matrix formation on day seven;

(5) cartilage calcification on day eight;

(6) vascular invasion, appearance of osteoblasts, and formation of new bone on days nine and ten;

(7) appearance of osteoblastic and bone remodeling and dissolution of the implanted matrix on days twelve to eighteen; and (8) hematopoietic bone marrow differentiation in the ossicle on day twenty-one.

In addition to histological evaluation, biological markers may be used as a marker for tissue morphogenesis. Useful markers include tissue-specific enzymes whose activity may be assayed (e.g., spectrophotometrically) after homogenization of the implant. These assays may be useful for quantitation and for obtaining an estimate of tissue formation quickly after the implants are removed from the animal. For example, alkaline phosphatase activity may be used as a marker for osteogenesis.

Incorporation of systemically provided morphogens may be followed using tagged morphogens (e.g., radioactively labelled) and determining their localization in new tissue, and/or by monitoring their disappearance from the circulatory system using a standard pulse-chase labeling protocol. The morphogen also may be provided with a tissue-specific molecular tag, whose uptake may be monitored and correlated with the concentration of morphogen provided.

The morphogen to be assayed according to the above-described exemplary procedures can be purified from naturally-sourced material, or can be recombinantly produced from procaryotic or eucaryotic host cells, into which genetic material encoding a morphogen, e.g., genetic material bearing one of the nucleic acid sequences disclosed herein, has been introduced. Alternatively, the above-described exemplary procedures can be used to determine whether a novel protein suspected of being a morphogen indeed has morphogenic activity.

Particularly useful proteins include those which comprise the naturally derived sequences disclosed in Table II. Other useful sequences include biosynthetic constructs such as those disclosed in U.S. Pat. No. 5,011,691, the disclosure of which is incorporated herein by reference (e.g., COP-1, COP-3, COP-4, COP-5, COP-7, and COP-16).

Accordingly, the morphogens useful in the methods and compositions of this invention also may be described by morphogenically active proteins having amino acid sequences sharing 70% or, preferably, 80% homology (similarity) with any of the sequences described above, where "homology" is as defined herein above.

The morphogens useful in the method of this invention also can be described by any of the 6 generic sequences described herein (Generic Sequences 1, 2, 3, 4, 5 and 6; Seq. ID Nos. 1, 2, 3, 4, 30 and 31). Generic sequences 1 and 2 also may include, at their N-terminus, the sequence Cys Xaa Xaa Xaa Xaa  (Seq. ID No. 15)
 1            5

Table II, set forth below, compares the amino acid sequences of the active regions of native proteins that have been identified as morphogens, including human OP-1 (hOP-1, Seq. ID Nos. 5 and 16–17), mouse OP-1 (mOP-1, Seq. ID Nos. 6 and 18–19), human and mouse OP-2 (Seq. ID Nos. 7, 8, and 20–b 23), CBMP2A (Seq. ID No. 9), CBMP2B (Seq. ID No. 10), BMP3 (Seq. ID No. 26), DPP (from Drosophila, Seq. ID No. 11), Vgl, (from Xenopus, Seq. ID No. 12), Vgr-1 (from mouse, Seq. ID No. 13), GDF-1 (from mouse, Seq. ID Nos. 14, 32 and 33), 60A protein (from Drosophila, Seq. ID Nos. 24 and 25), BMP5 (Seq. ID No. 27) and BMP6 (Seq. ID No. 28). The sequences are aligned essentially following the method of Needleman et al. (1970) *J. Mol. Biol.,* 48:443–453, calculated using the Align Program (DNAstar, Inc.) In the table, three dots indicates that the amino acid in that position is the same as the amino acid in hOP-1. Three dashes indicates that no amino acid is present in that position, and are included for purposes of illustrating homologies. For example, amino acid residue 60 of CBMP-2A and CBMP-2B is "missing". Of course, both these amino acid sequences in this region comprise Asn-Ser (residues 58, 59), with CBMP-2A then comprising Lys and Ile, whereas CBMP-2B comprises Ser and Ile.

TABLE II

| | Seq ID No: | | | | | | | | | | | | | | | |
|---|---|---|---|---|---|---|---|---|---|---|---|---|---|---|---|---|
| hOP-1 | 5 | Cys | Lys | Lys | His | Glu | Leu | Tyr | Val | Ser | Phe | Arg | Asp | Leu | Gly | Trp | Gln |
| mOP-1 | 6 | ... | ... | ... | ... | ... | ... | ... | ... | ... | ... | ... | ... | ... | ... | ... | ... |
| hOP-2 | 7 | ... | Arg | Arg | ... | ... | ... | ... | ... | ... | ... | Gln | ... | ... | ... | ... | Leu |
| mOP-2 | 8 | ... | Arg | Arg | ... | ... | ... | ... | ... | Ser | ... | ... | ... | ... | ... | ... | Leu |
| DPP | 11 | ... | Arg | Arg | ... | Ser | ... | ... | ... | Asp | ... | Ser | ... | Val | ... | ... | Asp |
| Vgl | 12 | ... | ... | Lys | Arg | His | ... | ... | ... | Glu | ... | Lys | ... | Val | ... | ... | ... |
| Vgr-1 | 13 | ... | ... | ... | ... | Gly | ... | ... | ... | ... | ... | Gln | ... | Val | ... | ... | ... |
| CBMP-2A | 9 | ... | ... | Arg | ... | Pro | ... | ... | ... | Asp | ... | Ser | ... | Val | ... | ... | Asn |
| CBMP-2B | 10 | ... | Arg | Arg | ... | Ser | ... | ... | ... | Asp | ... | Ser | ... | Val | ... | ... | Asn |
| BMP3 | 26 | ... | Ala | Arg | Arg | Tyr | ... | Lys | ... | Asp | ... | Ala | ... | Ile | ... | ... | Ser |
| GDF-1 | 14 | ... | Arg | Ala | Arg | Arg | ... | ... | ... | ... | ... | ... | Glu | Val | ... | ... | His |
| 50A | 25 | ... | Gln | Met | Glu | Thr | ... | ... | ... | Asp | ... | Lys | ... | ... | ... | ... | His |
| BMP5 | 27 | ... | ... | ... | ... | ... | ... | ... | ... | ... | ... | ... | ... | ... | ... | ... | ... |
| BMP6 | 28 | ... | Arg | ... | ... | ... | ... | ... | ... | ... | ... | Gln | ... | ... | ... | ... | ... |
| | | 1 | | | | 5 | | | | | 10 | | | | | 15 | |
| | Seq ID No: | | | | | | | | | | | | | | | |
| hOP-1 | 5 | Asp | Trp | Ile | Ile | Ala | Pro | Glu | Gly | Tyr | Ala | Ala | Tyr | Tyr | Cys | Glu | Gly |
| mOP-1 | 6 | ... | ... | ... | ... | ... | ... | ... | ... | ... | ... | ... | ... | ... | ... | ... | ... |
| hOP-2 | 7 | ... | ... | Val | ... | ... | ... | Gln | ... | ... | Ser | ... | ... | ... | ... | ... | ... |
| mOP-2 | 8 | ... | ... | Val | ... | ... | ... | Gln | ... | ... | Ser | ... | ... | ... | ... | ... | ... |
| DPP | 11 | ... | ... | ... | Val | ... | ... | Leu | ... | ... | Asp | ... | ... | ... | ... | His | ... |
| Vgl | 12 | Asn | ... | Val | ... | ... | ... | Gln | ... | ... | Met | ... | Asn | ... | ... | Tyr | ... |
| Vgr-1 | 13 | ... | ... | ... | ... | ... | ... | Lys | ... | ... | ... | ... | Asn | ... | ... | Asp | ... |
| CBMP-2A | 9 | ... | ... | ... | Val | ... | ... | Pro | ... | ... | His | ... | Phe | ... | ... | His | ... |
| CBMP-2B | 10 | ... | ... | ... | Val | ... | ... | Pro | ... | ... | Gln | ... | Phe | ... | ... | His | ... |
| BMP3 | 26 | Glu | ... | ... | ... | Ser | ... | Lys | Ser | Phe | Asp | ... | ... | ... | ... | Ser | ... |
| GDF-1 | 14 | Arg | ... | Val | ... | ... | ... | Arg | ... | Phe | Leu | ... | Asn | ... | ... | Gln | ... |
| 60A | 25 | ... | ... | ... | ... | ... | ... | ... | ... | ... | Gly | ... | Phe | ... | ... | Ser | ... |
| BMP5 | 27 | ... | ... | ... | ... | ... | ... | ... | ... | ... | ... | ... | Phe | ... | ... | Asp | ... |
| BMP6 | 28 | ... | ... | ... | ... | ... | ... | Lys | ... | ... | ... | ... | Asn | ... | ... | Asp | ... |
| | | | | | 20 | | | | | 25 | | | | | 30 | | |
| | Seq ID No: | | | | | | | | | | | | | | | |
| hOP-1 | 5 | Glu | Cys | Ala | Phe | Pro | Leu | Asn | Ser | Tyr | Met | Asn | Ala | Thr | Asn | His | Ala |
| mOP-1 | 6 | ... | ... | ... | ... | ... | ... | ... | ... | ... | ... | ... | ... | ... | ... | ... | ... |
| hOP-2 | 7 | ... | ... | Ser | ... | ... | ... | Asp | ... | Cys | ... | ... | ... | ... | ... | ... | ... |
| mOP-2 | 8 | ... | ... | ... | ... | ... | ... | Asp | ... | Cys | ... | ... | ... | ... | ... | ... | ... |
| DPP | 11 | Lys | ... | Pro | ... | ... | ... | Ala | Asp | His | Phe | ... | Ser | ... | ... | ... | ... |
| Vgl | 12 | ... | ... | Pro | Tyr | ... | ... | Thr | Glu | Ile | Leu | ... | Gly | Ser | ... | ... | ... |
| Vgr-1 | 13 | ... | ... | Ser | ... | ... | ... | ... | Ala | His | ... | ... | ... | ... | ... | ... | ... |
| CBMP-2A | 9 | Glu | ... | Pro | ... | ... | ... | Ala | Asp | His | Leu | ... | Ser | ... | ... | ... | ... |
| CBMP-2B | 10 | Asp | ... | Pro | ... | ... | ... | Ala | Asp | His | Leu | ... | Ser | ... | ... | ... | ... |
| BMP3 | 26 | Ala | ... | Gln | ... | ... | Met | Pro | Lys | Ser | Leu | Lys | Pro | Ser | ... | ... | ... |
| GDF-1 | 14 | Gln | ... | ... | Leu | ... | Val | Ala | Leu | Ser | Gly | Ser** | ... | Leu | ... | ... | ... |
| 60A | 25 | ... | ... | Asn | ... | ... | ... | ... | Ala | His | ... | ... | ... | ... | ... | ... | ... |
| BMP5 | 27 | ... | ... | Ser | ... | ... | ... | ... | Ala | His | Met | ... | ... | ... | ... | ... | ... |
| BMP6 | 28 | ... | ... | Ser | ... | ... | ... | ... | Ala | His | Met | ... | ... | ... | ... | ... | ... |
| | | | | 35 | | | | | 40 | | | | | 45 | | | |

TABLE II-continued

| | Seq ID No: | | | | | | | | | | | | | | | |
|---|---|---|---|---|---|---|---|---|---|---|---|---|---|---|---|---|
| hOP-1 | 5 | Ile | Val | Gln | Thr | Leu | Val | His | Phe | Ile | Asn | Pro | Glu | Thr | Val | Pro | Lys |
| mOP-1 | 6 | ... | ... | ... | ... | ... | ... | ... | ... | ... | ... | ... | Asp | ... | ... | ... | ... |
| hOP-2 | 7 | ... | Leu | ... | Ser | ... | ... | His | Leu | Met | Lys | ... | Asn | Ala | ... | ... | ... |
| mOP-2 | 8 | ... | Leu | ... | Ser | ... | ... | His | Leu | Met | Lys | ... | Asp | Val | ... | ... | ... |
| DPP | 11 | Val | ... | ... | ... | ... | ... | Asn | Asn | Asn | ... | ... | Gly | Lys | ... | ... | ... |
| Vgl | 12 | ... | Leu | ... | ... | ... | ... | ... | Ser | ... | Glu | ... | ... | Asp | Ile | ... | Leu |
| Vgr-1 | 13 | ... | ... | ... | ... | ... | ... | ... | Val | Met | ... | ... | ... | Tyr | ... | ... | ... |
| CBMP-2A | 9 | ... | ... | ... | ... | ... | ... | Asn | Ser | Val | ... | Ser | --- | Lys | Ile | ... | ... |
| CBMP-2B | 10 | ... | ... | ... | ... | ... | ... | Asn | Ser | Val | ... | Ser | --- | Ser | Ile | ... | ... |
| BMP3 | 26 | Thr | Ile | ... | Ser | Ile | ... | Arg | Ala** | Gly | Val | Val | Pro | Gly | Ile | ... | Glu |
| GDF-1 | 14 | Val | Leu | Arg | Ala | ... | Met | ... | Ala | Ala | Ala | ... | Gly | Ala | Ala | Asp | Leu |
| 60A | 25 | ... | ... | ... | ... | ... | ... | ... | Leu | Leu | Glu | ... | Lys | Lys | ... | ... | ... |
| BMP5 | 27 | ... | ... | ... | ... | ... | ... | ... | Leu | Met | Phe | ... | Asp | His | ... | ... | ... |
| BMP6 | 28 | ... | ... | ... | ... | ... | ... | ... | Leu | Met | ... | ... | ... | Tyr | ... | ... | ... |
| | | | 50 | | | | | 55 | | | | | 60 | | | |

| | Seq ID No: | | | | | | | | | | | | | | | |
|---|---|---|---|---|---|---|---|---|---|---|---|---|---|---|---|---|
| hOP-1 | 5 | Pro | Cys | Cys | Ala | Pro | Thr | Gln | Leu | Asn | Ala | Ile | Ser | Val | Leu | Tyr | Phe |
| mOP-1 | 6 | ... | ... | ... | ... | ... | ... | ... | ... | ... | ... | ... | ... | ... | ... | ... | ... |
| hOP-2 | 7 | Ala | ... | ... | ... | ... | ... | Lys | ... | Ser | ... | Thr | ... | ... | ... | ... | Tyr |
| mOP-2 | 8 | Ala | ... | ... | ... | ... | ... | Lys | ... | Ser | ... | Thr | ... | ... | ... | ... | Tyr |
| DPP | 11 | Ala | ... | ... | Val | ... | ... | ... | ... | Asp | Ser | Val | Ala | Met | ... | ... | Leu |
| Vgl | 12 | ... | ... | ... | Val | ... | ... | Lys | Met | Ser | Pro | ... | ... | Met | ... | Phe | Tyr |
| Vgr-1 | 13 | ... | ... | ... | ... | ... | ... | Lys | Val | ... | ... | ... | ... | ... | ... | ... | ... |
| CBMP-2A | 9 | Ala | ... | ... | Val | ... | ... | Glu | ... | Ser | ... | ... | ... | Met | ... | ... | Leu |
| CBMP-2B | 10 | Ala | ... | ... | Val | ... | ... | Glu | ... | Ser | ... | ... | ... | Met | ... | ... | Leu |
| BMP3 | 26 | ... | ... | ... | Val | ... | Glu | Lys | Met | Ser | Ser | Leu | ... | Ile | ... | Phe | Tyr |
| GDF-1 | 14 | ... | ... | ... | Val | ... | Ala | Arg | ... | Ser | Pro | ... | ... | ... | ... | Phe | ... |
| 60A | 25 | ... | ... | ... | ... | ... | ... | Arg | ... | Gly | ... | Leu | Pro | ... | ... | ... | His |
| BMP5 | 27 | ... | ... | ... | ... | ... | ... | Lys | ... | ... | ... | ... | ... | ... | ... | ... | ... |
| BMP6 | 28 | ... | ... | ... | ... | ... | ... | Lys | ... | ... | ... | ... | ... | ... | ... | ... | ... |
| | | 65 | | | | | | 70 | | | | | 75 | | | | 80 |

| | Seq ID No: | | | | | | | | | | | | | | | |
|---|---|---|---|---|---|---|---|---|---|---|---|---|---|---|---|---|
| hOP-1 | 5 | Asp | Asp | Ser | Ser | Asn | Val | Ile | Leu | Lys | Lys | Tyr | Arg | Asn | Met | Val | Val |
| mOP-1 | 6 | ... | ... | ... | ... | ... | ... | ... | ... | ... | ... | ... | ... | ... | ... | ... | ... |
| hOP-2 | 7 | ... | Ser | ... | Asn | ... | ... | ... | ... | Arg | ... | His | ... | ... | ... | ... | ... |
| mOP-2 | 8 | ... | Ser | ... | Asn | ... | ... | ... | ... | Arg | ... | His | ... | ... | ... | ... | ... |
| DPP | 11 | Asn | ... | Gln | ... | Thr | ... | Val | ... | ... | Asn | ... | Gln | Glu | ... | Thr | ... |
| Vgl | 12 | ... | Asn | Asn | Asp | ... | ... | Val | ... | Arg | His | ... | Glu | ... | ... | Ala | ... |
| Vgr-1 | 13 | ... | ... | Asn | ... | ... | ... | ... | ... | ... | ... | ... | ... | ... | ... | ... | ... |
| CBMP-2A | 9 | ... | Glu | Asn | Glu | Lys | ... | Val | ... | ... | Asn | ... | Gln | Asp | ... | ... | ... |
| CBMP-2B | 10 | ... | Glu | Tyr | Asp | Lys | ... | Val | ... | ... | Asn | ... | Gln | Glu | ... | ... | ... |
| BMP3 | 26 | ... | Glu | Asn | Lys | ... | ... | Val | ... | ... | Val | ... | Pro | ... | ... | Thr | ... |
| GDF-1 | 14 | ... | Asn | ... | Asp | ... | ... | Val | ... | Arg | Gln | ... | Glu | Asp | ... | ... | ... |
| 60A | 25 | Leu | Asn | Asp | Glu | ... | ... | Asn | ... | ... | ... | ... | ... | ... | ... | Ile | ... |
| BMP5 | 27 | ... | ... | ... | ... | ... | ... | ... | ... | ... | ... | ... | ... | ... | ... | ... | ... |
| BMP6 | 28 | ... | ... | Asn | ... | ... | ... | ... | ... | ... | ... | ... | ... | Trp | ... | ... | ... |
| | | | | | 85 | | | | | 90 | | | | 95 | | | |

| | Seq ID No: | | | | | |
|---|---|---|---|---|---|---|
| hOP-1 | 5 | Arg | Ala | Cys | Gly | Cys | His |
| mOP-1 | 6 | ... | ... | ... | ... | ... | ... |
| hOP-2 | 7 | Lys | ... | ... | ... | ... | ... |
| mOP-2 | 8 | Lys | ... | ... | ... | ... | ... |
| DPP | 11 | Val | Gly | ... | ... | ... | Arg |
| Vgl | 12 | Asp | Glu | ... | ... | ... | Arg |
| Vgr-1 | 13 | ... | ... | ... | ... | ... | ... |
| CBMP-2A | 9 | Glu | Gly | ... | ... | ... | Arg |
| CBMP-2B | 10 | Glu | Gly | ... | ... | ... | Arg |
| BMP3 | 26 | Glu | Ser | ... | Ala | ... | Arg |
| GDF-1 | 14 | Asp | Glu | ... | ... | ... | Arg |
| 60A | 25 | Lys | Ser | ... | ... | ... | ... |
| BMP5 | 27 | ... | Ser | ... | ... | ... | ... |
| BMP6 | 28 | ... | ... | ... | ... | ... | ... |
| | | | | | 100 | | 102 |

**Between residues 56 and 57 of BMP3 (Seq. ID No. 26) is a Val residue; between residues 43 and 44 of GDF-1 (Seq. ID No. 14) lies the amino acid sequence Gly—Gly—Pro—Pro.

As is apparent from the foregoing amino acid sequence comparisons, significant amino acid changes can be made within the generic sequences while retaining the morphogenic activity. For example, while the GDF-1 protein sequence depicted in Table II shares only about 50% amino acid identity with the hoP1 sequence described therein, the GDF-1 sequence shares greater than 70% amino acid sequence homology (or "similarity") with the hOP1 sequence, where "homology" or "similarity" includes allowed conservative amino acid changes within the sequence as defined by Dayoff, et al., *Atlas of Protein Sequence and Structure* vol.5, supp.3, pp.345–362, (M. O. Dayoff, ed., Nat'l BioMed. Res. Fd'n, Washington D.C. 1979.)

As is apparent from the foregoing amino acid sequence comparisons, significant amino acid changes can be made within the generic sequences while retaining the morphogenic activity. For example, while the GDF-1 protein sequence (Seq ID No. 14) depicted in Table II shares only about 50% amino acid identity with the hOP1 sequence (Seq. ID No. 5) described therein, the GDF-1 sequence shares greater than 70% amino acid sequence homology (or "similarity") with the hOP1 sequence, where "homology" or "similarity" includes allowed conservative amino acid changes within the sequence as defined by Dayoff, et al., *Atlas of Protein Sequence and Structure* vol.5, supp.3, pp.345–362, (M. O. Dayoff, ed., Nat'l BioMed. Res. Fd'n, Washington D.C. 1979.)

The currently most preferred protein sequences useful as morphogens in this invention include those having greater than 60% identity, preferably greater than 65% identity, with the amino acid sequence defining the conserved six cysteine skeleton of hOP1 (e.g., residues 43–139 of Seq. ID No. 5). These most preferred sequences include both allelic and species variants of the OP-1 and OP-2 proteins (Seq. ID Nos. 5–8), including the Drosophila 60A protein (e.g. Seq. ID No. 25). Accordingly, in still another preferred aspect, the invention includes morphogens comprising species of polypeptide chains having the generic amino acid sequence referred to herein as "OPX" (Seq. ID No. 29), which defines the seven cysteine skeleton and accommodates the identities between the various identified mouse and human OP1 and OP2 proteins (Seq. ID Nos. 5–8). Each Xaa at a given position in OPX (Seq. ID No. 28) independently is selected from the residues occurring at the corresponding position in the C-terminal sequence of mouse or human OP1 or OP2 (see Seq. ID Nos. 5–8 and/or Seq. ID Nos. 16–23).

II. Matrix Considerations

The morphogens of this invention may be implanted surgically, dispersed in a biocompatible, preferably in vivo biodegradable matrix appropriately modified to provide a structure in which the morphogen may be dispersed and which allows the influx, differentiation and proliferation of migrating progenitor cells. Alternatively, or, in addition, differentiated hepatocytes and/or hepatocytic progenitor cells, stimulated by exposure to the morphogen, may be disposed in and attached to a matrix structure and implanted surgically. In certain applications, such as where tissue morphogenesis is to be induced in the absence of endogenous tissue-specificity directing signals, the matrix preferably also provides signals capable of directing the tissue specificity of the differentiating cells, and provides a morphogenically permissive environment, being essentially free of growth inhibiting signals.

Where the matrix is to be incorporated into a surgically prepared liver, or provided to a biocompatible, associated site, the formulated matrix on which the morphogen is disposed may be shaped as desired in anticipation of surgery or may be shaped by the physician or technician during surgery. Where cells are to be attached to the matrix before implantation, the matrix preferably is shaped before cells are attached thereto. The matrix preferably is biodegradable in vivo, being slowly absorbed by the body and replaced by new tissue growth, in the shape or very nearly in the shape of the implant.

Details of how to make and how to use preferred matrices useful in this invention are disclosed below. In addition to these matrices, WO 88/03785, published Jun. 2, 1988, and WO90/12604, published Nov. 1, 1990, describe additional polymeric materials and matrix scaffold considerations. The disclosures of these publications are incorporated herein by reference.

A. Tissue-Derived Matrices

Suitable biocompatible, in vivo biodegradable acellular matrices may be prepared from naturally-occurring tissue. The tissue is treated with suitable agents to substantially extract the cellular, nonstructural components of the tissue. The agents also should be capable of extracting any growth inhibiting components associated with the tissue. The resulting material is a porous, acellular matrix, substantially depleted in nonstructurally-associated components, and preferably containing structural molecules such as collagen, laminin, hyaluronic acid, and the like.

The matrix also may be further treated with agents that modify the matrix, increasing the number of pores and micropits on its surfaces. Those skilled in the art will know how to determine which agents are best suited to the extraction of nonstructural components for different tissues. For example, soft tissues such as liver and lung may be thin-sectioned and exposed to a nonpolar solvent such as, for example, 100% ethanol, to destroy the cellular structure of the tissue and extract nonstructural components. The material then is dried and pulverized to yield nonadherent porous particles. Structural tissues such as cartilage and dentin where collagen is the primary component may be demineralized and extracted with guanidine, essentially following the method of Sampath et al. (1983) PNAS 80:6591–6595. For example, pulverized and demineralized dentin is extracted with five volumes of 4M guanidine-HCl, 50 mM Tris-HCl, pH 7.0 for 16 hours at 4° C. The suspension then is filtered. The insoluble material that remains is collected and used to fabricate the matrix. The material is mostly collagenous in manner. It is devoid of morphogenic activity. The matrix particles may further be treated with a collagen fibril-modifying agent that extracts potentially unwanted components from the matrix, and alters the surface structure of the matrix material. Useful agents include acids, organic solvents or heated aqueous media. A detailed description of these matrix treatments are disclosed in U.S. Pat. No. 4,975,526 and PCT publication US90/00912, published Sep. 7, 1990 (WO90/10018).

The currently most preferred agent is a heated aqueous fibril-modifying medium such as water, to increase the matrix particle surface area and porosity. The currently most preferred aqueous medium is an acidic aqueous medium having a pH of less than about 4.5, e.g., within the range of about pH 2–pH 4 which may help to "swell" the collagen before heating. 0.1% acetic acid, which has a pH of about 3, currently is most preferred. 0.1 M acetic acid also may be used.

Various amounts of delipidated, demineralized guanidine-extracted collagen matrix are heated in the aqueous medium (1 g matrix/30 ml aqueous medium) under constant stirring in a water jacketed glass flask, and maintained at a given temperature for a predetermined period of time. Preferred treatment times are about one hour, although exposure times of between about 0.5 to two hours appear acceptable. The temperature employed is held constant at a temperature within the range of about 37° C. to 65° C. The currently preferred heat treatment temperature is within the range of about 45° C to 60° C.

After the heat treatment, the matrix is filtered, washed, lyophilized and used for implant. Where an acidic aqueous medium is used, the matrix also is preferably neutralized prior to washing and lyophilization. A currently preferred neutralization buffer is a 200 mM sodium phosphate buffer, pH 7.0. To neutralize the matrix, the matrix preferably first is allowed to cool following thermal treatment, the acidic aqueous medium (e.g., 0.1% acetic acid) then is removed and replaced with the neutralization buffer and the matrix agitated for about 30 minutes. The neutralization buffer then may be removed and the matrix washed and lyophilized.

Other useful fibril-modifying treatments include acid treatments (e.g., trifluoroacetic acid and hydrogen fluoride) and solvent treatments such as dichloromethane, acetonitrile, isopropanol and chloroform, as well as particular acid/solvent combinations.

After contact with the fibril-modifying agent, the treated matrix may be washed to remove any extracted components, following a form of the procedure set forth below:

1. Suspend matrix preparation in TBS (Tris-buffered saline) 1 g/200 ml and stir at 4° C. for 2 hrs; or in 6 M urea, 50 mM Tris-HCl, 500 mM NaCl, pH 7.0 (UTBS) or water and stir at room temperature (RT) for 30 minutes (sufficient time to neutralize the pH);
2. Centrifuge and repeat wash step; and
3. Centrifuge; discard supernatant; water wash residue; and then lyophilize.

B. Synthetic Matrices

Suitable matrix scaffolds may be created from biocompatible, preferably in vivo biodegradable synthetic polymers, including polylactic acid, polyglycolic acid, polyanhydride, polybutyric acid, and copolymers thereof, and/or synthetic-inorganic materials, such as hydroxyapatite, tricalcium phosphate, and other calcium phospates. These polymers are well described in the art and are available commercially. For example, polymers composed of polyactic acid (e.g., MW 100 kDa), 80% polylactide/20% glycoside or poly 3-hydroxybutyric acid (e.g., MW 30 kDa) all may be purchased from PolySciences, Inc. The polymer compositions generally are obtained in particulate form and the osteogenic devices preferably fabricated under nonaqueous conditions (e.g., in an ethanol-trifluoroacetic acid solution, EtOH/TFA) to avoid hydrolysis of the polymers. In addition, one can alter the morphology of the particulate polymer compositions, for example to increase porosity, using any of a number of particular solvent treatments known in the art.

For example, osteogenic devices fabricated with morphogenic protein, solubilized in EtOH/TFA as described below, and a matrix composed of polylactic acid, poly 3-hydroxybutyric acid, or 80% polylactide/20% glycoside are all osteogenically active when implanted in the rat model and bioassayed as described in U.S. Pat. No. 4,968,590 (e.g., as determined by calcium content, alkaline phosphatase levels and histology of 12-day implants).

C. Synthetic Tissue-Specific Matrices

In addition to the naturally-derived tissue-specific matrices described above, useful tissue-specific matrices may be formulated synthetically if appropriately modified. These porous biocompatible, in vivo biodegradable synthetic matrices are disclosed in PCT publication US91/03603, published Dec. 12, 1991 (WO91/18558), the disclosure of which is hereby incorporated by reference. Briefly, the matrix comprises a porous crosslinked structural polymer of biocompatible, biodegradable collagen and appropriate, tissue-specific glycosaminoglycans as tissue-specific cell attachment factors. Collagen derived from a number of sources may be suitable for use in these synthetic matrices, including insoluble collagen, acid-soluble collagen, collagen soluble in neutral or basic aqueous solutions, as well as those collagens which are commercially available.

Glycosaminoglycans (GAGs) or mucopolysaccharides are hexosamine-containing polysaccharides of animal origin that have a tissue specific distribution, and therefore may be used to help determine the tissue specificity of the morphogen-stimulated differentiating cells. Reaction with the GAGs also provides collagen with another valuable property, i.e., inability to provoke an immune reaction (foreign body reaction) from an animal host.

Chemically, GAGs are made up of residues of hexoseamines glycosidically bound and alternating in a more-or-less regular manner with either hexouronic acid or hexose moieties (see, e.g., Dodgson et al. in *Carbohydrate Metabolism and its Disorders* (Dickens et al., eds.) Vol. 1, Academic Press (1968)). Useful GAGs include hyaluronic acid, heparin, heparin sulfate, chondroitin 6-sulfate, chondroitin 4-sulfate, dermatan sulfate, and keratin sulfate. Other GAGs are suitable for forming the matrix described herein, and those skilled in the art will either know or be able to ascertain other suitable GAGs using no more than routine experimentation. For a more detailed description of mucopolysaccharides, see Aspinall, *Polysaccharides,* Pergamon Press, Oxford (1970). For example, as disclosed in U.S. application Ser. No. 529,852, chondroitin-6-sulfate can be used where endochondral bone formation is desired. Heparin sulfate, on the other hand, may be used to formulate synthetic matrices for use in lung tissue repair.

Collagen can be reacted with a GAG in aqueous acidic solutions, preferably in diluted acetic acid solutions. By adding the GAG dropwise into the aqueous collagen dispersion, coprecipitates of tangled collagen fibrils coated with GAG results. This tangled mass of fibers then can be homogenized to form a homogeneous dispersion of fine fibers and then filtered and dried.

Insolubility of the collagen-GAG products can be raised to the desired degree by covalently cross-linking these materials, which also serves to raise the resistance to resorption of these materials. In general, any covalent cross-linking method suitable for cross-linking collagen also is suitable for cross-linking these composite materials, although crosslinking by a dehydrothermal process is preferred.

When dry, the crosslinked particles are essentially spherical, with diameters of about 500 $\mu$m. Scanning electron miscroscopy shows pores of about 20 $\mu$m on the surface and 40 $\mu$m on the interior. The interior is made up of both fibrous and sheet-like structures, providing surfaces for cell attachment. The voids interconnect, providing access to the cells throughout the interior of the particle. The material appears to be roughly 99.5% void volume, making the material very efficient in terms of the potential cell mass that can be grown per gram of microcarrier.

D. Morphogen Adsorption to Matrix Surfaces

The morphogens described herein can be combined and dispersed in a suitable matrix using any of the methods described below:

1. Ethanol Precipitation

Matrix is added to the morphogen dissolved in guanidine-HCl. Samples are vortexed and incubated at a low temperature. Samples are then further vortexed. Cold absolute ethanol is added to the mixture which is then stirred and incubated. After centrifugation (microfuge, high speed) the supernatant is discarded. The matrix is washed with cold concentrated ethanol in water and then lyophilized.

2. Acetonitrile Trifluoroacetic Acid Lyophilization

In this procedure, morphogen in an acetonitrile trifluoroacetic acid (ACN/TFA solution is added to the carrier material. Samples are vigorously vortexed many times and then lyophilized.

3. Buffered Saline Lyophilization

Morphogen preparations in physiological saline may also be vortexed with the matrix and lyophilized to produce morphogenically active material.

III. Hepatocytic Cell Considerations

Primary hepatocytes or progenitor cells may be implanted in the mammal in one embodiment of the invention. For example, implanted hepatocytes may act as gene therapy tools capable of correcting a protein deficiency in vivo by expressing and/or secreting the deficient protein when implanted at a liver tissue or associated locus in a mammal. The liver functions in part as a protein-synthesizing organ, responsible for the production of myriad proteins which are secreted from the liver and transported, e.g., via the circulatory system, to function elsewhere in the body. Accordingly, hepatic tissue, like renal and pancreatic tissue, provides an endogenous system having the necessary mechanisms in place to act as a vector for the in vivo production of (including secretion of) any protein, including proteins not normally expressed by hepatic tissue. Thus, protein deficiencies that can be treated by this method include proteins involved in normal liver functions, proteins normally produced and secreted by the liver to function elsewhere in the body, and proteins not normally produced by hepatic tissue. Where the proteins to be produced are not normally expressed by hepatic tissue, the hepatocytes must be provided with means for expressing that protein. For example, the cell may be genetically engineered as described below to induce expression of the endogenous genetic sequence encoding the protein. Alternatively, a nucleic acid encoding the protein and under control of a suitable promoter (and enhancer), may be provided to the cell as described below. In addition, the cell may be provided with one or more regulatory elements so that expression of the protein of interest mimics that of the endogenously produced protein, particularly where normal protein expression depends on changes in the physiological concentration of a molecule. For example, insulin production is regulated by blood glucose levels in the body.

The protein deficiency to be corrected may result from defective endogenous protein production, including protein expression and/or secretion, or the protein's efficacy may be reduced due to a preexisting condition in the individual. The defect may be genetic or may be induced by, for example, damage to the protein-synthesizing tissue. Exemplary hepatic proteins that may be used in a gene therapy include, but are not limited to, albumin and albumin synthesis proteins, blood clotting factors, including fibrinogen and thrombin, Factor VIII, iron or copper binding proteins, and vitamin A binding proteins. Exemplary non-hepatic proteins that may be used in a gene therapy include, but are not limited to, insulin, tissue plasminogen activator (TPA), erythropoietin, growth hormones, and the like. Similarly, the cells also may act as in vivo drug delivery vehicles, capable of producing and secreting one or more therapeutic drugs when implanted at a suitable locus in a mammal. The cells further may be manipulated to modify antigen expression on the cell surface, and limit the in vivo immune response typically induced by foreign material.

Where cells act as gene therapy tools, the cells may be obtained from a donor competent for providing the protein of interest. Cells can be obtained by biopsy or surgical excision from a donor, or from established cell lines. Preferably, allogenic cells are obtained from a biocompatible donor. Alternatively, autologous cells may be obtained from the patient and modified by recombinant DNA technology to incorporate genetic sequences sufficient to allow the cells to produce the protein or proteins of interest in vivo when the cells are reimplanted in the patient. Protocols and detailed discussions of considerations for introducing foreign genetic material into cells, particularly human cells, are well described in the art. A representative, but by no means exhaustive list, includes U.S. Pat.No. 4,868,116, issued Sep. 19, 1989, U.S. Pat. No. 4,980,286, issued Dec. 25, 1990, both to Morgan et al., and U.S. Pat. No. 4,396,601, issued Aug. 2, 1983, to Salser et al., Anderson, WF (1992) *Science* 256:808–813, Karson et al., (1992) *J. Reprod Med* 37:508–514, and Hoeg et al., (1990) *Trans Assoc. Am Physicians* 103:73–79, these disclosures of which are incorporated herein by reference.

A currently preferred protocol for isolating primary hepatocytes from liver tissue is described in Example 3 below. Other methods known in the art also are envisioned to be useful, such as those described, for example, in WO 88/03785. Where pluripotential hemopoietic stem cells are to be used, a useful method for their isolation is described in commonly owned, now-abandoned U.S. Ser. No. 752,764. Briefly, and as described in detail therein, a biocompatible matrix material able to allow the influx of migratory progenitor cells may be implanted at an in vivo site long enough to allow the influx of migratory progenitor cells. For example, a bone-derived, guanidine-extracted matrix, formulated as disclosed for example in Sampath et al. ((1983) *PNAS* 80:6591–6595), or U.S. Pat. No. 4,975,526, may be implanted into a rat, essentially following the method of Sampath et al. (ibid). After three days the implant is removed, and the progenitor cells associated with the matrix dispersed and cultured. Another method is described, for example, in U.S. Pat. No. 5,061,620, issued Oct. 29, 1991, to Tsukamoto et al.

Isolated cells may be stimulated in vitro by morphogen exposure, essentially as described in Example 3. Stimulation is performed under sterile conditions, using an appropriate morphogen concentration and incubation period to stimulate the cells. Preferred times and concentration for a given procedure may be determined empirically by the clinician without undue experimentation. In general, a period of from about 10 minutes to 72 hours should be sufficient. Cells may be attached to a matrix by incubating the cells in the presence of matrix for at least a number of hours, e.g., 3–5 hours, or, preferably overnight. An efficient technique for attaching cells to a matrix surface is to place a concentrated suspension of cells on the surface of the matrix material and allow the cells to infiltrate and adsorb to the material. Cells typically attach individually or in small groups. In the absence of added morphogen cells begin rearranging into clusters within 24 hours and within 3 days cells have almost completely infiltrated the support and have organized into large clusters.

In a particularly preferred embodiment, the morphogen first is adsorbed to the matrix surface and cells subsequently attached thereto. The cell-matrix structure may be maintained in vitro and to allow the cells to proliferate (preferably by exposure to a morphogen or morphogen-stimulting agent) or, alternatively, the complex may be implanted in the animal and the cells allowed to proliferate (and differentiate) in vivo.

As with morphogen administrations, where implanted cells are to replace damaged or lost tissue at a liver-specific locus, the cells preferably are provided to a surgically prepared locus where from which necrotic or cirrhotic tissue has been removed, e.g., by surgical, chemical, ablating, or other means known in the medical art. The cells then are provided to the prepared site, preferably attached to a matrix and associated with a morphogen or morphogen-stimulating agent.

The cells may be provided to a morphogenically permissive site in a liver-specific locus, e.g., following removal of necrotic and/or cirrhotic tissue, or following excision of sufficient tissue to provide a morphogenically permissive site. Alternatively, the cell-matrix structure may be implanted together with a morphogen or morphogen-stimulating agent at a suitable, vascularized liver-associated locus, such as within the folds of the mesentery.

As described above, implanting cells together with a morphogen or morphogen-stimulating agent enhances their proliferation and their viability in vivo, such that the new tissue is formed without the significant associated cell loss or delay which characterizes existing protocols and which currently require the use of substantial initial seed cell populations. In addition, hepatic tissue growth can be stimulated using the methods described herein without the need of a partial hepatectomy as described in the art. Finally, the morphogens described herein functionally inhibit the tissue damage associated with the body's immune response, reducing the need for associated treatments with immunosuppressive drugs.

IV. Bioassy Considerations

The following sets forth various procedures for evaluating the in vivo morphogenic utility of the morphogens and morphogenic compositions of this invention. The proteins and compositions may be injected or surgically implanted in a mammal, following any of a number of procedures well known in the art.

Histological Evaluation

Histological sectioning and staining is preferred to determine the extent of morphogenesis in vivo, particularly in tissue repair procedures. Excised implants are fixed in Bouins Solution, embedded in paraffin, and cut into 6–8 $\mu$m sections. Staining with toluidine blue or hemotoxylin/eosin demonstrates clearly the ultimate development of the new tissue. Twelve day implants are usually sufficient to determine whether the implants contain newly induced tissue.

Successful implants exhibit a controlled progression through the stages of induced tissue development allowing one to identify and follow the tissue-specific events that occur. For example, in endochondral bone formation the stages include: (1) leukocytes on day one; (2) mesenchymal cell migration and proliferation on days two and three; (3) chondrocyte appearance on days five and six; (4) cartilage matrix formation on day seven; (5) cartilage calcification on day eight; (6) vascular invasion, appearance of osteoblasts, and formation of new bone on days nine and ten; (7) appearance of osteoclasts and bone remodeling and dissolution of the implanted matrix on days twelve to eighteen; and (8) hematopoietic bone marrow differentiation in the ossicle on day twenty-one. Similarly, in hepatic tissue formation the stages include leukocytes on day one, mesenchymal cell migration and proliferation on days two and three, hepatocyte appearance on days five and six, followed by matrix formation and vascularization.

Biological Markers

In addition to histological evaluation, biological markers may be used as a marker for tissue morphogenesis. Useful markers include tissue-specific enzymes whose activities may be assayed (e.g., spectrophotometrically) after homogenization of the implant. These assays may be useful for quantitation and for obtaining an estimate of tissue formation quickly after the implants are removed from the animal. For example, alkaline phosphatase activity may be used as a marker for osteogenesis.

Incorporation of systemically provided morphogens may be followed using tagged morphogens (e.g., radioactively labelled) and determining their localization in new tissue, and/or by monitoring their disappearance from the circulatory system using a standard pulse-chase labeling protocol. The morphogen also may be provided with a tissue-specific molecular tag, whose uptake may be monitored and correlated with the concentration of morphogen provided.

V. Formulations and Methods for Parenteral Administration of Therapeutic Agents

The morphogens of this invention may be used to repair diseased or damaged mammalian tissue. The tissue to be repaired is preferably assessed, and excess necrotic or interfering scar tissue removed as needed, by surgical, chemical, ablating or other methods known in the medical arts.

The morphogen then may be provided directly to the tissue locus as part of a sterile, biocompatible composition, either by surgical implantation or injection. Alternatively, a sterile, biocompatible composition containing morphogen-stimulated progenitor cells may be provided to the tissue locus. The existing tissue at the locus, whether diseased or damaged, provides the appropriate matrix to allow the proliferation and tissue-specific differentiation of progenitor cells. In addition, a damaged or diseased tissue locus, particularly one that has been further assaulted by surgical means, provides a morphogenically permissive environment. For some tissues, it is envisioned that systemic provision of the morphogen will be sufficient.

In some circumstances, particularly where tissue damage is extensive, the tissue may not be capable of providing a sufficient matrix for cell influx and proliferation. In these instances, it may be necessary to provide the morphogen or morphogen-stimulated progenitor cells to the tissue locus in association with a suitable, biocompatible formulated matrix, prepared by any of the means described below. The matrix preferably is tissue-specific, in vivo biodegradable, and comprises particles having dimensions within the range of 70–850 $\mu$m, most preferably 150–420 $\mu$m.

The morphogens may be provided to an individual by any suitable means. Preferably, the morphogen or morphogen-stimulating agent (collectively described herein below as the "therapeutic agent") is provided directly to the liver tissue (e.g., locally, as by injection to the tissue locus or by periodic release from a locally implanted osmotic pump). While not currently preferred for most liver tissue regenerative applications, oral administration or systemic injection also may be viable administration routes for certain applications, such as part of a protocol to enhance viabilty of a tissue to be transplanted, or as part of a protocol to maintain liver function during a surgical or other therapeutic procedure, or for maintaining liver function in aged or immunosuppressed individuals, or others at risk for hepatic tissue damage. A detailed description of considerations for systemic administration, including oral and parenteral administration, is disclosed, for example, in commonly owned, now-abandoned U.S. Ser. No. 07/938,336, incorporated hereinabove by reference. It should be noted that morphogenically active protein is present in milk, including mammary gland extract, colostrum and 57-day milk, and also is present in human serum, indicating that systemic and, in particular, oral administration are viable administrative routes for morphogens.

Where the morphogen or morphogen-stimulatig agent is provided by local injection, the morphogen preferably comprises part of an aqueous solution. The solution is physiologically acceptable so that in addition to delivery of the desired morphogen to the patient, the solution does not otherwise adversely affect the patient's electrolyte and volume balance. The aqueous medium for the morphogen thus may comprise normal physiologic saline (0.85–0.9% NaCl, 0.15M), pH 7–7.4. The aqueous solution containing the morphogen can be made, for example, by dissolving the protein in 50% ethanol containing acetonitrile in 0.1% trifluoroacetic acid (TFA) or 0.1% HCl, or equivalent solvents. One volume of the resultant solution then is added, for example, to ten volumes of phosphate buffered saline (PBS), which further may include 0.1–0.2% human serum albumin (HSA). The resultant solution preferably is vortexed extensively. If desired, a given morphogen may be made more soluble by association with a suitable molecule. For example, the pro form of the morphogenic protein comprises a species that is soluble in physiologically buffered solutions. In fact, the endogenous protein is thought to be transported in this form. This soluble form of the protein may be obtained from the culture medium of morphogen-secreting mammalian cells. Alternatively, a soluble species may be formulated by complexing the mature dimer (or an active fragment thereof) with part or all of a pro domain. Another molecule capable of enhancing solubility and particularly useful for oral administrations, is casein. For example, addition of 0.2% casein increases solubility of the mature active form of OP-1 by 80%. Other components found in milk and/or various serum proteins also may be useful.

Useful solutions for parenteral administration may be prepared by any of the methods well known in the pharmaceutical art, described, for example, in *Remington's Pharmaceutical Sciences* (Gennaro, A., ed.), Mack Pub., 1990. Formulations may include, for example, polyalkylene glycols such as polyethylene glycol, oils of vegetable origin, hydrogenated naphthalenes, and the like. Formulations for direct administration, in particular, may include glycerol and other compositions of high viscosity. Biocompatible, preferably bioresorbable, polymers, including, for example, hyaluronic acid, collagen, polybutyrate, tricalcium phosphate, lactide and lactide/glycolide copolymers, may be useful excipients to control the release of the morphogen in vivo. Other potentially useful parenteral delivery systems for these morphogens include ethylene-vinyl acetate copolymer particles, osmotic pumps, implantable infusion systems, and liposomes.

In addition, while the mature forms of certain morphogens described herein typically are sparingly soluble, the morphogen form found in milk (and mammary gland extract and colostrum) is readily soluble, probably by noncovalent association of the mature, morphogenically active form with part or all of the pro domain of the intact sequence and/or by association with one or more milk components. Accordingly, the compounds provided herein also may be associated with molecules capable of enhancing their solubility in vitro or in vivo.

The compounds provided herein also may be associated with molecules capable of targeting the morphogen or morphogen-stimulating agent to liver tissue. For example, an antibody, antibody fragment, or other binding protein that interacts specifically with a surface molecule on liver tissue cells, including hepatocytes or epithelial cells, may be used. Useful targeting molecules may be designed, for example, using the single chain binding site technology disclosed, for example, in U.S. Pat. No. 5,091,513.

As described above, the morphogens provided herein share significant sequence homology in the C-terminal active domains. By contrast, the sequences typically diverge significantly in the sequences which define the pro domain. Accordingly, the pro domain is thought to be morphogen-specific. As described above, it is also known that the various morphogens identified to date are differentially expressed in the different tissues. Accordingly, without being limited to any given theory, it is likely that, under natural conditions in the body, selected morphogens typically act on a given tissue. Accordingly, part or all of the pro domains which have been identified associated with the active form of the morphogen in solution, may serve as targeting molecules for the morphogens described herein. For example, the pro domains may interact specifically with one or more molecules at the target tissue to direct the morphogen associated with the pro domain to that tissue. Accordingly, another useful targeting molecule for targeting morphogen to hepatic tissue may include part or all of a morphogen pro domain. As described above, morphogen species comprising the pro domain may be obtained from culture medium of morphogen-secreting cells. Alternatively, a tissue-targeting species may be formulated by complexing the mature dimer (or an active fragment thereof) with part or all of a pro domain.

Finally, the morphogens or morphogen-stimulating agents provided herein may be administered alone or in combination with other molecules ("cofactors") known to be beneficial in maintaining liver function, particularly symptom-alleviating cofactors, such as other, non-steroidal anti-inflammatory agents, antiseptics and antibiotics.

The compounds provided herein can be formulated into pharmaceutical compositions by admixture with pharmaceutically acceptable nontoxic excipients and carriers. As noted above, such compositions may be prepared for direct, or local or systemic administration, particularly in the form of liquid solutions or suspensions; for oral administration, particularly in the form of tablets or capsules; or intranasally, particularly in the form of powders, nasal drops, or aerosols.

The compositions can be formulated for administration to humans or other mammals in therapeutically effective amounts, e.g., amounts which provide appropriate concentrations for a time sufficient to substantially eliminate or reduce the patient's pathological condition, including stimulating regeneration of damaged or lost hepatic tissue following hepatocellular injury including inhibiting additional damage thereto, to provide therapy for the liver diseases and disorders described above, and amounts effective to protect hepatic tissue in anticipation of injury to the tissue.

As will be appreciated by those skilled in the art, the concentration of the compounds described in a therapeutic composition will vary depending upon a number of factors, including the dosage of the drug to be administered, the chemical characteristics (e.g., hydrophobicity) of the compounds employed, and the route of administration. The preferred dosage of therapeutic agent to be administered also is likely to depend on such variables as the type and extent of progression of the hepatic disorder, the overall health status of the particular patient, the relative biological efficacy of the compound selected, the formulation of the compound excipients, and its route of administration. In general terms, the compounds of this invention may be provided in an aqueous physiological buffer solution containing about 0.001 to 10% w/v compound for liquid administration. Typical dose ranges are from about 10 ng/kg to about 1 g/kg of body weight per day; a preferred dose range is from about 0.1 µg/kg to 100 mg/kg of body weight per day. Optimally, the morphogen dosage given is between 0.1–100 μg of protein per kilogram weight of the patient. No obvious morphogen induced pathological lesions are induced when mature morphogen (e.g., OP-1 e.g., (Seq. ID No. 5 or 6, 20 μg) is administered daily to normal growing rats for 21 consecutive days. Moreover, 10 μg systemic injections of morphogen (e.g., OP-1; Seq. ID No 5 or 6) injected daily for 10 days into normal newborn mice does not produce any gross abnormalties.

Where morphogens are administered systemically, in the methods of the present invention, preferably a large volume loading dose is used at the start of the treatment. The treatment then is continued with a maintenance dose. Further administration then can be determined by monitoring at intervals the levels of the morphogen in the blood.

Where injury to hepatic tissue is induced deliberately as part of, for example, a surgical or other medical procedure, the morphogen preferably is provided just prior to, or concomitant with induction of the trauma. Preferably, the morphogen is administered prophylactically in a surgical setting. Optimally, the morphogen dosage given in all cases is between 1–100 μg of protein per kilogram weight of the patient.

As described above, as an alternative or, in addition, an effective amount of an agent capable of stimulating endogenous morphogen levels may be administered by any of the routes described above. For example, an agent capable of stimulating morphogen production and/or secretion from liver tissue cells or from cells at a distant site which then is targeted to the liver, may be provided to a mammal. A method for identifying and testing agents capable of modulating the levels of endogenous morphogens in a given tissue is described generally herein in Example 9, and in detail in commonly owned U.S. Ser. No. 07/938,021 filed Aug. 28, 1992 and U.S. Ser. No. 752,859, filed Aug. 30, 1991, both now abandoned, the disclosures of which are incorporated herein by reference. Briefly, candidate compounds can be identified and tested by incubating the compound in vitro with a test tissue or cells thereof, for a time sufficient to allow the compound to affect the production, i.e., the expression and/or secretion, of a morphogen produced by the cells of that tissue. Here, suitable tissue or cultured cells of a tissue preferably would comprise hepatic tissue cells.

A currently preferred detection means for evaluating the level of the morphogen in culture upon exposure to the candidate compound comprises an immunoassay utilizing an antibody or other suitable binding protein capable of reacting specifically with a morphogen and being detected as part of a complex with the morphogen. Immunoassays may be performed using standard techniques known in the art and antibodies raised against a morphogen and specific for that morphogen. Agents capable of stimulating endogenous morphogens then may formulated into pharmaceutical preparations and administered as described herein.

VI. EXAMPLES

Example 1

Identification of Morphogen-Expressing Tissue

Determining the tissue distribution of morphogens may be used to identify different morphogens expressed in a given tissue, as well as to identify new, related morphogens. Tissue distribution also may be used to identify useful morphogen-producing tissue for use in screening and identifying candidate morphogen-stimulating agents. The morphogens (or their mRNA transcripts) readily are identified in different tissues using standard methodologies and minor modifications thereof in tissues where expression may be low. For example, protein distribution may be determined using standard Western blot analysis or immunofluorescent techniques, and antibodies specific to the morphogen or morphogens of interest. Similarly, the distribution of morphogen transcripts may be determined using standard Northern hybridization protocols and transcript-specific probes.

Any probe capable of hybridizing specifically to a transcript, and distinguishing the transcript of interest from other, related transcripts may be used. Because the morphogens described herein share such high sequence homology in their active, C-terminal domains, the tissue distribution of a specific morphogen transcript may best be determined using a probe specific for the pro region of the immature protein and/or the N-terminal region of the mature protein. Another useful sequence is the 3' non-coding region flanking and immediately following the stop codon. These portions of the sequence vary substantially among the morphogens of this invention, and accordingly, are specific for each protein. For example, a particularly useful Vgr-1-specific probe sequence (e.g., a probe for specific detection of nucleic acid encoding a Seq. ID No. 13 polypeptide) is the PvuII-SacI fragment, a 265 bp fragment encoding both a portion of the untranslated pro region and the N-terminus of the mature sequence (see Lyons et al. (1989) PNAS 86:4554–4558 for a description of the cDNA sequence). Similarly, particularly useful mOP-1-specific probe sequences (e.g., probe sequences for detecting nucleic acids corresponding to the prodomain sequence in Seq. ID No. 18) are the BstX1-BglI fragment, a 0.68 Kb sequence that covers approximately two-thirds of the mOP-1 pro region; a StuI-StuI fragment, a 0.2 Kb sequence immediately upstream of the 7-cysteine domain; and the EarI-Pst1 fragment, an 0.3 Kb fragment containing a portion of the 3' untranslated sequence. Similar approaches may be used, for example, with hOP-1 (Seq. ID No. 16) or human or mouse OP-2 (Seq. ID Nos. 20 and 22, respectively).

Using these morphogen-specific probes, which may be synthetically engineered or obtained from cloned sequences, morphogen transcripts can be identified in mammalian tissue, using standard methodologies well known to those having ordinary skill in the art. Briefly, total RNA is prepared from various adult murine tissues (e.g., liver, kidney, testis, heart, brain, thymus and stomach) by a standard methodology such as by the method of Chomczyaski et al. ((1987) Anal. Biochem 162:156–159) and described below. Poly (A)+RNA is prepared by using oligo (dT)-cellulose chromatography (e.g., Type 7, from Pharmacia LKB Biotechnology, Inc.). Poly (A)+RNA (generally 15 μg) from each tissue is fractionated on a 1% agarose/formaldehyde gel and transferred onto a Nytran membrane (Schleicher & Schuell). Following the transfer, the membrane is baked at 80° C. and the RNA is cross-linked under UV light (generally 30 seconds at 1 mW/cm$^2$). Prior to hybridization, the appropriate probe is denatured by heating. The hybridization is carried out in a lucite cylinder rotating in a roller bottle apparatus at approximately 1 rev/min for approximately 15 hours at 37° C. using a hybridization mix of 40% formamide, 5×Denhardts, 5×SSPE, and 0.1% SDS. Following hybridization, the non-specific counts are washed off the filters in 0.1×SSPE, 0.1% SDS at 50° C.

Examples demonstrating the tissue distribution of various morphogens, including Vgr-1, OP-1, BMP2, BMP3, BMP4, BMP5, GDF-1, and OP-2 (e.g., Seq. ID Nos. 13, 5, 9, 26, 10, 27, 14 and 6, respectively) in developing and adult tissue are disclosed in commonly owned, now abandoned U.S. Ser.

No. 752,764, and in Ozkaynak, et al., (1991) *Biochem. Biophys. Res. Commn.* 179:116–123, and Ozkaynak, et al. (1992) *J. Biol. Chem.*, press), the disclosures of which are incorporated herein by reference. Using the general probing methodology described herein, northern blot hybridizations using probes specific for these morphogens to probe brain, spleen, lung, heart, liver and kidney tissue indicate that kidney-related tissue appears to be the primary expression source for OP-1 (comprising, e.g., Seq. ID No. 5), with brain, heart and lung tissues being secondary sources. Lung tissue appears to be the primary tissue expression source for Vgr-1, BMP5, BMP4 and BMP3 (comprising respectively, e.g., Seq. ID Nos. 13, 27, 10 and 26) Lower levels of Vgr-1 (comprising, ;e.g., Seq. ID No. 13) also are seen in kidney and heart tissue, while the liver appears to be a secondary expression source for BMP5, (comprising, e.g., Seq. ID No. 27) and the spleen appears to be a secondary expression source for BMP4 (comprising, e.g., Seq. ID No. 10). GDF-1 (comprising, e.g., Seq. ID No. 14) appears to be expressed primarily in brain tissue. To date, OP-2 (comprising, e.g., Seq. ID No. 7) appears to be expressed primarily in early embryonic tissue. Specifically, northern blots of murine embryos and 6-day post-natal animals shows abundant OP2 expression in 8-day embryos. Expression is reduced significantly in 17-day embryos and is not detected in post-natal animals.

Example 2

Morphogen Localization in Developing Hepatic Tissue

The onset of liver formation in a developing embryo occurs at day 14. Using the hybridization protocol described in Example 1, morphogen expression was identified at the onset of liver formation during embryo development. Specifically, northern blots of mRNA isolated from murine embryo liver tissue (probed at 15 days and 20 days) and post natal mouse liver tissue (probed at 7, 14, 21 and 28 days past birth) show mOP-1 (e.g., Seq. ID No. 18) expression in developing liver tissue only during the time of liver formation. Specifically, as illustrated, in FIG. 1, mOP-1 RNA (e.g., RNA complementary to Seq. ID No. 18) is expressed significantly in the 15 day embryo, and is present at much lower amounts at later times in healthy hepatic tissue. In the figure, lanes 2 and 3 contain RNA from 15- and 20-day embryo tissue, lanes 4–8, RNA from 3, 7, 14, 21 and 28 days post natal animals, and lane 8 is a molecular weight ladder. Lanes 1 and 9 are markers. mOP-1 RNA (e.g., complementary to Seq. ID No. 18) appears as a discrete band running at about 4 kb and 2.2 or 2.4 kb, as well as a shorter band at 1.8 kb (see, for example, Ozkaznak, et al. (1991) *Biochem. Biophys Res.* 179: 116–123.

Example 3

Mitogenic Effect of Morphogen on Rat Hepatocytes

The ability of a morphogen to induce proliferation of primary hepatocytes may be demonstrated in vitro using the following assay using primary hepatocytes isolated from rat liver. Unless otherwise indicated, all chemicals referenced are standard, commercially available reagents, readily available from a number of sources, including Sigma Chemical, Co., St. Louis; Calbiochem, Corp., San Diego, and Aldrich Chemical Co., Milwaukee.

Rat primary hepatocyte cultures were prepared by a two-step collagenase digestion essentially as described by Fausto et al. (1987) *Cell Separation: Methods and Selected Applications* 4:45–77 the disclosure of which is incorporated herein by reference. Briefly, the liver of a male rat (e.g., CD strain, Charles River Laboratories, Wilmington, Mass.) was perfused via the portal vein with $Ca^{2+}$ free and $Mg^{2+}$ free Hank's balanced salt solution for 10 min at a flow of 30–40 ml/min, followed by perfusion with 0.05% collagenase in $Ca^{2+}$-containing medium (Hepes buffer) for 10 min. The liver capsule was removed, the cells shaken loose from the tissue and filtered hepatocytes were collected by repeated centrifugation of the cell suspension at 50 xg for 25 min. Hepatocyte suspensions were virtually free of non-parenchymal cell contamination. Cells ($2 \times 10^5$ per dish) were plated on 35-mm dishes coated with rat tail collagen in MEM (modified Eagle's Medium, Gibco, Long Island) containing 5% fetal bovine serum (FBS), 1 mM pyuvate, 0.2 mM aspartate, 1 mM proline, 0.2 mM serine, 2 mM glutamine, and 0.5 $\mu$g of hydrocotisone and 1 $\mu$g of insulin per ml. The cells were incubated for 24 hours under standard at 37° C., at which time the growth medium was replaced with serum-free MEM.

The cell culture then was divided into two groups: (1) wells which received morphogen within the dose range of 1–100 ng of morphogen per ml medium; and (2) the control group, which received no additional factors. In this example, OP-1 (e.g., Seq. ID No. 5) was the morphogen tested. The cells then were incubated for an additional 18–24 hours after which the wells were pulsed with 2 $\mu$Ci/well of $^3$H-thymidine and incubated for six more hours. The excess label then was washed off with a cold solution of 0.15 M NaCl. 250 $\mu$l of 10% tricholoracetic acid then was added to each well and the wells incubated at room temperature for 30 minutes. The cells then were washed three times with cold distilled water, and lysed by the addition of 250 $\mu$l of 1% sodium dodecyl sulfate (SDS) for a period of 30 minutes at 37° C. The cell lysates then were harvested using standard means well known in the art, and the incorporation of $^3$H-thymidine into cellular DNA was determined by liquid scintillation as an indication of mitogenic activity of the cells.

Morphogen treatment of primary hepatocyte cultures significantly stimulates $^3$ H-thymidine incorporation into DNA, and thus promotes their cell proliferation. The mitogenesis stimulated by 20 ng of OP-1 (e.g., Seq. ID No. 5) in 1 ml serum-free medium was equivalent to the mitogenic effect of 10% fresh serum alone. By contrast, other local-acting growth factors, such as TGF-β do not stimulate proliferation of primary hepatocytes (see Fausto et al. (1991) *Ciba Found Symp* 157:165–174.)

Example 4

Morphogen-Induced Liver Regeneration

While hepatocytes have a remarkable capacity to undergo compensatory growth following tissue loss, the reparative properties of liver differ significantly from embryonic morphogenesis. Specifically, following a partial hepatectomy wherein a liver lobe is partially or completely removed, the remaining intact lobes grow rapidly and double in weight due to the ability of the differentiated hepatocytes in the intact lobe to undergo limited proliferation. However, the excised lobe itself is not regenerated. The following example demonstrates the ability of morphogens to regenerate lost hepatic tissue following a partial hepatectomy, including regenerating the excised tissue lobe. The protocol described below is a variation on a standard partial hepatectomy protocol, described, for example, by Higgins et al. (1931)

Arch. Pathol. 12:136–202 and Braun et al. (1989) PNAS 86:1558–1562, the disclosures of which are incorporated herein by reference.

Morphogen, e.g., purified recombinant human OP-1, mature form (Seq. ID No. 5), was solubilized (1 mg/ml) in 50% ethanol (or compatible solvent) containing 0.1% trifluoroacetic acid (or compatible acid). The injectable OP-1 solution was prepared by diluting one volume of OP-1/solvent-acid stock solution with 9 volumes of 0.2% rat serum albumin in sterile PBS (phosphate-buffered saline).

Growing rats or aged rats were anesthetized by using ketamine. Two of the liver lobes (left and right) were cut out (approximately ⅓ of the lobe) and the morphogen was injected locally at multiple sites along the cut ends. The amount of OP-1 injected was 100 µg in 100 of PBS/RSA (phosphate-buffered saline/rat serum albumin) injection buffer. Placebo samples were injection buffer without OP-1. Five rats in each group were used. The wound was closed using standard surgical procedures and the rats were allowed to eat normal food and drink tap water.

Figure 2:
FIG. 2 is a photograph showing the effect of phosphate buffered saline (PBS, animal 1) or morphogen (OP-1, animal 2) on partially hepatectomized rats (arrow indicates the treated lobe in both animals)

After 12 days, the rats were sacrificed and liver regeneration was observed visually. The photograph in FIG. 2 illustrates dramatically the regenerative effects of OP-1 (e.g., Seq. ID No. 5) on liver tissue formation. In the figure, the arrow indicates the treated lobe. The OP-1-injected group showed complete liver tissue regeneration including reformation of the excised lobe tissue, and showed no sign of any cut in the liver (animal 2). By contrast, in the control group into which only PBS was injected, the excised lobe tissue was not regenerated (animal 1). The original incision remains visible.

Figure 3:
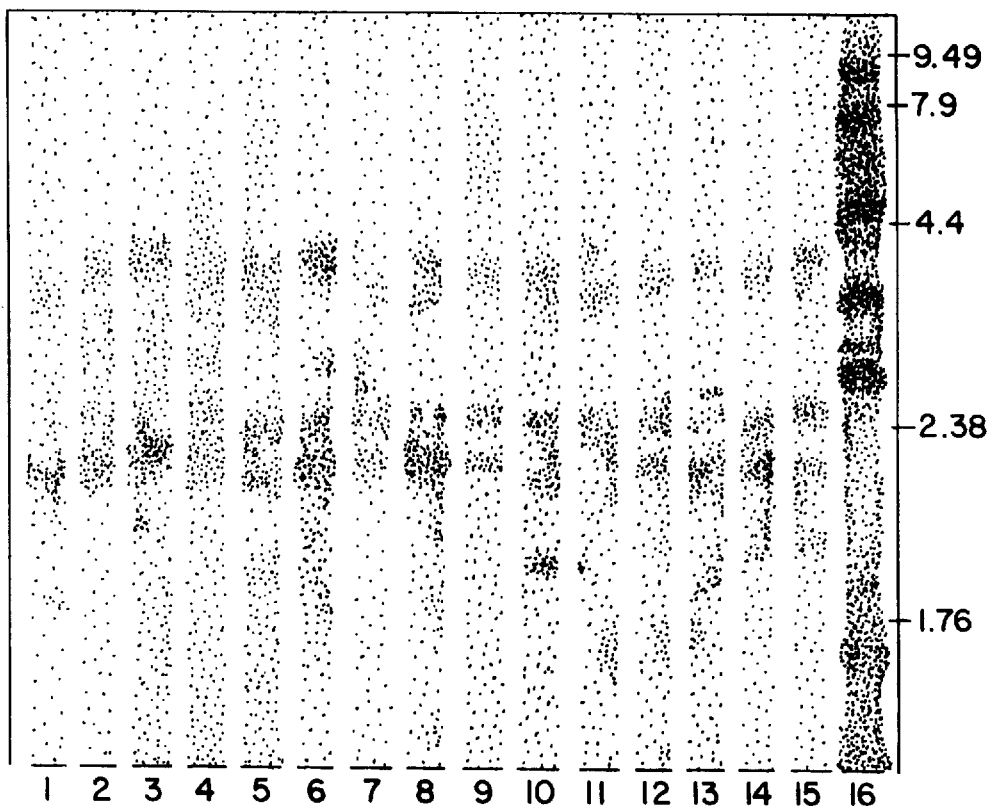
FIG. 3 is a photograph of a Northern blot of mRNA isolated from sham-operated (lanes 3, 5, 7, 9, 11, 13 and 15) and partially hepatectomized rats (lanes 2, 4, 6, 8, 10, 12, 14) at 6 hr intervals between 12–96 hours post surgery, probed with an mOP-1-specific probe.

In a related experiment, animals were partially hepatectomized or sham-operated and Northern blot analysis performed on RNA isolated from the liver tissue. None of the animals were morphogen-treated. As determined by Northern blot analysis (probed with mOP-1-specific (e.g., Seq. ID No. 18 specific) labeled oligonucleotide, see FIG. 3), in the absence of morphogen treatment, the level of endogenous morphogen is not enhanced significantly following partial hepatectomy. In the FIG. lanes 2, 4, 6, 8, 10, 12, and 14, are samples from partially hepatectomized rats and lanes 3, 5, 7, 9, 11, 13, and 15 are samples from sham-operated rats, and lanes 1 and 16 are markers. Samples were taken at 6 hour intervals between 12 and 96 hours post surgery.

Example 5

Morphogen Expression in Regenerating Liver Tissue Following Toxin-Induced Tissue Damage Hepatic tissue repair following toxic agent-induced damaged tissue involves proliferation and differentiation of hepatocyte precursor cells. This tissue reparation apparently mimics the tissue morphogenesis cascade that occurs during embryogenesis (Fausto, et al.(1989) Lab.Investigation 60:4–13). As demonstrated in the example below, morphogen expression is enhanced significantly during hepatic tissue regeneration following galactosamine or carbon tetrachloride ($CCl_4$)-induced liver damage. Experiments were performed essentially as described in Kuhlmann et al., (1980) Virchows Arch 387:47–57, the disclosure of which is incorporated herein by reference .

Figure 4:
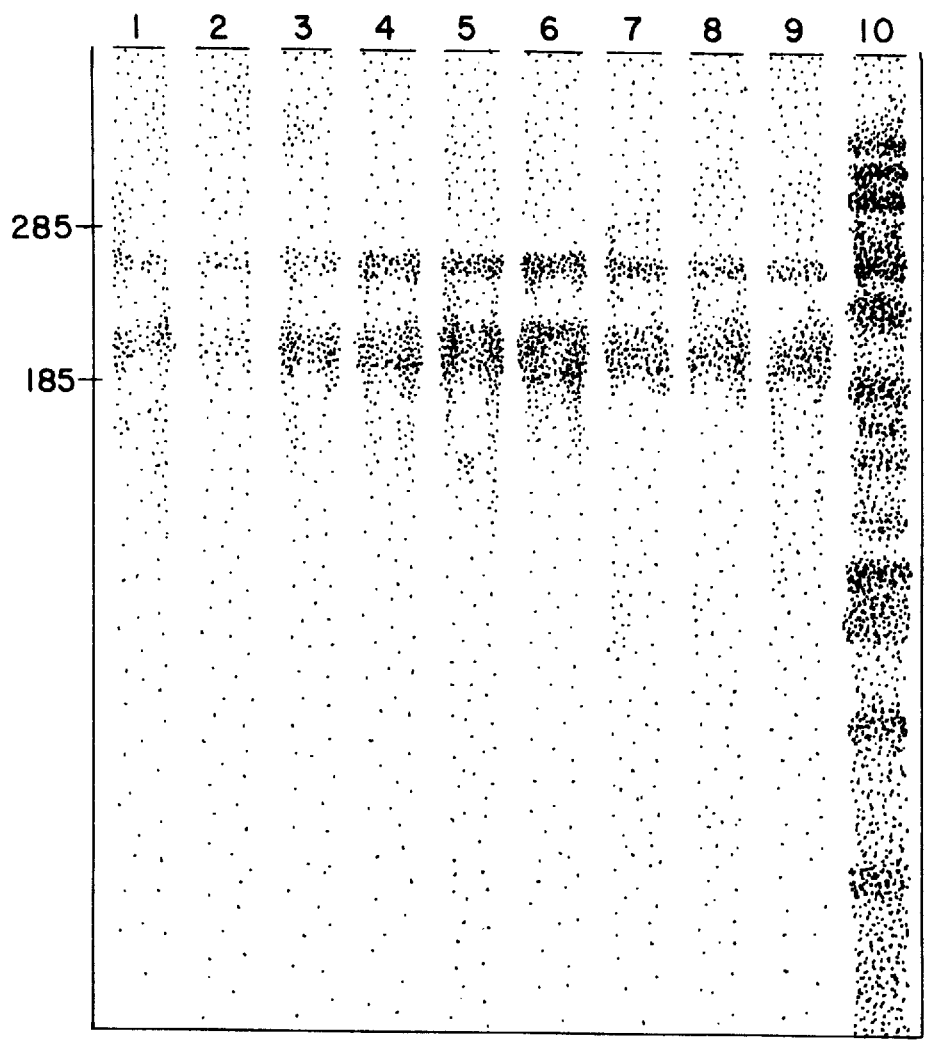
FIG. 4 is a photograph of a Northern blot of mRNA isolated from galactosamine-treated rats and probed with mOP-1-specific probe on days 0–7, 10 (lanes 1–9, respectively)

In this experiment, male rats were provided with a single intraperitoneal injection of galactosamine-HCl 0.75 g/.kg body weight on day 0, and morphogen expression monitored by standard Northern blot of liver tissue samples taken on days 1–7 and day 10. OP-1 expression (e.g., Seq. ID No. 18 expression) was significantly enhanced during this hepatic tissue regenerative period, indicating that morphogens play a significant role in tissue regeneration. In FIG. 4, lanes 1–8, are samples taken on days 0–7; lane 9 is a sample taken on day 10, and lane 10 contains molecular weight markers. OP-1 mRNA (e.g., complementary to Seq. ID No. 18) shows a significant expression spike on days 3–7. Similar results were seen with tissue regeneration stimulated following $CCl_4$-induced tissue, wherein $CCl_4$ intoxication is induced by orally administering 1.5 g $CCl_4$/kg body weight. Significant morphogen expression (mOP-1 mRNA, as determined by standard Northern blot) is identified by a hybridization spike at 12 hours and continuing through at least 72 hours.

Example 6

Morphogen Inhibition of Cellular and Humoral Inflammatory Response

The morphogens described herein may be used to alleviate tissue damage associated with immune response-mediated damage to liver tissue. Details of this damage and the use of morphogens to alleviate this injury as well as to provide a cytoprotective effect in anticipation of this injury for example, during a transplant procedure, are disclosed in commonly owned U.S. Ser. No. 07/938,336 and U.S. Ser. No. 07/938,337, both filed Aug. 28, 1992 and now-abandoned, and U.S. Ser. No. 753,059, filed Aug. 30, 1991 (also now abandoned). A primary source of such damage to hepatic tissue results, for example, from reduced perfusion of the hepatic blood supply and/or from partial or complete occlusion of the portal vein. As described in U.S. Ser. Nos. 07/938,336 and in 753,059, morphogens have been shown to alleviate damage to myocardial tissue following ischemia-reperfusion injury. The morphogens also alleivate analogous tissue damage to hepatic tissue.

Figure 5A:
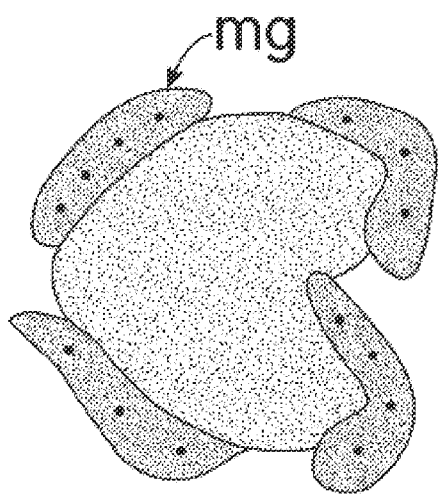
FIGS. 5 (A and B) are schematic representations of morphogen inhibition of early mononuclear phagocytic cell multinuclearization in vivo.
Figure 5B:
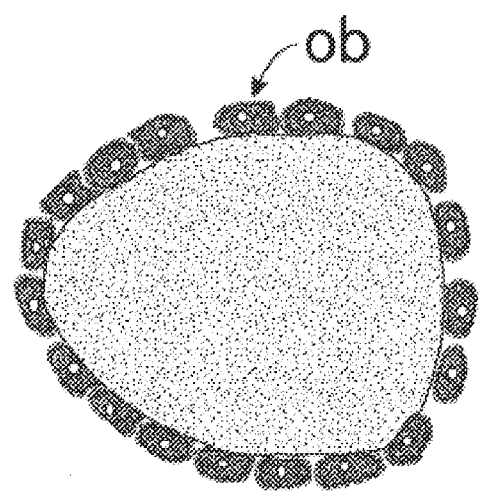
Figure 6A:
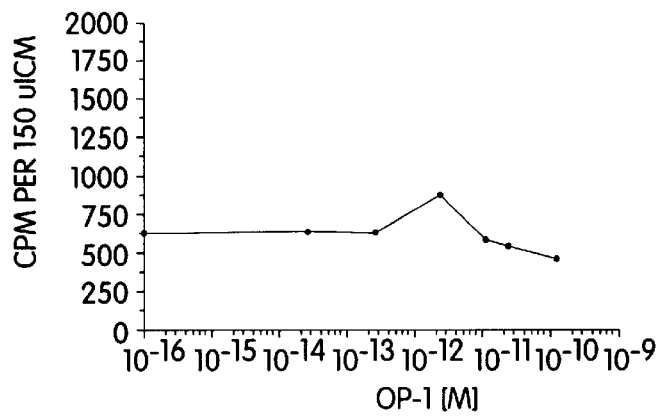
FIGS. 6 (A–D) graphs the effects of a morphogen (e.g., OP-1, FIGS. 6A and 6C) and TGF-B (FIG. 6B and 6D) on collagen (6A and 6B) and hyaluronic acid (6C and 6D) production in primary fibroblast cultures.
Figure 6B:
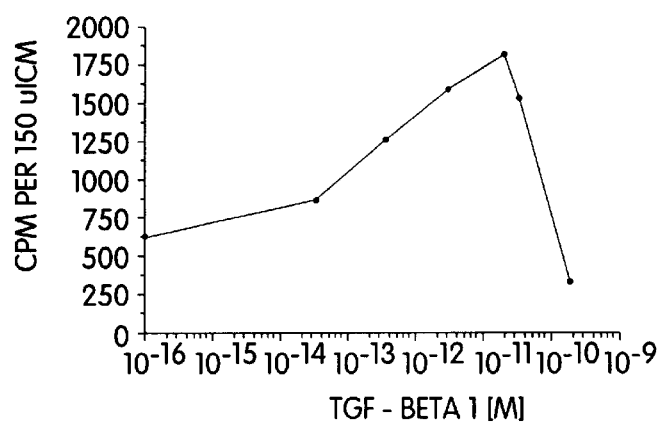
Figure 6C:
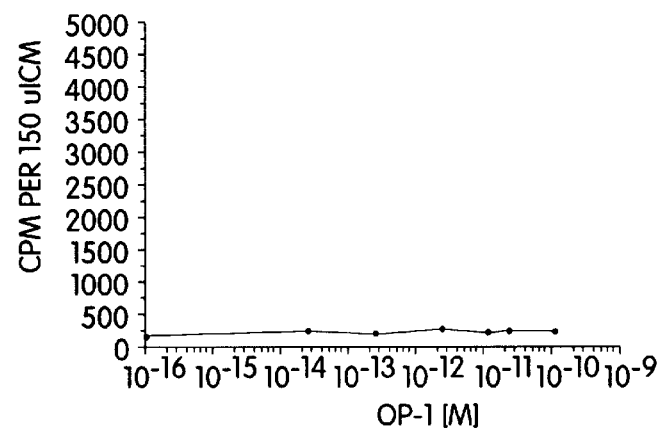
Figure 6D:
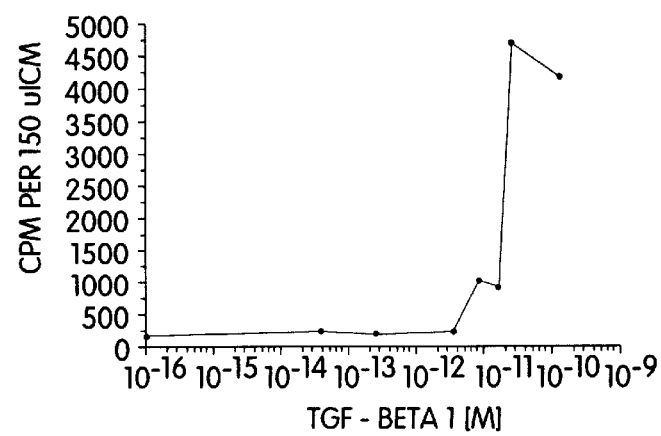

Morphogens described herein inhibit multinucleation of mononuclear phagocytic cells under conditions where these cells normally would be activated, e.g., in response to a tissue injury or the presence of a foreign substance. For example, in the absence of morphogen, an implanted substrate material (e.g., implanted subcutaneously) composed of, for example, mineralized bone, a ceramic such as titanium oxide or any other substrate that provokes multinucleated giant cell formation, rapidly becomes surrounded by multinucleated giant cells, e.g., activated phagocytes stimulated to respond and destroy the foreign object. In the presence of morphogen however, the recruited cells remain in their mononuclear precursor form and the matrix material is undisturbed. FIG. 5 illustrates this effect of morphogens, in a schematic representation of histology results of a titanium oxide substrate implanted subcutaneously. In the figure, "mg" means multinucleated giant cells and "ob" means osteoblasts. The substrate represented in FIG. 5B was implanted together with morphogen (OP-1; e.g., Seq. ID No. 5) and newly formed osteoblasts are evident surrounding the substrate. By contrast, the substrate represented in FIG. 5A was implanted without morphogen and extensive multinucleated giant cell formation is evident surrounding the substrate. Accordingly, the morphogens' effect in a mammal also may include inhibiting activation of these giant cells.

In addition, the morphogens described herein also suppress antibody production stimulated in response to a foreign antigen in a mammal. Specifically, when bovine bone collagen matrix alone was implanted in a bony site in a rat, a standard antibody response to the collagen is stimulated in the rat as determined by standard anti-bovine collagen ELISA experiments performed on blood samples taken at four week intervals following implantation (e.g., between 12 and 20 weeks.) Serum anti-collagen antibody titers, measured by ELISA essentially following the procedure described by Nagler-Anderson et al, (1986) *PNAS* 83:7443–7446, the disclosure of which is incorporated herein by reference, increased consistently throughout the experiment. However, when the matrix was implanted together with a morphogen (e.g., OP-1 Seq. ID No. 5), dispersed in the matrix and adsorbed thereto, essentially as described in U.S. Pat. No. 4,968,590) anti-bovine collagen antibody production was suppressed significantly. This ability of morphogen to suppress the humoral response is further evidence of morphogen utility in alleviating tissue damage.

Example 7

Morphogen Effect on Fibrogenesis and Scar Tissue Formation

The morphogens described herein induce tissue morphogenesis of damaged or lost tissue. The ability of these proteins to regenerate new tissue also is enhanced by the anti-inflammatory effect of these proteins. Provided below are a series of in vitro experiments demonstrating the ability of morphogens to induce migration and accumulation of mesenchymal cells. In addition, the experiments demonstrate that morphogens, unlike TGF-β, do not stimulate fibrogenesis or scar tissue formation. Specifically, morphogens do not stimulate production of collagen, hyaluronic acid (HA) or metalloproteinases in primary fibroblasts, all of which are required for fibrogenesis or scar tissue formation. By contrast, TGF-β, a known inducer of fibrosis, but not of tissue morphogenesis as described herein, does stimulate production of these fibrosis markers.

Chemotaxis and migration of mesenchymal progenitor cells were measured in modified Boyden chambers essentially as described by Fava, R.A. et al (1991) *J. Exp. Med.* 173: 1121–1132, the disclosure of which is incorporated herein by reference, using polycarbonate filters of 2, 3 and 8 micron ports to measure migration of progenitor neutrophils, monocytes and fibroblasts. Chemotaxis was measured over a range of morphogen concentrations, e.g., $10^{-20}$M to $10^{-12}$M OP-1 (e.g., Seq. ID No. 5). For progenitor neutrophils and monocytes, $10^{-18}$–$10^{-17}$M OP-1 (e.g., Seq. ID No 5) consistently induced maximal migration, and $10^{-14}$ to $10^{-13}$M OP-1 (e.g., Seq. ID No. 5) maximally induced migration of progenitor fibroblasts. In all cases the chemotactic activity could be inhibited with anti-OP-1 antibody (e.g., antibody reactive with a Seq. ID No. 5 polypeptide). Similar migration activities also were measured and observed with TGF-β.

The effect of morphogen on fibrogenesis was determined by evaluating fibroblast production of hyaluronic acid (HA), collagen, collagenese and tissue inhibitor of metalloproteinases (TIMP).

Human fibroblasts were established from explants of infant foreskins and maintained in monolayer culture using standard culturing procedures. (See, for example, (1976) *J. Exp. Med.* 144: 1188–1203.) Briefly, fibroblasts were grown in maintenance medium consisting of Eagle's MEM, supplemented with nonessential amino acids, ascorbic acid (50 μg/ml), NaHCO$_3$ and HEPES buffers (pH 7.2), penicillin (100 U/ml), streptomycin (100 μg/ml), amphotericin B (1 μg/ml) and 9% heat inactivated FCS. Fibroblasts used as target cells to measure chemotaxis were maintained in 150 mm diameter glass petri dishes. Fibroblasts used in assays to measure synthesis of collagen, hyaluronic acid, collagenase and tissue inhibitors of metalloproteinases (TIMP) were grown in 100 mm diameter plastic tissue culture petri dishes.

The effects of morphogen on fibroblast production of hyaluronic acid, collagens, collagenase and TIMP were determined by standard assays (See, for example, Posttethwaite et al. (1989) *J. Clin. Invest.* 83: 629–636, Posttethwaithe (1988) *J./Cell Biol.* 106: 311–318 and Clark et al (1985) *Arch. Bio-chem Biophys.* 241: 36–44, the disclosures of which are incorporated by reference.) For these assays, fibroblasts were transferred to 24-well tissue culture plates at a density of $8 \times 10^4$ cells per well. Fibroblasts were grown to confluency in maintenance medium containing 9% FCS for 72 h and then grown in serum-free maintenance medium for 24 h. Medium was then removed from each well and various concentrations of OP-1 (recombinantly produced mature or soluble form, comprising, e.g., Seq. ID No. 5) or TGF-β-1 (R&D Systems, Minneapolis) in 50 μl PBS were added to triplicate wells containing the confluent fibroblast monolayers. For experiments that measured production of collagenase and TIMP, maintenance medium (450 μl) containing 5% FCS was added to each well, and culture supernatants were harvested from each well 48 h later and stored at $-70°$C. until assayed. For experiments that assessed HA production, maintenance medium (450 μl) containing 2.5% FCS was added to each well, and cultures grown for 48 h. For experiments that measured fibroblast production of collagens, serum-free maintenance medium (450 μl) without non-essential amino acids was added to each well and cultures grown for 72 h. Fibroblast production of HA was measured by labeling newly synthesized glycosaminoglycans (GAG) with [$^3$H]-acetate during the last 24 h of culture and quantitating released radioactivity after incubation with hyaluronidase from *Streptomyces hyalurolyticus* (ICN Biochemicals, Cleveland, Ohio) which specifically degrades hyaluronic acid. Production of total collagen by fibroblasts was measured using a collagenase-sensitive protein assay that reflects [$^3$H]-proline incorporation the last 24 h of culture into newly synthesized collagens. Collagenase and TIMP protein levels in fibroblast cultures supernatants was measured by specific ELISAs.

As shown in FIG. 6, OP1 (e.g., Seq. ID No. 5) does not stimulate significant collagen or HA production, as compared with TGF-β. In the figure, panel A shows OP-1 (e.g., Seq. ID No. 5) effect on collagen production, panel B shows TGF-β effect on collagen production, and panels C and D show OP-1 (e.g., Seq. ID No. 5; Panel C) and TGF-β (panel D) effect on HA production. The morphogen results were the same whether the soluble or mature form of OP1 (comprising, e.g., Seq. ID No. 5) was used. By contrast, the latent form of TGF-β (e.g., pro domain-associated form of TGF-β) was not active.

Example 8

Liver Tissue Diagnostics

Morphogen localization in developing and regenerating liver tissue can be used as part of a method for diagnosing a liver function disorder in vivo. The method may be particularly advantageous for diagnosing early stages of a liver dysfunction associated with a hepatocellular injury. Specifically, a biopsy of liver tissue is performed on a patient at risk, using standard procedures known in the medical art. Morphogen expression associated with the biopsied tissue then is assessed using standard methodologies, as by immunolocalization, using standard immunofluorescence techniques in concert with morphogen-specific antisera or monoclonal antibodies. Specifically, the biopsied tissue is thin sectioned using standard methodologies known in the art, and fluorescently labelled (or otherwise detectable) antibodies incubated with the tissue under conditions sufficient to allow specific antigen-antibody complex formation. The presence and quantity of complex formed then is detected and compared with a predetermined standard or reference value. Detection of altered levels of morphogen present in the tissue then may be used as an indicator of tissue dysfunction. Alternatively, fluctuation in morphogen levels may be assessed by monitoring morphogen transcription levels, either by standard Northern blot analysis or in situ hybridization, using a labelled probe capable of hybridizing specifically to morphogen RNA and standard RNA hybridization protocols well described in the art and as described in Examples 1, 2, 5 and 6.

Fluctuations in morphogen levels present in the bloodstream or peritoneal fluid also may be used to evaluate liver tissue viability. For example, morphogens are detected associated with regenerating liver tissue and/or may be released from dying cells into surrounding peritoneal fluid. OP-1 (comprising, e.g., Seq. ID No. 5) recently has been identified in human blood, which also may be a means of morphogen transport.

Serum samples may be obtained by standard venipuncture and serum prepared by centrifugation at 3,000 RPM for ten minutes. Similarly, peritoneal fluid samples may be obtained by a standard fluid extraction methodology. The presence of morphogen in the serum or peritoneal fluid then may be assessed by standard Western blot (immunoblot), ELISA or RIA procedures. Briefly, for example, with the ELISA, samples may be diluted in an appropriate buffer, such as phosphate-buffered saline, and 50 µl aliquots allowed to absorb to flat bottomed wells in microtitre plates pre-coated with morphogen-specific antibody, and allowed to incubate for 18 hours at 4° C. Plates then may be washed with a standard buffer and incubated with 50 µl aliquots of a second morphogen-specific antibody conjugated with a detecting agent, e.g., biotin, in an appropriate buffer, for 90 minutes at room temperature. Morphogen-antibody complexes then may be detected using standard procedures.

Alternatively, a morphogen-specific affinity column may be created using, for example, morphogen-specific antibodies adsorbed to a column matrix, and passing the fluid sample through the matrix to selectively extract the morphogen of interest. The morphogen then is eluted. A suitable elution buffer may be determined empirically by determining appropriate binding and elution conditions first with a control (e.g., purified, recombinantly-produced morphogen.) Fractions then are tested for the presence of the morphogen by standard immunoblot. Morphogen concentrations in serum or other fluid samples then may be determined using standard protein quantification techniques, including by spectrophotometric absorbance or by quantitation by ELISA or RIA antibody assays. Using this procedure, OP-1 (comprising, e.g., Seq. ID No. 5) has been identified in serum.

OP-1 (comprising, e.g., Seq. ID No. 5) was detected in human serum using the following assay. A monoclonal antibody raised against mammalian, recombinantly produced OP-1 (e.g., Seq. ID No. 5) using standard immunology techniques well described in the art and described generally in Example 13, was immobilized by passing the antibody over an activated agarose gel (e.g., Affi-Gel™, from Bio-Rad Laboratories, Richmond, Calif., prepared following manufacturer's instructions), and used to purify OP-1 from serum. Human serum then was passed over the column and eluted with 3M K-thiocyanate. K-thiocyanante fractions then were dialyzed in 6M urea, 20 mM $PO_4$, pH 7.0, applied to a C8 HPLC column, and eluted with a 20 minute, 25–50% acetonitrile/0.1% TFA gradient. Mature, recombinantly produced OP-1 (e.g., Seq. ID No. 5) homodimers elute between 20–22 minutes. Accordingly, these fractions from the affinity-purified human serum sample were collected and tested for the presence of OP-1 (e.g., Seq. ID No. 5) by standard immunoblot using an OP-1-specifc antibody, and the protein identity confirmed by N-terminal sequencing.

Morphogens may be used in diagnostic applications by comparing the quantity of morphogen present in a body fluid sample with a predetermined reference value, with fluctuations in fluid morphogen levels indicating a change in the status of liver tissue. Alternatively, fluctuations in the level of endogenous morphogen antibodies may be detected by this method, most likely in serum, using an antibody or other binding protein capable of interacting specifically with the endogenous morphogen antibody. Detected fluctuations in the levels of the endogenous antibody may be used as indicators of a change in tissue status.

Example 9

Screening Assay for Candidate Compounds which Alter Endogenous Morphogen Levels

Candidate compound(s) which may be administered to affect the level of a given morphogen may be found using the following screening assay, in which the level of morphogen production by a cell type which produces measurable levels of the morphogen is determined with and without incubating the cell in culture with the compound, in order to assess the effects of the compound on the cell's production of morphogen. This can be accomplished by detection of the morphogen either at the protein or RNA level. A more detailed description also may be found in commonly owned, now abandoned U.S. Ser. No. 752,861, incorporated hereinabove by reference.

9.1 Growth of Cells in Culture

Cell cultures of kidney, adrenals, urinary bladder, brain, or other organs, may be prepared as described widely in the literature. For example, kidneys may be explanted from neonatal or new born or young or adult rodents (mouse or rat) and used in organ culture as whole or sliced (1–4 mm) tissues. Primary tissue cultures and established cell lines, also derived from kidney, adrenals, urinary, bladder, brain, mammary, or other tissues may be established in multiwell plates (6 well or 24 well) according to conventional cell culture techniques, and are cultured in the absence or presence of serum for a period of time (1–7 days). Cells may be cultured, for example, in Dulbecco's Modified Eagle medium (Gibco, Long Island, N.Y.) containing serum (e.g., fetal calf serum at 1%–10%, Gibco) or in serum-deprived medium, as desired, or in defined medium (e.g., containing insulin, transferrin, glucose, albumin, or other growth factors).

Samples for testing the level of morphogen production include culture supernatants or cell lysates, collected periodically and evaluated for OP-1 (comprising, e.g., Seq. ID No. 6) production by immunoblot analysis (Sambrook et al., eds., 1989, Molecular Cloning, Cold Spring Harbor Press, Cold Spring Harbor, N.Y.), or a portion of the cell culture itself, collected periodically and used to prepare polyA+ RNA for mRNA analysis. To monitor de novo OP-1 (e.g., Seq. ID No. 6) synthesis, some cultures are labeled according to conventional procedures with an $^{35}$S-methionine/$^{35}$S-cysteine mixture for 6–24 hours and then evaluated for OP-1 (e.g., Seq. ID No. 6) synthesis by conventional immunoprecipitation methods.

9.2 Determination of Level of Morphogenic Protein

In order to quantitate the production of a morphogenic protein by a cell type, an immunoassay may be performed to detect the morphogen using a polyclonal or monoclonal antibody specific for that protein. For example, OP-1 (comprising, e.g., Seq. ID No. 5) may be detected using a polyclonal antibody specific for OP-1 (e.g., specific for a Seq. ID No. 5 polypeptide) in an ELISA, as follows.

1 μg/100 μl of affinity-purified polyclonal rabbit IgG specific for OP-1 (e.g., Seq. ID No. 5) is added to each well of a 96-well plate and incubated at 37° C. for an hour. The wells are washed four times with 0.167M sodium borate buffer with 0.15M NaCl (BSB), pH 8.2, containing 0.1% Tween 20. To minimize non-specific binding, the wells are blocked by filling completely with 1% bovine serum albumin (BSA) in BSB and incubating for 1 hour at 37° C. The wells are then washed four times with BSB containing 0.1% Tween 20. A 100 μl aliquot of an appropriate dilution of each of the test samples of cell culture supernatant is added to each well in triplicate and incubated at 37° C. for 30 min. After incubation, 100 μl biotinylated rabbit anti-OP-1 (e.g., Anti-Seq. ID No. 5) serum (stock solution is about 1 mg/ml and diluted 1:400 in BSB containing 1% BSA before use) is added to each well and incubated at 37° C. for 30 min. The wells are then washed four times with BSB containing 0.1% Tween 20. 100 μl strepavidin-alkaline (Southern Biotechnology Associates, Inc. Birmingham, Ala., diluted 1:2000 in BSB containing 0.1% Tween 20 before use) is added to each well and incubated at 37° C. for 30 min. The plates are washed four times with 0.5M Tris buffered Saline (TBS), pH 7.2. 50 μl substrate (ELISA Amplification System Kit, Life Technologies, Inc., Bethesda, Md.) is added to each well and incubated at room temperature for 15 min. Then, 50 μl amplifier (from the same amplification system kit) is added and incubated for another 15 min at room temperature. The reaction is stopped by the addition of 50 μl 0.3M sulphuric acid. The OD at 490 nm of the solution in each well is recorded. To quantitate OP-1 (e.g., Seq. ID No. 5) in culture media, an OP-1 standard curve is performed in parallel with the test samples.

Polyclonal antibody may be prepared as follows. Each rabbit is given a primary immunization of 100 ug/500 μl E. coli produced OP-1 monomer (having an amino acid sequence of residues 328–431 in SEQ ID NO:17) in 0.1% SDS mixed with 500 μl Complete Freund's Adjuvant. The antigen is injected subcutaneously at multiple sites on the back and flanks of the animal. The rabbit is boosted after a month in the same manner using incomplete Freund's Adjuvant. Test bleeds are taken from the ear vein seven days later. Two additional boosts and test bleeds are performed at monthly intervals until antibody against OP-1 (e.g., against the Seq. ID No. 17 polypeptide) is detected in the serum using an ELISA assay. Then, the rabbit is boosted monthly with 100 μg of antigen and bled (15 ml per bleed) at days seven and ten after boosting.

Monoclonal antibody specific for a given morphogen may be prepared as follows. A mouse is given two injections of E. coli produced OP-1 (e.g., Seq. ID No. 17) monomer. The first injection contains 100 μg of OP-1 in complete Freund's adjuvant and is given subcutaneously. The second injection contains 50 μg of OP-1 in incomplete adjuvant and is given intraperitoneally. The mouse then receives a total of 230 μg of OP-1 polypeptide (having the amino acid sequence of residues 307–431 in SEQ ID NO:17) in four intraperitoneal injections at various times over an eight month period. One week prior to fusion, the mouse is boosted intraperitoneally with 100 μg of OP-1 (Seq. ID No. 17, residues 307–431) and 30 μg of the N-terminal peptide ($Ser_{293}$-$Asn_{309}$-Cys) conjugated through the added cysteine to bovine serum albumin with SMCC crosslinking agent. This boost was repeated five days (IP), four days (IP), three days (IP) and one day (IV) prior to fusion. The mouse spleen cells are then fused to myeloma (e.g., 653) cells at a ratio of 1:1 using PEG 1500 (Boeringer Mannheim), and the cell fusion is plated and screened for OP-1-specific antibodies using OP-1 (307–431) as antigen. The cell fusion and monoclonal screening then are according to standard procedures well described in standard texts widely available in the art.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

SEQUENCE LISTING ( 1 ) GENERAL INFORMATION:

( i i i ) NUMBER OF SEQUENCES: 33

( 2 ) INFORMATION FOR SEQ ID NO:1:

( i ) SEQUENCE CHARACTERISTICS:
        ( A ) LENGTH: 97 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..97
        ( D ) OTHER INFORMATION: /label= GENERIC-SEQ-1
            / note= "EACH XAA INDICATES ONE OF THE 20 NATURALLY

OCCURRING L- ISOMER, ALPHA-AMINO ACIDS, OR A DERIVATIVE THEREOF"

( x i ) SEQUENCE DESCRIPTION: SEQ ID NO:1:

| Xaa | Xaa | Xaa | Xaa | Xaa | Xaa | Xaa | Xaa | Xaa | Xaa | Xaa | Xaa | Xaa | Xaa | Xaa | Xaa |
|---|---|---|---|---|---|---|---|---|---|---|---|---|---|---|---|
| 1 | | | | 5 | | | | | | 10 | | | | | 15 |
| Xaa | Xaa | Xaa | Xaa | Xaa | Xaa | Xaa | Xaa | Cys | Xaa | Xaa | Xaa | Cys | Xaa | Xaa | |
| | | | 20 | | | | | 25 | | | | | 30 | | |
| Xaa | Xaa | Xaa | Xaa | Xaa | Xaa | Xaa | Xaa | Xaa | Xaa | Xaa | Xaa | Xaa | Xaa | Xaa | |
| | | 35 | | | | | 40 | | | | | 45 | | | |
| Xaa | Xaa | Xaa | Xaa | Xaa | Xaa | Xaa | Xaa | Xaa | Xaa | Xaa | Cys | Cys | Xaa | Xaa | |
| | 50 | | | | | 55 | | | | | 60 | | | | |
| Xaa | Xaa | Xaa | Xaa | Xaa | Xaa | Xaa | Xaa | Xaa | Xaa | Xaa | Xaa | Xaa | Xaa | Xaa | Xaa |
| 65 | | | | | 70 | | | | | 75 | | | | | 80 |
| Xaa | Xaa | Xaa | Xaa | Xaa | Xaa | Xaa | Xaa | Xaa | Xaa | Xaa | Xaa | Xaa | Cys | Xaa | Cys |
| | | | | 85 | | | | | 90 | | | | | 95 | |
| Xaa | | | | | | | | | | | | | | | |

( 2 ) INFORMATION FOR SEQ ID NO:2:

( i ) SEQUENCE CHARACTERISTICS:
        ( A ) LENGTH: 97 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..97
        ( D ) OTHER INFORMATION: /label= GENERIC-SEQ-2
            / note= "EACH XAA INDICATES ONE OF THE 20 NATURALLY
            OCCURING L- ISOMER, ALPHA-AMINO ACIDS, OR A DERIVATIVE
            THEREOF"

( x i ) SEQUENCE DESCRIPTION: SEQ ID NO:2:

| Xaa | Xaa | Xaa | Xaa | Xaa | Xaa | Xaa | Xaa | Xaa | Xaa | Xaa | Xaa | Xaa | Xaa | Xaa | Xaa |
|---|---|---|---|---|---|---|---|---|---|---|---|---|---|---|---|
| 1 | | | | 5 | | | | | | 10 | | | | | 15 |
| Xaa | Xaa | Xaa | Xaa | Xaa | Xaa | Xaa | Xaa | Cys | Xaa | Xaa | Xaa | Cys | Xaa | Xaa | |
| | | | 20 | | | | | 25 | | | | | 30 | | |
| Xaa | Xaa | Xaa | Cys | Xaa | Xaa | Xaa | Xaa | Xaa | Xaa | Xaa | Xaa | Xaa | Xaa | Xaa | |
| | | 35 | | | | | 40 | | | | | 45 | | | |
| Xaa | Xaa | Xaa | Xaa | Xaa | Xaa | Xaa | Xaa | Xaa | Xaa | Xaa | Cys | Cys | Xaa | Xaa | |
| | 50 | | | | | 55 | | | | | 60 | | | | |
| Xaa | Xaa | Xaa | Xaa | Xaa | Xaa | Xaa | Xaa | Xaa | Xaa | Xaa | Xaa | Xaa | Xaa | Xaa | Xaa |
| 65 | | | | | 70 | | | | | 75 | | | | | 80 |
| Xaa | Xaa | Xaa | Xaa | Xaa | Xaa | Xaa | Xaa | Xaa | Xaa | Xaa | Xaa | Xaa | Cys | Xaa | Cys |
| | | | | 85 | | | | | 90 | | | | | 95 | |
| Xaa | | | | | | | | | | | | | | | |

( 2 ) INFORMATION FOR SEQ ID NO:3:

( i ) SEQUENCE CHARACTERISTICS:
        ( A ) LENGTH: 97 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..97

(D) OTHER INFORMATION: /label= GENERIC-SEQ-3
/ note= "WHEREIN EACH XAA IS INDEPENDENTLY SELECTED FROM
A GROUP OF ONE OR MORE SPECIFIED AMINO ACIDS AS DEFINED
IN THE SPECIFICATION"

(xi) SEQUENCE DESCRIPTION: SEQ ID NO:3:

| Leu | Tyr | Val | Xaa | Phe | Xaa | Xaa | Xaa | Gly | Trp | Xaa | Xaa | Trp | Xaa | Xaa | Ala |
|---|---|---|---|---|---|---|---|---|---|---|---|---|---|---|---|
| 1 | | | | 5 | | | | | 10 | | | | | 15 | |

| Pro | Xaa | Gly | Xaa | Xaa | Ala | Xaa | Tyr | Cys | Xaa | Gly | Xaa | Cys | Xaa | Xaa | Pro |
|---|---|---|---|---|---|---|---|---|---|---|---|---|---|---|---|
| | | | 20 | | | | | 25 | | | | | 30 | | |

| Xaa | Xaa | Xaa | Xaa | Xaa | Xaa | Xaa | Xaa | Asn | His | Ala | Xaa | Xaa | Xaa | Xaa | Leu |
|---|---|---|---|---|---|---|---|---|---|---|---|---|---|---|---|
| | | 35 | | | | | | 40 | | | | 45 | | | |

| Xaa | Xaa | Xaa | Xaa | Xaa | Xaa | Xaa | Xaa | Xaa | Xaa | Xaa | Xaa | Cys | Cys | Xaa | Pro |
|---|---|---|---|---|---|---|---|---|---|---|---|---|---|---|---|
| | 50 | | | | | | 55 | | | | | 60 | | | |

| Xaa | Xaa | Xaa | Xaa | Xaa | Xaa | Xaa | Xaa | Leu | Xaa | Xaa | Xaa | Xaa | Xaa | Xaa | Xaa |
|---|---|---|---|---|---|---|---|---|---|---|---|---|---|---|---|
| 65 | | | | | 70 | | | | | 75 | | | | | 80 |

| Val | Xaa | Leu | Xaa | Xaa | Xaa | Xaa | Xaa | Met | Xaa | Val | Xaa | Xaa | Cys | Gly | Cys |
|---|---|---|---|---|---|---|---|---|---|---|---|---|---|---|---|
| | | | | 85 | | | | | 90 | | | | | 95 | |

Xaa (2) INFORMATION FOR SEQ ID NO:4:

(i) SEQUENCE CHARACTERISTICS:
(A) LENGTH: 102 amino acids
(B) TYPE: amino acid
(C) STRANDEDNESS: single
(D) TOPOLOGY: linear (ii) MOLECULE TYPE: protein (ix) FEATURE:
(A) NAME/KEY: Protein
(B) LOCATION: 1..102
(D) OTHER INFORMATION: /label= GENERIC-SEQ-4
/ note= "WHEREIN EACH XAA IS INDEPENDENTLY SELECTED FROM
A GROUP OF ONE OR MORE SPECIFIED AMINO ACIDS AS DEFINED
IN THE SPECIFICATION"

(xi) SEQUENCE DESCRIPTION: SEQ ID NO:4:

| Cys | Xaa | Xaa | Xaa | Xaa | Leu | Tyr | Val | Xaa | Phe | Xaa | Xaa | Xaa | Gly | Trp | Xaa |
|---|---|---|---|---|---|---|---|---|---|---|---|---|---|---|---|
| 1 | | | | 5 | | | | | 10 | | | | | 15 | |

| Xaa | Trp | Xaa | Xaa | Ala | Pro | Xaa | Gly | Xaa | Xaa | Ala | Xaa | Tyr | Cys | Xaa | Gly |
|---|---|---|---|---|---|---|---|---|---|---|---|---|---|---|---|
| | | | 20 | | | | | 25 | | | | | 30 | | |

| Xaa | Cys | Xaa | Xaa | Pro | Xaa | Xaa | Xaa | Xaa | Xaa | Xaa | Xaa | Xaa | Asn | His | Ala |
|---|---|---|---|---|---|---|---|---|---|---|---|---|---|---|---|
| | | | 35 | | | | | 40 | | | | | 45 | | |

| Xaa | Xaa | Xaa | Xaa | Leu | Xaa | Xaa | Xaa | Xaa | Xaa | Xaa | Xaa | Xaa | Xaa | Xaa | Xaa |
|---|---|---|---|---|---|---|---|---|---|---|---|---|---|---|---|
| | 50 | | | | | | 55 | | | | | 60 | | | |

| Xaa | Cys | Cys | Xaa | Pro | Xaa | Xaa | Xaa | Xaa | Xaa | Xaa | Xaa | Xaa | Leu | Xaa | Xaa |
|---|---|---|---|---|---|---|---|---|---|---|---|---|---|---|---|
| 65 | | | | | 70 | | | | | 75 | | | | | 80 |

| Xaa | Xaa | Xaa | Xaa | Xaa | Val | Xaa | Leu | Xaa | Xaa | Xaa | Xaa | Xaa | Met | Xaa | Val |
|---|---|---|---|---|---|---|---|---|---|---|---|---|---|---|---|
| | | | | 85 | | | | | 90 | | | | | 95 | |

| Xaa | Xaa | Cys | Gly | Cys | Xaa |
|---|---|---|---|---|---|
| | | | 100 | | |

(2) INFORMATION FOR SEQ ID NO:5:

(i) SEQUENCE CHARACTERISTICS:
(A) LENGTH: 139 amino acids
(B) TYPE: amino acid
(C) STRANDEDNESS: single
(D) TOPOLOGY: linear (ii) MOLECULE TYPE: protein ( i x ) FEATURE:
      ( A ) NAME/KEY: Protein
      ( B ) LOCATION: 1..139
      ( D ) OTHER INFORMATION: /note= "HOP-1 (MATURE FORM)"

( x i ) SEQUENCE DESCRIPTION: SEQ ID NO:5:

| Ser 1 | Thr | Gly | Ser | Lys 5 | Gln | Arg | Ser | Gln | Asn 10 | Arg | Ser | Lys | Thr | Pro 15 | Lys |
|---|---|---|---|---|---|---|---|---|---|---|---|---|---|---|---|
| Asn | Gln | Glu | Ala 20 | Leu | Arg | Met | Ala | Asn 25 | Val | Ala | Glu | Asn | Ser 30 | Ser | Ser |
| Asp | Gln | Arg 35 | Gln | Ala | Cys | Lys | Lys 40 | His | Glu | Leu | Tyr | Val 45 | Ser | Phe | Arg |
| Asp | Leu | Gly 50 | Trp | Gln | Asp | Trp 55 | Ile | Ile | Ala | Pro | Glu 60 | Gly | Tyr | Ala | Ala |
| Tyr 65 | Tyr | Cys | Glu | Gly | Glu 70 | Cys | Ala | Phe | Pro | Leu 75 | Asn | Ser | Tyr | Met | Asn 80 |
| Ala | Thr | Asn | His | Ala 85 | Ile | Val | Gln | Thr | Leu 90 | Val | His | Phe | Ile | Asn 95 | Pro |
| Glu | Thr | Val | Pro 100 | Lys | Pro | Cys | Cys | Ala 105 | Pro | Thr | Gln | Leu | Asn 110 | Ala | Ile |
| Ser | Val | Leu 115 | Tyr | Phe | Asp | Asp | Ser 120 | Ser | Asn | Val | Ile | Leu 125 | Lys | Lys | Tyr |
| Arg | Asn | Met 130 | Val | Val | Arg | Ala 135 | Cys | Gly | Cys | His | | | | | |

( 2 ) INFORMATION FOR SEQ ID NO:6:

( i ) SEQUENCE CHARACTERISTICS:
          ( A ) LENGTH: 139 amino acids
          ( B ) TYPE: amino acid
          ( C ) STRANDEDNESS: single
          ( D ) TOPOLOGY: linear ( i i ) MOLECULE TYPE: protein ( i x ) FEATURE:
          ( A ) NAME/KEY: Protein
          ( B ) LOCATION: 1..139
          ( D ) OTHER INFORMATION: /note= "MOP-1 (MATURE FORM)"

( x i ) SEQUENCE DESCRIPTION: SEQ ID NO:6:

| Ser 1 | Thr | Gly | Gly | Lys 5 | Gln | Arg | Ser | Gln | Asn 10 | Arg | Ser | Lys | Thr | Pro 15 | Lys |
|---|---|---|---|---|---|---|---|---|---|---|---|---|---|---|---|
| Asn | Gln | Glu | Ala 20 | Leu | Arg | Met | Ala | Ser 25 | Val | Ala | Glu | Asn | Ser 30 | Ser | Ser |
| Asp | Gln | Arg 35 | Gln | Ala | Cys | Lys | Lys 40 | His | Glu | Leu | Tyr | Val 45 | Ser | Phe | Arg |
| Asp | Leu | Gly 50 | Trp | Gln | Asp | Trp 55 | Ile | Ile | Ala | Pro | Glu 60 | Gly | Tyr | Ala | Ala |
| Tyr 65 | Tyr | Cys | Glu | Gly | Glu 70 | Cys | Ala | Phe | Pro | Leu 75 | Asn | Ser | Tyr | Met | Asn 80 |
| Ala | Thr | Asn | His | Ala 85 | Ile | Val | Gln | Thr | Leu 90 | Val | His | Phe | Ile | Asn 95 | Pro |
| Asp | Thr | Val | Pro 100 | Lys | Pro | Cys | Cys | Ala 105 | Pro | Thr | Gln | Leu | Asn 110 | Ala | Ile |
| Ser | Val | Leu 115 | Tyr | Phe | Asp | Asp | Ser 120 | Ser | Asn | Val | Ile | Leu 125 | Lys | Lys | Tyr |
| Arg | Asn | Met 130 | Val | Val | Arg | Ala 135 | Cys | Gly | Cys | His | | | | | |

( 2 ) INFORMATION FOR SEQ ID NO:7:

( i ) SEQUENCE CHARACTERISTICS:
        ( A ) LENGTH: 139 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..139
        ( D ) OTHER INFORMATION: /note= "HOP-2 (MATURE FORM)"

( x i ) SEQUENCE DESCRIPTION: SEQ ID NO:7:

```
Ala Val Arg Pro Leu Arg Arg Arg Gln Pro Lys Lys Ser Asn Glu Leu
 1               5                  10                  15

Pro Gln Ala Asn Arg Leu Pro Gly Ile Phe Asp Asp Val His Gly Ser
            20                  25                  30

His Gly Arg Gln Val Cys Arg Arg His Glu Leu Tyr Val Ser Phe Gln
        35                  40                  45

Asp Leu Gly Trp Leu Asp Trp Val Ile Ala Pro Gln Gly Tyr Ser Ala
    50                  55                  60

Tyr Tyr Cys Glu Gly Glu Cys Ser Phe Pro Leu Asp Ser Cys Met Asn
65                  70                  75                  80

Ala Thr Asn His Ala Ile Leu Gln Ser Leu Val His Leu Met Lys Pro
                85                  90                  95

Asn Ala Val Pro Lys Ala Cys Cys Ala Pro Thr Lys Leu Ser Ala Thr
            100                 105                 110

Ser Val Leu Tyr Tyr Asp Ser Ser Asn Asn Val Ile Leu Arg Lys His
        115                 120                 125

Arg Asn Met Val Val Lys Ala Cys Gly Cys His
    130                 135
```

( 2 ) INFORMATION FOR SEQ ID NO:8:

( i ) SEQUENCE CHARACTERISTICS:
        ( A ) LENGTH: 139 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..139
        ( D ) OTHER INFORMATION: /note= "MOP-2 (MATURE FORM)"

( x i ) SEQUENCE DESCRIPTION: SEQ ID NO:8:

```
Ala Ala Arg Pro Leu Lys Arg Arg Gln Pro Lys Lys Thr Asn Glu Leu
 1               5                  10                  15

Pro His Pro Asn Lys Leu Pro Gly Ile Phe Asp Asp Gly His Gly Ser
            20                  25                  30

Arg Gly Arg Glu Val Cys Arg Arg His Glu Leu Tyr Val Ser Phe Arg
        35                  40                  45

Asp Leu Gly Trp Leu Asp Trp Val Ile Ala Pro Gln Gly Tyr Ser Ala
    50                  55                  60

Tyr Tyr Cys Glu Gly Glu Cys Ala Phe Pro Leu Asp Ser Cys Met Asn
65                  70                  75                  80

Ala Thr Asn His Ala Ile Leu Gln Ser Leu Val His Leu Met Lys Pro
                85                  90                  95
```

```
Asp  Val  Val  Pro  Lys  Ala  Cys  Cys  Ala  Pro  Thr  Lys  Leu  Ser  Ala  Thr
               100                 105                      110

Ser  Val  Leu  Tyr  Tyr  Asp  Ser  Ser  Asn  Asn  Val  Ile  Leu  Arg  Lys  His
               115                 120                      125

Arg  Asn  Met  Val  Val  Lys  Ala  Cys  Gly  Cys  His
               130                 135
```

(2) INFORMATION FOR SEQ ID NO:9:

(i) SEQUENCE CHARACTERISTICS:
        (A) LENGTH: 101 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..101
        (D) OTHER INFORMATION: /note= "CBMP-2A(FX)"

(xi) SEQUENCE DESCRIPTION: SEQ ID NO:9:

```
Cys  Lys  Arg  His  Pro  Leu  Tyr  Val  Asp  Phe  Ser  Asp  Val  Gly  Trp  Asn
1               5                   10                      15

Asp  Trp  Ile  Val  Ala  Pro  Pro  Gly  Tyr  His

```
                Glu  Tyr  Asp  Lys  Val  Val  Leu  Lys  Asn  Tyr  Gln  Glu  Met  Val  Val  Glu
                                    85                           90                           95

Gly  Cys  Gly  Cys  Arg
                                    100
```

( 2 ) INFORMATION FOR SEQ ID NO:11:

( i ) SEQUENCE CHARACTERISTICS:
        ( A ) LENGTH: 102 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..102
        ( D ) OTHER INFORMATION: /note= "DPP(FX)"

( x i ) SEQUENCE DESCRIPTION: SEQ ID NO:11:

```
                Cys  Arg  Arg  His  Ser  Leu  Tyr  Val  Asp  Phe  Ser  Asp  Val  Gly  Trp  Asp
                1                   5                        10                           15

Asp  Trp  Ile  Val  Ala  Pro  Leu  Gly  Tyr  Asp  Ala  Tyr  Tyr  Cys  His  Gly
                                    20                       25                           30

Lys  Cys  Pro  Phe  Pro  Leu  Ala  Asp  His  Phe  Asn  Ser  Thr  Asn  His  Ala
                               35                            40                      45

Val  Val  Gln  Thr  Leu  Val  Asn  Asn  Asn  Pro  Gly  Lys  Val  Pro  Lys
                          50                       55                      60

Ala  Cys  Cys  Val  Pro  Thr  Gln  Leu  Asp  Ser  Val  Ala  Met  Leu  Tyr  Leu
                65                            70                       75                      80

Asn  Asp  Gln  Ser  Thr  Val  Val  Leu  Lys  Asn  Tyr  Gln  Glu  Met  Thr  Val
                                    85                           90                           95

Val  Gly  Cys  Gly  Cys  Arg
                                    100
```

( 2 ) INFORMATION FOR SEQ ID NO:12:

( i ) SEQUENCE CHARACTERISTICS:
        ( A ) LENGTH: 102 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..102
        ( D ) OTHER INFORMATION: /note= "VGL(FX)"

( x i ) SEQUENCE DESCRIPTION: SEQ ID NO:12:

```
                Cys  Lys  Lys  Arg  His  Leu  Tyr  Val  Glu  Phe  Lys  Asp  Val  Gly  Trp  Gln
                1                   5                        10                           15

Asn  Trp  Val  Ile  Ala  Pro  Gln  Gly  Tyr  Met  Ala  Asn  Tyr  Cys  Tyr  Gly
                                    20                       25                           30

Glu  Cys  Pro  Tyr  Pro  Leu  Thr  Glu  Ile  Leu  Asn  Gly  Ser  Asn  His  Ala
                               35                            40                      45

Ile  Leu  Gln  Thr  Leu  Val  His  Ser  Ile  Glu  Pro  Glu  Asp  Ile  Pro  Leu
                          50                       55                      60

Pro  Cys  Cys  Val  Pro  Thr  Lys  Met  Ser  Pro  Ile  Ser  Met  Leu  Phe  Tyr
                65                            70                       75                      80

Asp  Asn  Asn  Asp  Asn  Val  Val  Leu  Arg  His  Tyr  Glu  Asn  Met  Ala  Val
```

85                          90                          95

Asp  Glu  Cys  Gly  Cys  Arg
                       100

(2) INFORMATION FOR SEQ ID NO:13:

(i) SEQUENCE CHARACTERISTICS:
        (A) LENGTH: 102 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..102
        (D) OTHER INFORMATION: /note= "VGR-1(FX)"

(xi) SEQUENCE DESCRIPTION: SEQ ID NO:13:

Cys  Lys  Lys  His  Glu  Leu  Tyr  Val  Ser  Phe  Gln  Asp  Val  Gly  Trp  Gln
        1                   5                        10                       15

Asp  Trp  Ile  Ile  Ala  Pro  Lys  Gly  Tyr  Ala  Ala  Asn  Tyr  Cys  Asp  Gly
                           20                       25                       30

Glu  Cys  Ser  Phe  Pro  Leu  Asn  Ala  His  Met  Asn  Ala  Thr  Asn  His  Ala
                       35                       40                       45

Ile  Val  Gln  Thr  Leu  Val  His  Val  Met  Asn  Pro  Glu  Tyr  Val  Pro  Lys
        50                                 55                       60

Pro  Cys  Cys  Ala  Pro  Thr  Lys  Val  Asn  Ala  Ile  Ser  Val  Leu  Tyr  Phe
        65                            70                       75                        80

Asp  Asp  Asn  Ser  Asn  Val  Ile  Leu  Lys  Lys  Tyr  Arg  Asn  Met  Val  Val
                            85                            90                       95

Arg  Ala  Cys  Gly  Cys  His
                       100

(2) INFORMATION FOR SEQ ID NO:14:

(i) SEQUENCE CHARACTERISTICS:
        (A) LENGTH: 106 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..106
        (D) OTHER INFORMATION: /note= "GDF-1 (FX)"

(xi) SEQUENCE DESCRIPTION: SEQ ID NO:14:

Cys  Arg  Ala  Arg  Arg  Leu  Tyr  Val  Ser  Phe  Arg  Glu  Val  Gly  Trp  His
        1                   5                        10                       15

Arg  Trp  Val  Ile  Ala  Pro  Arg  Gly  Phe  Leu  Ala  Asn  Tyr  Cys  Gln  Gly
                           20                       25                       30

Gln  Cys  Ala  Leu  Pro  Val  Ala  Leu  Ser  Gly  Ser  Gly  Gly  Pro  Pro  Ala
                       35                       40                       45

Leu  Asn  His  Ala  Val  Leu  Arg  Ala  Leu  Met  His  Ala  Ala  Ala  Pro  Gly
                50                            55                       60

Ala  Ala  Asp  Leu  Pro  Cys  Cys  Val  Pro  Ala  Arg  Leu  Ser  Pro  Ile  Ser
        65                            70                       75                        80

Val  Leu  Phe  Phe  Asp  Asn  Ser  Asp  Asn  Val  Val  Leu  Arg  Gln  Tyr  Glu
                            85                            90                       95

Asp  Met  Val  Val  Asp  Glu  Cys  Gly  Cys  Arg
                                    100                           105

( 2 ) INFORMATION FOR SEQ ID NO:15:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:15:

Cys  Xaa  Xaa  Xaa  Xaa
        1                    5

( 2 ) INFORMATION FOR SEQ ID NO:16:

( i ) SEQUENCE CHARACTERISTICS:
        ( A ) LENGTH: 1822 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 49..1341
        ( D ) OTHER INFORMATION: /product= "HOP-1"

( x i ) SEQUENCE DESCRIPTION: SEQ ID NO:16:

GGTGCGGGCC  CGGAGCCCGG  AGCCCGGGTA  GCGCGTAGAG  CCGGCGCG ATG CAC GTG         57
                                                         Met His Val
                                                         1

CGC TCA CTG CGA GCT GCG GCG CCG CAC AGC TTC GTG GCG CTC TGG GCA            105
Arg Ser Leu Arg Ala Ala Ala Pro His Ser Phe Val Ala Leu Trp Ala
    5               10                  15

CCC CTG TTC CTG CTG CGC TCC GCC CTG GCC GAC TTC AGC CTG GAC AAC            153
Pro Leu Phe Leu Leu Arg Ser Ala Leu Ala Asp Phe Ser Leu Asp Asn
20              25                  30                  35

GAG GTG CAC TCG AGC TTC ATC CAC CGG CGC CTC CGC AGC CAG GAG CGG            201
Glu Val His Ser Ser Phe Ile His Arg Arg Leu Arg Ser Gln Glu Arg
            40                  45                  50

CGG GAG ATG CAG CGC GAG ATC CTC TCC ATT TTG GGC TTG CCC CAC CGC            249
Arg Glu Met Gln Arg Glu Ile Leu Ser Ile Leu Gly Leu Pro His Arg
                55                  60                  65

CCG CGC CCG CAC CTC CAG GGC AAG CAC AAC TCG GCA CCC ATG TTC ATG            297
Pro Arg Pro His Leu Gln Gly Lys His Asn Ser Ala Pro Met Phe Met
        70                  75                  80

CTG GAC CTG TAC AAC GCC ATG GCG GTG GAG GAG GGC GGC GGG CCC GGC            345
Leu Asp Leu Tyr Asn Ala Met Ala Val Glu Glu Gly Gly Gly Pro Gly
    85                  90                  95

GGC CAG GGC TTC TCC TAC CCC TAC AAG GCC GTC TTC AGT ACC CAG GGC            393
Gly Gln Gly Phe Ser Tyr Pro Tyr Lys Ala Val Phe Ser Thr Gln Gly
100             105                 110                 115

CCC CCT CTG GCC AGC CTG CAA GAT AGC CAT TTC CTC ACC GAC GCC GAC            441
Pro Pro Leu Ala Ser Leu Gln Asp Ser His Phe Leu Thr Asp Ala Asp
            120                 125                 130

ATG GTC ATG AGC TTC GTC AAC CTC GTG GAA CAT GAC AAG GAA TTC TTC            489
Met Val Met Ser Phe Val Asn Leu Val Glu His Asp Lys Glu Phe Phe
                135                 140                 145

CAC CCA CGC TAC CAC CAT CGA GAG TTC CGG TTT GAT CTT TCC AAG ATC            537
His Pro Arg Tyr His His Arg Glu Phe Arg Phe Asp Leu Ser Lys Ile
        150                 155                 160

| | | | | | | | | | | | | | | | | |
|---|---|---|---|---|---|---|---|---|---|---|---|---|---|---|---|---|
| CCA | GAA | GGG | GAA | GCT | GTC | ACG | GCA | GCC | GAA | TTC | CGG | ATC | TAC | AAG | GAC | 585 |
| Pro | Glu | Gly | Glu | Ala | Val | Thr | Ala | Ala | Glu | Phe | Arg | Ile | Tyr | Lys | Asp | |
| 165 | | | | | 170 | | | | | | 175 | | | | | |
| TAC | ATC | CGG | GAA | CGC | TTC | GAC | AAT | GAG | ACG | TTC | CGG | ATC | AGC | GTT | TAT | 633 |
| Tyr | Ile | Arg | Glu | Arg | Phe | Asp | Asn | Glu | Thr | Phe | Arg | Ile | Ser | Val | Tyr | |
| 180 | | | | | 185 | | | | | 190 | | | | | 195 | |
| CAG | GTG | CTC | CAG | GAG | CAC | TTG | GGC | AGG | GAA | TCG | GAT | CTC | TTC | CTG | CTC | 681 |
| Gln | Val | Leu | Gln | Glu | His | Leu | Gly | Arg | Glu | Ser | Asp | Leu | Phe | Leu | Leu | |
| | | | | 200 | | | | | 205 | | | | | 210 | | |
| GAC | AGC | CGT | ACC | CTC | TGG | GCC | TCG | GAG | GAG | GGC | TGG | CTG | GTG | TTT | GAC | 729 |
| Asp | Ser | Arg | Thr | Leu | Trp | Ala | Ser | Glu | Glu | Gly | Trp | Leu | Val | Phe | Asp | |
| | | | 215 | | | | | 220 | | | | | 225 | | | |
| ATC | ACA | GCC | ACC | AGC | AAC | CAC | TGG | GTG | GTC | AAT | CCG | CGG | CAC | AAC | CTG | 777 |
| Ile | Thr | Ala | Thr | Ser | Asn | His | Trp | Val | Val | Asn | Pro | Arg | His | Asn | Leu | |
| | | | 230 | | | | | 235 | | | | | 240 | | | |
| GGC | CTG | CAG | CTC | TCG | GTG | GAG | ACG | CTG | GAT | GGG | CAG | AGC | ATC | AAC | CCC | 825 |
| Gly | Leu | Gln | Leu | Ser | Val | Glu | Thr | Leu | Asp | Gly | Gln | Ser | Ile | Asn | Pro | |
| | | 245 | | | | | 250 | | | | | 255 | | | | |
| AAG | TTG | GCG | GGC | CTG | ATT | GGG | CGG | CAC | GGG | CCC | CAG | AAC | AAG | CAG | CCC | 873 |
| Lys | Leu | Ala | Gly | Leu | Ile | Gly | Arg | His | Gly | Pro | Gln | Asn | Lys | Gln | Pro | |
| 260 | | | | | 265 | | | | | 270 | | | | | 275 | |
| TTC | ATG | GTG | GCT | TTC | TTC | AAG | GCC | ACG | GAG | GTC | CAC | TTC | CGC | AGC | ATC | 921 |
| Phe | Met | Val | Ala | Phe | Phe | Lys | Ala | Thr | Glu | Val | His | Phe | Arg | Ser | Ile | |
| | | | | 280 | | | | | 285 | | | | | 290 | | |
| CGG | TCC | ACG | GGG | AGC | AAA | CAG | CGC | AGC | CAG | AAC | CGC | TCC | AAG | ACG | CCC | 969 |
| Arg | Ser | Thr | Gly | Ser | Lys | Gln | Arg | Ser | Gln | Asn | Arg | Ser | Lys | Thr | Pro | |
| | | | 295 | | | | | 300 | | | | | 305 | | | |
| AAG | AAC | CAG | GAA | GCC | CTG | CGG | ATG | GCC | AAC | GTG | GCA | GAG | AAC | AGC | AGC | 1017 |
| Lys | Asn | Gln | Glu | Ala | Leu | Arg | Met | Ala | Asn | Val | Ala | Glu | Asn | Ser | Ser | |
| | | 310 | | | | | 315 | | | | | 320 | | | | |
| AGC | GAC | CAG | AGG | CAG | GCC | TGT | AAG | AAG | CAC | GAG | CTG | TAT | GTC | AGC | TTC | 1065 |
| Ser | Asp | Gln | Arg | Gln | Ala | Cys | Lys | Lys | His | Glu | Leu | Tyr | Val | Ser | Phe | |
| 325 | | | | | 330 | | | | | 335 | | | | | | |
| CGA | GAC | CTG | GGC | TGG | CAG | GAC | TGG | ATC | ATC | GCG | CCT | GAA | GGC | TAC | GCC | 1113 |
| Arg | Asp | Leu | Gly | Trp | Gln | Asp | Trp | Ile | Ile | Ala | Pro | Glu | Gly | Tyr | Ala | |
| 340 | | | | | 345 | | | | | 350 | | | | | 355 | |
| GCC | TAC | TAC | TGT | GAG | GGG | GAG | TGT | GCC | TTC | CCT | CTG | AAC | TCC | TAC | ATG | 1161 |
| Ala | Tyr | Tyr | Cys | Glu | Gly | Glu | Cys | Ala | Phe | Pro | Leu | Asn | Ser | Tyr | Met | |
| | | | | 360 | | | | | 365 | | | | | 370 | | |
| AAC | GCC | ACC | AAC | CAC | GCC | ATC | GTG | CAG | ACG | CTG | GTC | CAC | TTC | ATC | AAC | 1209 |
| Asn | Ala | Thr | Asn | His | Ala | Ile | Val | Gln | Thr | Leu | Val | His | Phe | Ile | Asn | |
| | | | 375 | | | | | 380 | | | | | 385 | | | |
| CCG | GAA | ACG | GTG | CCC | AAG | CCC | TGT | TGT | GCG | CCC | ACG | CAG | CTC | AAT | GCC | 1257 |
| Pro | Glu | Thr | Val | Pro | Lys | Pro | Cys | Cys | Ala | Pro | Thr | Gln | Leu | Asn | Ala | |
| | | 390 | | | | | 395 | | | | | 400 | | | | |
| ATC | TCC | GTC | CTC | TAC | TTC | GAT | GAC | AGC | TCC | AAC | GTC | ATC | CTG | AAG | AAA | 1305 |
| Ile | Ser | Val | Leu | Tyr | Phe | Asp | Asp | Ser | Ser | Asn | Val | Ile | Leu | Lys | Lys | |
| | 405 | | | | | 410 | | | | | 415 | | | | | |
| TAC | AGA | AAC | ATG | GTG | GTC | CGG | GCC | TGT | GGC | TGC | CAC | TAGCTCCTCC | | | | 1351 |
| Tyr | Arg | Asn | Met | Val | Val | Arg | Ala | Cys | Gly | Cys | His | | | | | |
| 420 | | | | 425 | | | | | 430 | | | | | | | |

| | |
|---|---|
| GAGAATTCAG ACCCTTTGGG GCCAAGTTTT TCTGGATCCT CCATTGCTCG CCTTGGCCAG | 1411 |
| GAACCAGCAG ACCAACTGCC TTTTGTGAGA CCTTCCCCTC CCTATCCCCA ACTTTAAAGG | 1471 |
| TGTGAGAGTA TTAGGAAACA TGAGCAGCAT ATGGCTTTTG ATCAGTTTTT CAGTGGCAGC | 1531 |
| ATCCAATGAA CAAGATCCTA CAAGCTGTGC AGGCAAAACC TAGCAGGAAA AAAAAACAAC | 1591 |
| GCATAAAGAA AAATGGCCGG GCCAGGTCAT TGGCTGGGAA GTCTCAGCCA TGCACGGACT | 1651 |
| CGTTTCCAGA GGTAATTATG AGCGCCTACC AGCCAGGCCA CCCAGCCGTG GGAGGAAGGG | 1711 |

```
GGCGTGGCAA GGGGTGGGCA CATTGGTGTC TGTGCGAAAG GAAAATTGAC CCGGAAGTTC        1771

CTGTAATAAA TGTCACAATA AACGAATGA ATGAAAAAAA AAAAAAAAA A                   1822
```

( 2 ) INFORMATION FOR SEQ ID NO:17:

( i ) SEQUENCE CHARACTERISTICS:
        ( A ) LENGTH: 431 amino acids
        ( B ) TYPE: amino acid
        ( D ) TOPOLOGY: linear ( i i ) MOLECULE TYPE: protein ( x i ) SEQUENCE DESCRIPTION: SEQ ID NO:17:

```
Met His Val Arg Ser Leu Arg Ala Ala Ala Pro His Ser Phe Val Ala
 1           5                  10                  15

Leu Trp Ala Pro Leu Phe Leu Leu Arg Ser Ala Leu Ala Asp Phe Ser
            20                  25                  30

Leu Asp Asn Glu Val His Ser Ser Phe Ile His Arg Arg Leu Arg Ser
         35                  40                  45

Gln Glu Arg Arg Glu Met Gln Arg Glu Ile Leu Ser Ile Leu Gly Leu
 50                  55                  60

Pro His Arg Pro Arg Pro His Leu Gln Gly Lys His Asn Ser Ala Pro
 65                  70                  75                  80

Met Phe Met Leu Asp Leu Tyr Asn Ala Met Ala Val Glu Glu Gly Gly
            85                  90                  95

Gly Pro Gly Gly Gln Gly Phe Ser Tyr Pro Tyr Lys Ala Val Phe Ser
            100                 105                 110

Thr Gln Gly Pro Pro Leu Ala Ser Leu Gln Asp Ser His Phe Leu Thr
         115                 120                 125

Asp Ala Asp Met Val Met Ser Phe Val Asn Leu Val Glu His Asp Lys
130                 135                 140

Glu Phe Phe His Pro Arg Tyr His His Arg Glu Phe Arg Phe Asp Leu
145                 150                 155                 160

Ser Lys Ile Pro Glu Gly Glu Ala Val Thr Ala Ala Glu Phe Arg Ile
            165                 170                 175

Tyr Lys Asp Tyr Ile Arg Glu Arg Phe Asp Asn Glu Thr Phe Arg Ile
            180                 185                 190

Ser Val Tyr Gln Val Leu Gln Glu His Leu Gly Arg Glu Ser Asp Leu
         195                 200                 205

Phe Leu Leu Asp Ser Arg Thr Leu Trp Ala Ser Glu Gly Trp Leu
210                 215                 220

Val Phe Asp Ile Thr Ala Thr Ser Asn His Trp Val Val Asn Pro Arg
225                 230                 235                 240

His Asn Leu Gly Leu Gln Leu Ser Val Glu Thr Leu Asp Gly Gln Ser
            245                 250                 255

Ile Asn Pro Lys Leu Ala Gly Leu Ile Gly Arg His Gly Pro Gln Asn
            260                 265                 270

Lys Gln Pro Phe Met Val Ala Phe Phe Lys Ala Thr Glu Val His Phe
         275                 280                 285

Arg Ser Ile Arg Ser Thr Gly Ser Lys Gln Arg Ser Gln Asn Arg Ser
290                 295                 300

Lys Thr Pro Lys Asn Gln Glu Ala Leu Arg Met Ala Asn Val Ala Glu
305                 310                 315                 320

Asn Ser Ser Ser Asp Gln Arg Gln Ala Cys Lys Lys His Glu Leu Tyr
            325                 330                 335
```

```
Val  Ser  Phe  Arg  Asp  Leu  Gly  Trp  Gln  Asp  Trp  Ile  Ile  Ala  Pro  Glu
               340                 345                      350

Gly  Tyr  Ala  Ala  Tyr  Tyr  Cys  Glu  Gly  Glu  Cys  Ala  Phe  Pro  Leu  Asn
          355                      360                      365

Ser  Tyr  Met  Asn  Ala  Thr  Asn  His  Ala  Ile  Val  Gln  Thr  Leu  Val  His
     370                      375                 380

Phe  Ile  Asn  Pro  Glu  Thr  Val  Pro  Lys  Pro  Cys  Cys  Ala  Pro  Thr  Gln
385                      390                 395                           400

Leu  Asn  Ala  Ile  Ser  Val  Leu  Tyr  Phe  Asp  Asp  Ser  Ser  Asn  Val  Ile
               405                      410                           415

Leu  Lys  Lys  Tyr  Arg  Asn  Met  Val  Val  Arg  Ala  Cys  Gly  Cys  His
               420                      425                      430
```

( 2 ) INFORMATION FOR SEQ ID NO:18:

( i ) SEQUENCE CHARACTERISTICS:
        ( A ) LENGTH: 1873 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 104..1393
        ( D ) OTHER INFORMATION: /product= "MOP1 (CDNA)"

( x i ) SEQUENCE DESCRIPTION: SEQ ID NO:18:

```
CTGCAGCAAG  TGACCTCGGG  TCGTGGACCG  CTGCCCTGCC  CCCTCCGCTG  CCACCTGGGG          60

CGGCGCGGGC  CCGGTGCCCC  GGATCGCGCG  TAGAGCCGGC  GCG  ATG  CAC  GTG  CGC         115
                                                  Met  His  Val  Arg
                                                   1

TCG  CTG  CGC  GCT  GCG  GCG  CCA  CAC  AGC  TTC  GTG  GCG  CTC  TGG  GCG  CCT  163
Ser  Leu  Arg  Ala  Ala  Ala  Pro  His  Ser  Phe  Val  Ala  Leu  Trp  Ala  Pro
 5                        10                      15                       20

CTG  TTC  TTG  CTG  CGC  TCC  GCC  CTG  GCC  GAT  TTC  AGC  CTG  GAC  AAC  GAG  211
Leu  Phe  Leu  Leu  Arg  Ser  Ala  Leu  Ala  Asp  Phe  Ser  Leu  Asp  Asn  Glu
                    25                       30                       35

GTG  CAC  TCC  AGC  TTC  ATC  CAC  CGG  CGC  CTC  CGC  AGC  CAG  GAG  CGG  CGG  259
Val  His  Ser  Ser  Phe  Ile  His  Arg  Arg  Leu  Arg  Ser  Gln  Glu  Arg  Arg
               40                       45                       50

GAG  ATG  CAG  CGG  GAG  ATC  CTG  TCC  ATC  TTA  GGG  TTG  CCC  CAT  CGC  CCG  307
Glu  Met  Gln  Arg  Glu  Ile  Leu  Ser  Ile  Leu  Gly  Leu  Pro  His  Arg  Pro
          55                       60                       65

CGC  CCG  CAC  CTC  CAG  GGA  AAG  CAT  AAT  TCG  GCG  CCC  ATG  TTC  ATG  TTG  355
Arg  Pro  His  Leu  Gln  Gly  Lys  His  Asn  Ser  Ala  Pro  Met  Phe  Met  Leu
      70                      75                       80

GAC  CTG  TAC  AAC  GCC  ATG  GCG  GTG  GAG  GAG  AGC  GGG  CCG  GAC  GGA  CAG  403
Asp  Leu  Tyr  Asn  Ala  Met  Ala  Val  Glu  Glu  Ser  Gly  Pro  Asp  Gly  Gln
 85                      90                       95                       100

GGC  TTC  TCC  TAC  CCC  TAC  AAG  GCC  GTC  TTC  AGT  ACC  CAG  GGC  CCC  CCT  451
Gly  Phe  Ser  Tyr  Pro  Tyr  Lys  Ala  Val  Phe  Ser  Thr  Gln  Gly  Pro  Pro
                    105                      110                      115

TTA  GCC  AGC  CTG  CAG  GAC  AGC  CAT  TTC  CTC  ACT  GAC  GCC  GAC  ATG  GTC  499
Leu  Ala  Ser  Leu  Gln  Asp  Ser  His  Phe  Leu  Thr  Asp  Ala  Asp  Met  Val
               120                      125                      130

ATG  AGC  TTC  GTC  AAC  CTA  GTG  GAA  CAT  GAC  AAA  GAA  TTC  TTC  CAC  CCT  547
Met  Ser  Phe  Val  Asn  Leu  Val  Glu  His  Asp  Lys  Glu  Phe  Phe  His  Pro
          135                      140                      145

CGA  TAC  CAC  CAT  CGG  GAG  TTC  CGG  TTT  GAT  CTT  TCC  AAG  ATC  CCC  GAG  595
Arg  Tyr  His  His  Arg  Glu  Phe  Arg  Phe  Asp  Leu  Ser  Lys  Ile  Pro  Glu
```

-continued

```
                 150                           155                           160
GGC   GAA   CGG   GTG   ACC   GCA   GCC   GAA   TTC   AGG   ATC   TAT   AAG   GAC   TAC   ATC        643
Gly   Glu   Arg   Val   Thr   Ala   Ala   Glu   Phe   Arg   Ile   Tyr   Lys   Asp   Tyr   Ile
165                     170                           175                           180

CGG   GAG   CGA   TTT   GAC   AAC   GAG   ACC   TTC   CAG   ATC   ACA   GTC   TAT   CAG   GTG        691
Arg   Glu   Arg   Phe   Asp   Asn   Glu   Thr   Phe   Gln   Ile   Thr   Val   Tyr   Gln   Val
                        185                           190                           195

CTC   CAG   GAG   CAC   TCA   GGC   AGG   GAG   TCG   GAC   CTC   TTC   TTG   CTG   GAC   AGC        739
Leu   Gln   Glu   His   Ser   Gly   Arg   Glu   Ser   Asp   Leu   Phe   Leu   Leu   Asp   Ser
                  200                           205                           210

CGC   ACC   ATC   TGG   GCT   TCT   GAG   GAG   GGC   TGG   TTG   GTG   TTT   GAT   ATC   ACA        787
Arg   Thr   Ile   Trp   Ala   Ser   Glu   Glu   Gly   Trp   Leu   Val   Phe   Asp   Ile   Thr
            215                           220                           225

GCC   ACC   AGC   AAC   CAC   TGG   GTG   GTC   AAC   CCT   CGG   CAC   AAC   CTG   GGC   TTA        835
Ala   Thr   Ser   Asn   His   Trp   Val   Val   Asn   Pro   Arg   His   Asn   Leu   Gly   Leu
      230                           235                           240

CAG   CTC   TCT   GTG   GAG   ACC   CTG   GAT   GGG   CAG   AGC   ATC   AAC   CCC   AAG   TTG        883
Gln   Leu   Ser   Val   Glu   Thr   Leu   Asp   Gly   Gln   Ser   Ile   Asn   Pro   Lys   Leu
245                           250                           255                           260

GCA   GGC   CTG   ATT   GGA   CGG   CAT   GGA   CCC   CAG   AAC   AAG   CAA   CCC   TTC   ATG        931
Ala   Gly   Leu   Ile   Gly   Arg   His   Gly   Pro   Gln   Asn   Lys   Gln   Pro   Phe   Met
                              265                           270                           275

GTG   GCC   TTC   TTC   AAG   GCC   ACG   GAA   GTC   CAT   CTC   CGT   AGT   ATC   CGG   TCC        979
Val   Ala   Phe   Phe   Lys   Ala   Thr   Glu   Val   His   Leu   Arg   Ser   Ile   Arg   Ser
                  280                           285                           290

ACG   GGG   GGC   AAG   CAG   CGC   AGC   CAG   AAT   CGC   TCC   AAG   ACG   CCA   AAG   AAC       1027
Thr   Gly   Gly   Lys   Gln   Arg   Ser   Gln   Asn   Arg   Ser   Lys   Thr   Pro   Lys   Asn
            295                           300                           305

CAA   GAG   GCC   CTG   AGG   ATG   GCC   AGT   GTG   GCA   GAA   AAC   AGC   AGC   AGT   GAC       1075
Gln   Glu   Ala   Leu   Arg   Met   Ala   Ser   Val   Ala   Glu   Asn   Ser   Ser   Ser   Asp
      310                           315                           320

CAG   AGG   CAG   GCC   TGC   AAG   AAA   CAT   GAG   CTG   TAC   GTC   AGC   TTC   CGA   GAC       1123
Gln   Arg   Gln   Ala   Cys   Lys   Lys   His   Glu   Leu   Tyr   Val   Ser   Phe   Arg   Asp
325                           330                           335                           340

CTT   GGC   TGG   CAG   GAC   TGG   ATC   ATT   GCA   CCT   GAA   GGC   TAT   GCT   GCC   TAC       1171
Leu   Gly   Trp   Gln   Asp   Trp   Ile   Ile   Ala   Pro   Glu   Gly   Tyr   Ala   Ala   Tyr
                              345                           350                           355

TAC   TGT   GAG   GGA   GAG   TGC   GCC   TTC   CCT   CTG   AAC   TCC   TAC   ATG   AAC   GCC       1219
Tyr   Cys   Glu   Gly   Glu   Cys   Ala   Phe   Pro   Leu   Asn   Ser   Tyr   Met   Asn   Ala
                  360                           365                           370

ACC   AAC   CAC   GCC   ATC   GTC   CAG   ACA   CTG   GTT   CAC   TTC   ATC   AAC   CCA   GAC       1267
Thr   Asn   His   Ala   Ile   Val   Gln   Thr   Leu   Val   His   Phe   Ile   Asn   Pro   Asp
            375                           380                           385

ACA   GTA   CCC   AAG   CCC   TGC   TGT   GCG   CCC   ACC   CAG   CTC   AAC   GCC   ATC   TCT       1315
Thr   Val   Pro   Lys   Pro   Cys   Cys   Ala   Pro   Thr   Gln   Leu   Asn   Ala   Ile   Ser
      390                           395                           400

GTC   CTC   TAC   TTC   GAC   GAC   AGC   TCT   AAT   GTC   ATC   CTG   AAG   AAG   TAC   AGA       1363
Val   Leu   Tyr   Phe   Asp   Asp   Ser   Ser   Asn   Val   Ile   Leu   Lys   Lys   Tyr   Arg
405                           410                           415                           420

AAC   ATG   GTG   GTC   CGG   GCC   TGT   GGC   TGC   CAC   TAGCTCTTCC   TGAGACCCTG                 1413
Asn   Met   Val   Val   Arg   Ala   Cys   Gly   Cys   His
                        425                           430

ACCTTTGCGG   GGCCACACCT   TTCCAAATCT   TCGATGTCTC   ACCATCTAAG   TCTCTCACTG                         1473

CCCACCTTGG   CGAGGAGAAC   AGACCAACCT   CTCCTGAGCC   TTCCCTCACC   TCCCAACCGG                         1533

AAGCATGTAA   GGGTTCCAGA   AACCTGAGCG   TGCAGCAGCT   GATGAGCGCC   CTTTCCTTCT                         1593

GGCACGTGAC   GGACAAGATC   CTACCAGCTA   CCACAGCAAA   CGCCTAAGAG   CAGGAAAAAT                         1653

GTCTGCCAGG   AAAGTGTCCA   GTGTCCACAT   GGCCCCTGGC   GCTCTGAGTC   TTTGAGGAGT                         1713
```

| AATCGCAAGC | CTCGTTCAGC | TGCAGCAGAA | GGAAGGGCTT | AGCCAGGGTG | GGCGCTGGCG | 1773 |
| TCTGTGTTGA | AGGGAAACCA | AGCAGAAGCC | ACTGTAATGA | TATGTCACAA | TAAAACCCAT | 1833 |
| GAATGAAAAA | AAAAAAAAAA | AAAAAAAAAA | AAAAGAATTC | | | 1873 |

( 2 ) INFORMATION FOR SEQ ID NO:19:

( i ) SEQUENCE CHARACTERISTICS:
        ( A ) LENGTH: 430 amino acids
        ( B ) TYPE: amino acid
        ( D ) TOPOLOGY: linear ( i i ) MOLECULE TYPE: protein ( x i ) SEQUENCE DESCRIPTION: SEQ ID NO:19:

```
Met His Val Arg Ser Leu Arg Ala Ala Pro His Ser Phe Val Ala
  1               5                  10                 15

Leu Trp Ala Pro Leu Phe Leu Leu Arg Ser Ala Leu Ala Asp Phe Ser
                 20                 25                 30

Leu Asp Asn Glu Val His Ser Ser Phe Ile His Arg Arg Leu Arg Ser
             35                 40                 45

Gln Glu Arg Arg Glu Met Gln Arg Glu Ile Leu Ser Ile Leu Gly Leu
     50                 55                 60

Pro His Arg Pro Arg Pro His Leu Gln Gly Lys His Asn Ser Ala Pro
 65                 70                 75                 80

Met Phe Met Leu Asp Leu Tyr Asn Ala Met Ala Val Glu Glu Ser Gly
                 85                 90                 95

Pro Asp Gly Gln Gly Phe Ser Tyr Pro Tyr Lys Ala Val Phe Ser Thr
                100                105                110

Gln Gly Pro Pro Leu Ala Ser Leu Gln Asp Ser His Phe Leu Thr Asp
            115                120                125

Ala Asp Met Val Met Ser Phe Val Asn Leu Val Glu His Asp Lys Glu
130                135                140

Phe Phe His Pro Arg Tyr His Arg Glu Phe Arg Phe Asp Leu Ser
145                150                155                160

Lys Ile Pro Glu Gly Glu Arg Val Thr Ala Ala Glu Phe Arg Ile Tyr
                165                170                175

Lys Asp Tyr Ile Arg Glu Arg Phe Asp Asn Glu Thr Phe Gln Ile Thr
            180                185                190

Val Tyr Gln Val Leu Gln Glu His Ser Gly Arg Glu Ser Asp Leu Phe
    195                200                205

Leu Leu Asp Ser Arg Thr Ile Trp Ala Ser Glu Glu Gly Trp Leu Val
210                215                220

Phe Asp Ile Thr Ala Thr Ser Asn His Trp Val Val Asn Pro Arg His
225                230                235                240

Asn Leu Gly Leu Gln Leu Ser Val Glu Thr Leu Asp Gly Gln Ser Ile
                245                250                255

Asn Pro Lys Leu Ala Gly Leu Ile Gly Arg His Gly Pro Gln Asn Lys
            260                265                270

Gln Pro Phe Met Val Ala Phe Phe Lys Ala Thr Glu Val His Leu Arg
        275                280                285

Ser Ile Arg Ser Thr Gly Gly Lys Gln Arg Ser Gln Asn Arg Ser Lys
    290                295                300

Thr Pro Lys Asn Gln Glu Ala Leu Arg Met Ala Ser Val Ala Glu Asn
305                310                315                320

Ser Ser Ser Asp Gln Arg Gln Ala Cys Lys Lys His Glu Leu Tyr Val
            325                330                335
```

```
Ser  Phe  Arg  Asp  Leu  Gly  Trp  Gln  Asp  Trp  Ile  Ile  Ala  Pro  Glu  Gly
               340                      345                         350

Tyr  Ala  Ala  Tyr  Tyr  Cys  Glu  Gly  Glu  Cys  Ala  Phe  Pro  Leu  Asn  Ser
          355                      360                         365

Tyr  Met  Asn  Ala  Thr  Asn  His  Ala  Ile  Val  Gln  Thr  Leu  Val  His  Phe
     370                      375                    380

Ile  Asn  Pro  Asp  Thr  Val  Pro  Lys  Pro  Cys  Cys  Ala  Pro  Thr  Gln  Leu
385                      390                    395                         400

Asn  Ala  Ile  Ser  Val  Leu  Tyr  Phe  Asp  Asp  Ser  Ser  Asn  Val  Ile  Leu
               405                      410                         415

Lys  Lys  Tyr  Arg  Asn  Met  Val  Val  Arg  Ala  Cys  Gly  Cys  His
               420                      425                    430
```

( 2 ) INFORMATION FOR SEQ ID NO:20:

( i ) SEQUENCE CHARACTERISTICS:
        ( A ) LENGTH: 1723 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 490..1695

( x i ) SEQUENCE DESCRIPTION: SEQ ID NO:20:

```
GGCGCCGGCA  GAGCAGGAGT  GGCTGGAGGA  GCTGTGGTTG  GAGCAGGAGG  TGGCACGGCA        60

GGGCTGGAGG  GCTCCCTATG  AGTGGCGGAG  ACGGCCCAGG  AGGCGCTGGA  GCAACAGCTC       120

CCACACCGCA  CCAAGCGGTG  GCTGCAGGAG  CTCGCCCATC  GCCCCTGCGC  TGCTCGGACC       180

GCGGCCACAG  CCGGACTGGC  GGGTACGGCG  GCGACAGAGG  CATTGGCCGA  GAGTCCCAGT       240

CCGCAGAGTA  GCCCCGGCCT  CGAGGCGGTG  GCGTCCCGGT  CCTCTCCGTC  CAGGAGCCAG       300

GACAGGTGTC  GCGCGGCGGG  GCTCCAGGGA  CCGCGCCTGA  GGCCGGCTGC  CCGCCCGTCC       360

CGCCCCGCCC  CGCCGCCCGC  CGCCCGCCGA  GCCCAGCCTC  CTTGCCGTCG  GGGCGTCCCC       420

AGGCCCTGGG  TCGGCCGCGG  AGCCGATGCG  CGCCCGCTGA  GCGCCCAGC   TGAGCGCCCC       480

CGGCCTGCC  ATG  ACC  GCG  CTC  CCC  GGC  CCG  CTC  TGG  CTC  CTG  GGC  CTG       528
           Met  Thr  Ala  Leu  Pro  Gly  Pro  Leu  Trp  Leu  Leu  Gly  Leu
             1                 5                         10

GCG  CTA  TGC  GCG  CTG  GGC  GGG  GGC  GGC  CCC  GGC  CTG  CGA  CCC  CCG  CCC    576
Ala  Leu  Cys  Ala  Leu  Gly  Gly  Gly  Gly  Pro  Gly  Leu  Arg  Pro  Pro  Pro
          15                      20                         25

GGC  TGT  CCC  CAG  CGA  CGT  CTG  GGC  GCG  CGC  GAG  CGC  CGG  GAC  GTG  CAG    624
Gly  Cys  Pro  Gln  Arg  Arg  Leu  Gly  Ala  Arg  Glu  Arg  Arg  Asp  Val  Gln
30                           35                      40                       45

CGC  GAG  ATC  CTG  GCG  GTG  CTC  GGG  CTG  CCT  GGG  CGG  CCC  CGG  CCC  CGC    672
Arg  Glu  Ile  Leu  Ala  Val  Leu  Gly  Leu  Pro  Gly  Arg  Pro  Arg  Pro  Arg
                    50                      55                         60

GCG  CCA  CCC  GCC  GCC  TCC  CGG  CTG  CCC  GCG  TCC  GCG  CCG  CTC  TTC  ATG    720
Ala  Pro  Pro  Ala  Ala  Ser  Arg  Leu  Pro  Ala  Ser  Ala  Pro  Leu  Phe  Met
          65                      70                         75

CTG  GAC  CTG  TAC  CAC  GCC  ATG  GCC  GGC  GAC  GAC  GAC  GAG  GAC  GGC  GCG    768
Leu  Asp  Leu  Tyr  His  Ala  Met  Ala  Gly  Asp  Asp  Asp  Glu  Asp  Gly  Ala
               80                      85                         90

CCC  GCG  GAG  CGG  CGC  CTG  GGC  CGC  GCC  GAC  CTG  GTC  ATG  AGC  TTC  GTT    816
Pro  Ala  Glu  Arg  Arg  Leu  Gly  Arg  Ala  Asp  Leu  Val  Met  Ser  Phe  Val
          95                      100                        105
```

| | | | | | | | | | | | | | | | | |
|---|---|---|---|---|---|---|---|---|---|---|---|---|---|---|---|---|
| AAC | ATG | GTG | GAG | CGA | GAC | CGT | GCC | CTG | GGC | CAC | CAG | GAG | CCC | CAT | TGG | 864 |
| Asn | Met | Val | Glu | Arg | Asp | Arg | Ala | Leu | Gly | His | Gln | Glu | Pro | His | Trp | |
| 110 | | | | 115 | | | | | 120 | | | | | | 125 | |
| AAG | GAG | TTC | CGC | TTT | GAC | CTG | ACC | CAG | ATC | CCG | GCT | GGG | GAG | GCG | GTC | 912 |
| Lys | Glu | Phe | Arg | Phe | Asp | Leu | Thr | Gln | Ile | Pro | Ala | Gly | Glu | Ala | Val | |
| | | | | 130 | | | | 135 | | | | | | 140 | | |
| ACA | GCT | GCG | GAG | TTC | CGG | ATT | TAC | AAG | GTG | CCC | AGC | ATC | CAC | CTG | CTC | 960 |
| Thr | Ala | Ala | Glu | Phe | Arg | Ile | Tyr | Lys | Val | Pro | Ser | Ile | His | Leu | Leu | |
| | | | 145 | | | | | 150 | | | | | 155 | | | |
| AAC | AGG | ACC | CTC | CAC | GTC | AGC | ATG | TTC | CAG | GTG | GTC | CAG | GAG | CAG | TCC | 1008 |
| Asn | Arg | Thr | Leu | His | Val | Ser | Met | Phe | Gln | Val | Val | Gln | Glu | Gln | Ser | |
| | | 160 | | | | | 165 | | | | | 170 | | | | |
| AAC | AGG | GAG | TCT | GAC | TTG | TTC | TTT | TTG | GAT | CTT | CAG | ACG | CTC | CGA | GCT | 1056 |
| Asn | Arg | Glu | Ser | Asp | Leu | Phe | Phe | Leu | Asp | Leu | Gln | Thr | Leu | Arg | Ala | |
| | 175 | | | | | 180 | | | | | 185 | | | | | |
| GGA | GAC | GAG | GGC | TGG | CTG | GTG | CTG | GAT | GTC | ACA | GCA | GCC | AGT | GAC | TGC | 1104 |
| Gly | Asp | Glu | Gly | Trp | Leu | Val | Leu | Asp | Val | Thr | Ala | Ala | Ser | Asp | Cys | |
| 190 | | | | | 195 | | | | | 200 | | | | | 205 | |
| TGG | TTG | CTG | AAG | CGT | CAC | AAG | GAC | CTG | GGA | CTC | CGC | CTC | TAT | GTG | GAG | 1152 |
| Trp | Leu | Leu | Lys | Arg | His | Lys | Asp | Leu | Gly | Leu | Arg | Leu | Tyr | Val | Glu | |
| | | | | 210 | | | | | 215 | | | | | 220 | | |
| ACT | GAG | GAC | GGG | CAC | AGC | GTG | GAT | CCT | GGC | CTG | GCC | GGC | CTG | CTG | GGT | 1200 |
| Thr | Glu | Asp | Gly | His | Ser | Val | Asp | Pro | Gly | Leu | Ala | Gly | Leu | Leu | Gly | |
| | | | 225 | | | | | 230 | | | | | 235 | | | |
| CAA | CGG | GCC | CCA | CGC | TCC | CAA | CAG | CCT | TTC | GTG | GTC | ACT | TTC | TTC | AGG | 1248 |
| Gln | Arg | Ala | Pro | Arg | Ser | Gln | Gln | Pro | Phe | Val | Val | Thr | Phe | Phe | Arg | |
| | | 240 | | | | | 245 | | | | | 250 | | | | |
| GCC | AGT | CCG | AGT | CCC | ATC | CGC | ACC | CCT | CGG | GCA | GTG | AGG | CCA | CTG | AGG | 1296 |
| Ala | Ser | Pro | Ser | Pro | Ile | Arg | Thr | Pro | Arg | Ala | Val | Arg | Pro | Leu | Arg | |
| | 255 | | | | | 260 | | | | | 265 | | | | | |
| AGG | AGG | CAG | CCG | AAG | AAA | AGC | AAC | GAG | CTG | CCG | CAG | GCC | AAC | CGA | CTC | 1344 |
| Arg | Arg | Gln | Pro | Lys | Lys | Ser | Asn | Glu | Leu | Pro | Gln | Ala | Asn | Arg | Leu | |
| 270 | | | | | 275 | | | | | 280 | | | | | 285 | |
| CCA | GGG | ATC | TTT | GAT | GAC | GTC | CAC | GGC | TCC | CAC | GGC | CGG | CAG | GTC | TGC | 1392 |
| Pro | Gly | Ile | Phe | Asp | Asp | Val | His | Gly | Ser | His | Gly | Arg | Gln | Val | Cys | |
| | | | | 290 | | | | | 295 | | | | | 300 | | |
| CGT | CGG | CAC | GAG | CTC | TAC | GTC | AGC | TTC | CAG | GAC | CTC | GGC | TGG | CTG | GAC | 1440 |
| Arg | Arg | His | Glu | Leu | Tyr | Val | Ser | Phe | Gln | Asp | Leu | Gly | Trp | Leu | Asp | |
| | | | 305 | | | | | 310 | | | | | 315 | | | |
| TGG | GTC | ATC | GCT | CCC | CAA | GGC | TAC | TCG | GCC | TAT | TAC | TGT | GAG | GGG | GAG | 1488 |
| Trp | Val | Ile | Ala | Pro | Gln | Gly | Tyr | Ser | Ala | Tyr | Tyr | Cys | Glu | Gly | Glu | |
| | | 320 | | | | | 325 | | | | | 330 | | | | |
| TGC | TCC | TTC | CCA | CTG | GAC | TCC | TGC | ATG | AAT | GCC | ACC | AAC | CAC | GCC | ATC | 1536 |
| Cys | Ser | Phe | Pro | Leu | Asp | Ser | Cys | Met | Asn | Ala | Thr | Asn | His | Ala | Ile | |
| | 335 | | | | | 340 | | | | | 345 | | | | | |
| CTG | CAG | TCC | CTG | GTG | CAC | CTG | ATG | AAG | CCA | AAC | GCA | GTC | CCC | AAG | GCG | 1584 |
| Leu | Gln | Ser | Leu | Val | His | Leu | Met | Lys | Pro | Asn | Ala | Val | Pro | Lys | Ala | |
| 350 | | | | | 355 | | | | | 360 | | | | | 365 | |
| TGC | TGT | GCA | CCC | ACC | AAG | CTG | AGC | GCC | ACC | TCT | GTG | CTC | TAC | TAT | GAC | 1632 |
| Cys | Cys | Ala | Pro | Thr | Lys | Leu | Ser | Ala | Thr | Ser | Val | Leu | Tyr | Tyr | Asp | |
| | | | | 370 | | | | | 375 | | | | | 380 | | |
| AGC | AGC | AAC | AAC | GTC | ATC | CTG | CGC | AAA | CAC | CGC | AAC | ATG | GTG | GTC | AAG | 1680 |
| Ser | Ser | Asn | Asn | Val | Ile | Leu | Arg | Lys | His | Arg | Asn | Met | Val | Val | Lys | |
| | | | 385 | | | | | 390 | | | | | 395 | | | |
| GCC | TGC | GGC | TGC | CAC | TGAGTCAGCC | | CGCCCAGCCC | | TACTGCAG | | | | | | | 1723 |
| Ala | Cys | Gly | Cys | His | | | | | | | | | | | | |
| | | | | 400 | | | | | | | | | | | | |

( 2 ) INFORMATION FOR SEQ ID NO:21:

( i ) SEQUENCE CHARACTERISTICS:

( A ) LENGTH: 402 amino acids
( B ) TYPE: amino acid
( D ) TOPOLOGY: linear ( i i ) MOLECULE TYPE: protein ( x i ) SEQUENCE DESCRIPTION: SEQ ID NO:21:

| Met | Thr | Ala | Leu | Pro | Gly | Pro | Leu | Trp | Leu | Leu | Gly | Leu | Ala | Leu | Cys |
|---|---|---|---|---|---|---|---|---|---|---|---|---|---|---|---|
| 1 | | | | 5 | | | | | 10 | | | | | 15 | |
| Ala | Leu | Gly | Gly | Gly | Gly | Pro | Gly | Leu | Arg | Pro | Pro | Pro | Gly | Cys | Pro |
| | | | 20 | | | | | 25 | | | | | 30 | | |
| Gln | Arg | Arg | Leu | Gly | Ala | Arg | Glu | Arg | Arg | Asp | Val | Gln | Arg | Glu | Ile |
| | | 35 | | | | | 40 | | | | | 45 | | | |
| Leu | Ala | Val | Leu | Gly | Leu | Pro | Gly | Arg | Pro | Arg | Pro | Arg | Ala | Pro | Pro |
| | 50 | | | | | 55 | | | | | 60 | | | | |
| Ala | Ala | Ser | Arg | Leu | Pro | Ala | Ser | Ala | Pro | Leu | Phe | Met | Leu | Asp | Leu |
| 65 | | | | | 70 | | | | | 75 | | | | | 80 |
| Tyr | His | Ala | Met | Ala | Gly | Asp | Asp | Asp | Asp | Gly | Ala | Pro | Ala | Glu | |
| | | | | 85 | | | | | 90 | | | | | 95 | |
| Arg | Arg | Leu | Gly | Arg | Ala | Asp | Leu | Val | Met | Ser | Phe | Val | Asn | Met | Val |
| | | | 100 | | | | | 105 | | | | | 110 | | |
| Glu | Arg | Asp | Arg | Ala | Leu | Gly | His | Gln | Glu | Pro | His | Trp | Lys | Glu | Phe |
| | | 115 | | | | | 120 | | | | | 125 | | | |
| Arg | Phe | Asp | Leu | Thr | Gln | Ile | Pro | Ala | Gly | Glu | Ala | Val | Thr | Ala | Ala |
| | 130 | | | | | 135 | | | | | 140 | | | | |
| Glu | Phe | Arg | Ile | Tyr | Lys | Val | Pro | Ser | Ile | His | Leu | Leu | Asn | Arg | Thr |
| 145 | | | | | 150 | | | | | 155 | | | | | 160 |
| Leu | His | Val | Ser | Met | Phe | Gln | Val | Val | Gln | Glu | Gln | Ser | Asn | Arg | Glu |
| | | | | 165 | | | | | 170 | | | | | 175 | |
| Ser | Asp | Leu | Phe | Phe | Leu | Asp | Leu | Gln | Thr | Leu | Arg | Ala | Gly | Asp | Glu |
| | | | 180 | | | | | 185 | | | | | 190 | | |
| Gly | Trp | Leu | Val | Leu | Asp | Val | Thr | Ala | Ala | Ser | Asp | Cys | Trp | Leu | Leu |
| | | | 195 | | | | | 200 | | | | | 205 | | |
| Lys | Arg | His | Lys | Asp | Leu | Gly | Leu | Arg | Leu | Tyr | Val | Glu | Thr | Glu | Asp |
| | | 210 | | | | | 215 | | | | | 220 | | | |
| Gly | His | Ser | Val | Asp | Pro | Gly | Leu | Ala | Gly | Leu | Leu | Gly | Gln | Arg | Ala |
| 225 | | | | | 230 | | | | | 235 | | | | | 240 |
| Pro | Arg | Ser | Gln | Gln | Pro | Phe | Val | Val | Thr | Phe | Phe | Arg | Ala | Ser | Pro |
| | | | | 245 | | | | | 250 | | | | | 255 | |
| Ser | Pro | Ile | Arg | Thr | Pro | Arg | Ala | Val | Arg | Pro | Leu | Arg | Arg | Arg | Gln |
| | | | 260 | | | | | 265 | | | | | 270 | | |
| Pro | Lys | Lys | Ser | Asn | Glu | Leu | Pro | Gln | Ala | Asn | Arg | Leu | Pro | Gly | Ile |
| | | 275 | | | | | 280 | | | | | 285 | | | |
| Phe | Asp | Asp | Val | His | Gly | Ser | His | Gly | Arg | Gln | Val | Cys | Arg | Arg | His |
| | 290 | | | | | 295 | | | | | 300 | | | | |
| Glu | Leu | Tyr | Val | Ser | Phe | Gln | Asp | Leu | Gly | Trp | Leu | Asp | Trp | Val | Ile |
| 305 | | | | | 310 | | | | | 315 | | | | | 320 |
| Ala | Pro | Gln | Gly | Tyr | Ser | Ala | Tyr | Tyr | Cys | Glu | Gly | Glu | Cys | Ser | Phe |
| | | | | 325 | | | | | 330 | | | | | 335 | |
| Pro | Leu | Asp | Ser | Cys | Met | Asn | Ala | Thr | Asn | His | Ala | Ile | Leu | Gln | Ser |
| | | | 340 | | | | | 345 | | | | | 350 | | |
| Leu | Val | His | Leu | Met | Lys | Pro | Asn | Ala | Val | Pro | Lys | Ala | Cys | Cys | Ala |
| | | 355 | | | | | 360 | | | | | 365 | | | |
| Pro | Thr | Lys | Leu | Ser | Ala | Thr | Ser | Val | Leu | Tyr | Tyr | Asp | Ser | Ser | Asn |
| | 370 | | | | | 375 | | | | | 380 | | | | |

| Asn | Val | Ile | Leu | Arg | Lys | His | Arg | Asn | Met | Val | Val | Lys | Ala | Cys | Gly |
| 385 | | | | | 390 | | | | | 395 | | | | | 400 |

Cys His ( 2 ) INFORMATION FOR SEQ ID NO:22:

( i ) SEQUENCE CHARACTERISTICS:
        ( A ) LENGTH: 1926 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 93..1289
        ( D ) OTHER INFORMATION: /product= "MOP2 CDNA"

( x i ) SEQUENCE DESCRIPTION: SEQ ID NO:22:

```
GCCAGGCACA  GGTGCGCCGT  CTGGTCCTCC  CCGTCTGGCG  TCAGCCGAGC  CCGACCAGCT           60

ACCAGTGGAT  GCGCGCCGGC  TGAAAGTCCG AG ATG GCT ATG CGT CCC GGG CCA               113
                                     Met Ala Met Arg Pro Gly Pro
                                      1           5
```

| CTC | TGG | CTA | TTG | GGC | CTT | GCT | CTG | TGC | GCG | CTG | GGA | GGC | GGC | CAC | GGT | 161 |
| Leu | Trp | Leu | Leu | Gly | Leu | Ala | Leu | Cys | Ala | Leu | Gly | Gly | Gly | His | Gly | |
| | | 10 | | | | | 15 | | | | | 20 | | | | |

| CCG | CGT | CCC | CCG | CAC | ACC | TGT | CCC | CAG | CGT | CGC | CTG | GGA | GCG | CGC | GAG | 209 |
| Pro | Arg | Pro | Pro | His | Thr | Cys | Pro | Gln | Arg | Arg | Leu | Gly | Ala | Arg | Glu | |
| | 25 | | | | | 30 | | | | | 35 | | | | | |

| CGC | CGC | GAC | ATG | CAG | CGT | GAA | ATC | CTG | GCG | GTG | CTC | GGG | CTA | CCG | GGA | 257 |
| Arg | Arg | Asp | Met | Gln | Arg | Glu | Ile | Leu | Ala | Val | Leu | Gly | Leu | Pro | Gly | |
| 40 | | | | | 45 | | | | | 50 | | | | | 55 | |

| CGG | CCC | CGA | CCC | CGT | GCA | CAA | CCC | GCG | GCT | GCC | CGG | CAG | CCA | GCG | TCC | 305 |
| Arg | Pro | Arg | Pro | Arg | Ala | Gln | Pro | Ala | Ala | Ala | Arg | Gln | Pro | Ala | Ser | |
| | | | | 60 | | | | | 65 | | | | | 70 | | |

| GCG | CCC | CTC | TTC | ATG | TTG | GAC | CTA | TAC | CAC | GCC | ATG | ACC | GAT | GAC | GAC | 353 |
| Ala | Pro | Leu | Phe | Met | Leu | Asp | Leu | Tyr | His | Ala | Met | Thr | Asp | Asp | Asp | |
| | | | 75 | | | | | 80 | | | | | 85 | | | |

| GAC | GGC | GGG | CCA | CCA | CAG | GCT | CAC | TTA | GGC | CGT | GCC | GAC | CTG | GTC | ATG | 401 |
| Asp | Gly | Gly | Pro | Pro | Gln | Ala | His | Leu | Gly | Arg | Ala | Asp | Leu | Val | Met | |
| | | 90 | | | | | 95 | | | | | 100 | | | | |

| AGC | TTC | GTC | AAC | ATG | GTG | GAA | CGC | GAC | CGT | ACC | CTG | GGC | TAC | CAG | GAG | 449 |
| Ser | Phe | Val | Asn | Met | Val | Glu | Arg | Asp | Arg | Thr | Leu | Gly | Tyr | Gln | Glu | |
| | 105 | | | | | 110 | | | | | 115 | | | | | |

| CCA | CAC | TGG | AAG | GAA | TTC | CAC | TTT | GAC | CTA | ACC | CAG | ATC | CCT | GCT | GGG | 497 |
| Pro | His | Trp | Lys | Glu | Phe | His | Phe | Asp | Leu | Thr | Gln | Ile | Pro | Ala | Gly | |
| 120 | | | | | 125 | | | | | 130 | | | | | 135 | |

| GAG | GCT | GTC | ACA | GCT | GCT | GAG | TTC | CGG | ATC | TAC | AAA | GAA | CCC | AGC | ACC | 545 |
| Glu | Ala | Val | Thr | Ala | Ala | Glu | Phe | Arg | Ile | Tyr | Lys | Glu | Pro | Ser | Thr | |
| | | | | 140 | | | | | 145 | | | | | 150 | | |

| CAC | CCG | CTC | AAC | ACA | ACC | CTC | CAC | ATC | AGC | ATG | TTC | GAA | GTG | GTC | CAA | 593 |
| His | Pro | Leu | Asn | Thr | Thr | Leu | His | Ile | Ser | Met | Phe | Glu | Val | Val | Gln | |
| | | | | 155 | | | | | 160 | | | | | 165 | | |

| GAG | CAC | TCC | AAC | AGG | GAG | TCT | GAC | TTG | TTC | TTT | TTG | GAT | CTT | CAG | ACG | 641 |
| Glu | His | Ser | Asn | Arg | Glu | Ser | Asp | Leu | Phe | Phe | Leu | Asp | Leu | Gln | Thr | |
| | | 170 | | | | | 175 | | | | | 180 | | | | |

| CTC | CGA | TCT | GGG | GAC | GAG | GGC | TGG | CTG | GTG | CTG | GAC | ATC | ACA | GCA | GCC | 689 |
| Leu | Arg | Ser | Gly | Asp | Glu | Gly | Trp | Leu | Val | Leu | Asp | Ile | Thr | Ala | Ala | |
| | 185 | | | | | 190 | | | | | 195 | | | | | |

| AGT | GAC | CGA | TGG | CTG | CTG | AAC | CAT | CAC | AAG | GAC | CTG | GGA | CTC | CGC | CTC | 737 |
| Ser | Asp | Arg | Trp | Leu | Leu | Asn | His | His | Lys | Asp | Leu | Gly | Leu | Arg | Leu | |
| 200 | | | | | 205 | | | | | 210 | | | | | 215 | |

-continued

```
TAT GTG GAA ACC GCG GAT GGG CAC AGC ATG GAT CCT GGC CTG GCT GGT      785
Tyr Val Glu Thr Ala Asp Gly His Ser Met Asp Pro Gly Leu Ala Gly
            220                 225                 230

CTG CTT GGA CGA CAA GCA CCA CGC TCC AGA CAG CCT TTC ATG GTA ACC      833
Leu Leu Gly Arg Gln Ala Pro Arg Ser Arg Gln Pro Phe Met Val Thr
        235                 240                 245

TTC TTC AGG GCC AGC CAG AGT CCT GTG CGG GCC CCT CGG GCA GCG AGA      881
Phe Phe Arg Ala Ser Gln Ser Pro Val Arg Ala Pro Arg Ala Ala Arg
            250                 255                 260

CCA CTG AAG AGG AGG CAG CCA AAG AAA ACG AAC GAG CTT CCG CAC CCC      929
Pro Leu Lys Arg Arg Gln Pro Lys Lys Thr Asn Glu Leu Pro His Pro
        265                 270                 275

AAC AAA CTC CCA GGG ATC TTT GAT GAT GGC CAC GGT TCC CGC GGC AGA      977
Asn Lys Leu Pro Gly Ile Phe Asp Asp Gly His Gly Ser Arg Gly Arg
280                 285                 290                 295

GAG GTT TGC CGC AGG CAT GAG CTC TAC GTC AGC TTC CGT GAC CTT GGC     1025
Glu Val Cys Arg Arg His Glu Leu Tyr Val Ser Phe Arg Asp Leu Gly
            300                 305                 310

TGG CTG GAC TGG GTC ATC GCC CCC CAG GGC TAC TCT GCC TAT TAC TGT     1073
Trp Leu Asp Trp Val Ile Ala Pro Gln Gly Tyr Ser Ala Tyr Tyr Cys
            315                 320                 325

GAG GGG GAG TGT GCT TTC CCA CTG GAC TCC TGT ATG AAC GCC ACC AAC     1121
Glu Gly Glu Cys Ala Phe Pro Leu Asp Ser Cys Met Asn Ala Thr Asn
        330                 335                 340

CAT GCC ATC TTG CAG TCT CTG GTG CAC CTG ATG AAG CCA GAT GTT GTC     1169
His Ala Ile Leu Gln Ser Leu Val His Leu Met Lys Pro Asp Val Val
        345                 350                 355

CCC AAG GCA TGC TGT GCA CCC ACC AAA CTG AGT GCC ACC TCT GTG CTG     1217
Pro Lys Ala Cys Cys Ala Pro Thr Lys Leu Ser Ala Thr Ser Val Leu
360                 365                 370                 375

TAC TAT GAC AGC AGC AAC AAT GTC ATC CTG CGT AAA CAC CGT AAC ATG     1265
Tyr Tyr Asp Ser Ser Asn Asn Val Ile Leu Arg Lys His Arg Asn Met
            380                 385                 390

GTG GTC AAG GCC TGT GGC TGC CAC TGAGGCCCCG CCCAGCATCC TGCTTCTACT    1319
Val Val Lys Ala Cys Gly Cys His
            395

ACCTTACCAT CTGGCCGGGC CCCTCTCCAG AGGCAGAAAC CCTTCTATGT TATCATAGCT  1379
CAGACAGGGG CAATGGGAGG CCCTTCACTT CCCCTGGCCA CTTCCTGCTA AAATTCTGGT  1439
CTTTCCCAGT TCCTCTGTCC TTCATGGGGT TTCGGGGCTA TCACCCCGCC CTCTCCATCC  1499
TCCTACCCCA AGCATAGACT GAATGCACAC AGCATCCCAG AGCTATGCTA ACTGAGAGGT  1559
CTGGGGTCAG CACTGAAGGC CCACATGAGG AAGACTGATC CTTGGCCATC CTCAGCCCAC  1619
AATGGCAAAT TCTGGATGGT CTAAGAAGGC CGTGGAATTC TAAACTAGAT GATCTGGGCT  1679
CTCTGCACCA TTCATTGTGG CAGTTGGGAC ATTTTAGGT ATAACAGACA CATACACTTA   1739
GATCAATGCA TCGCTGTACT CCTTGAAATC AGAGCTAGCT TGTTAGAAAA AGAATCAGAG  1799
CCAGGTATAG CGGTGCATGT CATTAATCCC AGCGCTAAAG AGACAGAGAC AGGAGAATCT  1859
CTGTGAGTTC AAGGCCACAT AGAAAGAGCC TGTCTCGGGA GCAGGAAAAA AAAAAAAAC   1919
GGAATTC                                                            1926
```

( 2 ) INFORMATION FOR SEQ ID NO:23:

( i ) SEQUENCE CHARACTERISTICS:
        ( A ) LENGTH: 399 amino acids
        ( B ) TYPE: amino acid
        ( D ) TOPOLOGY: linear ( i i ) MOLECULE TYPE: protein ( x i ) SEQUENCE DESCRIPTION: SEQ ID NO:23:

| Met | Ala | Met | Arg | Pro | Gly | Pro | Leu | Trp | Leu | Leu | Gly | Leu | Ala | Leu | Cys |
|---|---|---|---|---|---|---|---|---|---|---|---|---|---|---|---|
| 1 | | | | 5 | | | | | 10 | | | | | 15 | |
| Ala | Leu | Gly | Gly | Gly | His | Gly | Pro | Arg | Pro | Pro | His | Thr | Cys | Pro | Gln |
| | | | 20 | | | | | 25 | | | | 30 | | | |
| Arg | Arg | Leu | Gly | Ala | Arg | Glu | Arg | Arg | Asp | Met | Gln | Arg | Glu | Ile | Leu |
| | | 35 | | | | 40 | | | | | 45 | | | | |
| Ala | Val | Leu | Gly | Leu | Pro | Gly | Arg | Pro | Arg | Pro | Arg | Ala | Gln | Pro | Ala |
| | 50 | | | | | 55 | | | | 60 | | | | | |
| Ala | Ala | Arg | Gln | Pro | Ala | Ser | Ala | Pro | Leu | Phe | Met | Leu | Asp | Leu | Tyr |
| 65 | | | | | 70 | | | | 75 | | | | | 80 | |
| His | Ala | Met | Thr | Asp | Asp | Asp | Gly | Gly | Pro | Pro | Gln | Ala | His | Leu | |
| | | | | 85 | | | | 90 | | | | | 95 | | |
| Gly | Arg | Ala | Asp | Leu | Val | Met | Ser | Phe | Val | Asn | Met | Val | Glu | Arg | Asp |
| | | | 100 | | | | 105 | | | | 110 | | | | |
| Arg | Thr | Leu | Gly | Tyr | Gln | Glu | Pro | His | Trp | Lys | Glu | Phe | His | Phe | Asp |
| | | 115 | | | | 120 | | | | 125 | | | | | |
| Leu | Thr | Gln | Ile | Pro | Ala | Gly | Glu | Ala | Val | Thr | Ala | Ala | Glu | Phe | Arg |
| | 130 | | | | 135 | | | | | 140 | | | | | |
| Ile | Tyr | Lys | Glu | Pro | Ser | Thr | His | Pro | Leu | Asn | Thr | Thr | Leu | His | Ile |
| 145 | | | | 150 | | | | | 155 | | | | | 160 | |
| Ser | Met | Phe | Glu | Val | Val | Gln | Glu | His | Ser | Asn | Arg | Glu | Ser | Asp | Leu |
| | | | | 165 | | | | | 170 | | | | | 175 | |
| Phe | Phe | Leu | Asp | Leu | Gln | Thr | Leu | Arg | Ser | Gly | Asp | Glu | Gly | Trp | Leu |
| | | | 180 | | | | | 185 | | | | | 190 | | |
| Val | Leu | Asp | Ile | Thr | Ala | Ala | Ser | Asp | Arg | Trp | Leu | Leu | Asn | His | His |
| | | 195 | | | | | 200 | | | | | 205 | | | |
| Lys | Asp | Leu | Gly | Leu | Arg | Leu | Tyr | Val | Glu | Thr | Ala | Asp | Gly | His | Ser |
| | 210 | | | | | 215 | | | | | 220 | | | | |
| Met | Asp | Pro | Gly | Leu | Ala | Gly | Leu | Leu | Gly | Arg | Gln | Ala | Pro | Arg | Ser |
| 225 | | | | | 230 | | | | | 235 | | | | | 240 |
| Arg | Gln | Pro | Phe | Met | Val | Thr | Phe | Phe | Arg | Ala | Ser | Gln | Ser | Pro | Val |
| | | | | 245 | | | | | 250 | | | | | 255 | |
| Arg | Ala | Pro | Arg | Ala | Ala | Arg | Pro | Leu | Lys | Arg | Arg | Gln | Pro | Lys | Lys |
| | | | 260 | | | | | 265 | | | | | 270 | | |
| Thr | Asn | Glu | Leu | Pro | His | Pro | Asn | Lys | Leu | Pro | Gly | Ile | Phe | Asp | Asp |
| | | 275 | | | | | 280 | | | | | 285 | | | |
| Gly | His | Gly | Ser | Arg | Gly | Arg | Glu | Val | Cys | Arg | Arg | His | Glu | Leu | Tyr |
| | 290 | | | | | 295 | | | | | 300 | | | | |
| Val | Ser | Phe | Arg | Asp | Leu | Gly | Trp | Leu | Asp | Trp | Val | Ile | Ala | Pro | Gln |
| 305 | | | | | 310 | | | | | 315 | | | | | 320 |
| Gly | Tyr | Ser | Ala | Tyr | Tyr | Cys | Glu | Gly | Glu | Cys | Ala | Phe | Pro | Leu | Asp |
| | | | | 325 | | | | | 330 | | | | | 335 | |
| Ser | Cys | Met | Asn | Ala | Thr | Asn | His | Ala | Ile | Leu | Gln | Ser | Leu | Val | His |
| | | | 340 | | | | | 345 | | | | | 350 | | |
| Leu | Met | Lys | Pro | Asp | Val | Val | Pro | Lys | Ala | Cys | Cys | Ala | Pro | Thr | Lys |
| | | | 355 | | | | 360 | | | | | 365 | | | |
| Leu | Ser | Ala | Thr | Ser | Val | Leu | Tyr | Tyr | Asp | Ser | Ser | Asn | Asn | Val | Ile |
| | | | 370 | | | | 375 | | | | 380 | | | | |
| Leu | Arg | Lys | His | Arg | Asn | Met | Val | Val | Lys | Ala | Cys | Gly | Cys | His | |
| 385 | | | | | 390 | | | | | 395 | | | | | |

( 2 ) INFORMATION FOR SEQ ID NO:24:

(i) SEQUENCE CHARACTERISTICS:
  (A) LENGTH: 1368 base pairs
  (B) TYPE: nucleic acid
  (C) STRANDEDNESS: single
  (D) TOPOLOGY: linear (ii) MOLECULE TYPE: cDNA (ix) FEATURE:
  (A) NAME/KEY: CDS
  (B) LOCATION: 1..1365

(xi) SEQUENCE DESCRIPTION: SEQ ID NO:24:

| ATG | TCG | GGA | CTG | CGA | AAC | ACC | TCG | GAG | GCC | GTT | GCA | GTG | CTC | GCC | TCC | 48 |
| Met | Ser | Gly | Leu | Arg | Asn | Thr | Ser | Glu | Ala | Val | Ala | Val | Leu | Ala | Ser | |
| 1 | | | | 5 | | | | | 10 | | | | | 15 | | |

| CTG | GGA | CTC | GGA | ATG | GTT | CTG | CTC | ATG | TTC | GTG | GCG | ACC | ACG | CCG | CCG | 96 |
| Leu | Gly | Leu | Gly | Met | Val | Leu | Leu | Met | Phe | Val | Ala | Thr | Thr | Pro | Pro | |
| | | | 20 | | | | | 25 | | | | | 30 | | | |

| GCC | GTT | GAG | GCC | ACC | CAG | TCG | GGG | ATT | TAC | ATA | GAC | AAC | GGC | AAG | GAC | 144 |
| Ala | Val | Glu | Ala | Thr | Gln | Ser | Gly | Ile | Tyr | Ile | Asp | Asn | Gly | Lys | Asp | |
| | | 35 | | | | | 40 | | | | | 45 | | | | |

| CAG | ACG | ATC | ATG | CAC | AGA | GTG | CTG | AGC | GAG | GAC | GAC | AAG | CTG | GAC | GTC | 192 |
| Gln | Thr | Ile | Met | His | Arg | Val | Leu | Ser | Glu | Asp | Asp | Lys | Leu | Asp | Val | |
| | 50 | | | | | 55 | | | | | 60 | | | | | |

| TCG | TAC | GAG | ATC | CTC | GAG | TTC | CTG | GGC | ATC | GCC | GAA | CGG | CCG | ACG | CAC | 240 |
| Ser | Tyr | Glu | Ile | Leu | Glu | Phe | Leu | Gly | Ile | Ala | Glu | Arg | Pro | Thr | His | |
| 65 | | | | | 70 | | | | | 75 | | | | | 80 | |

| CTG | AGC | AGC | CAC | CAG | TTG | TCG | CTG | AGG | AAG | TCG | GCT | CCC | AAG | TTC | CTG | 288 |
| Leu | Ser | Ser | His | Gln | Leu | Ser | Leu | Arg | Lys | Ser | Ala | Pro | Lys | Phe | Leu | |
| | | | | 85 | | | | | 90 | | | | | 95 | | |

| CTG | GAC | GTC | TAC | CAC | CGC | ATC | ACG | GCG | GAG | GAG | GGT | CTC | AGC | GAT | CAG | 336 |
| Leu | Asp | Val | Tyr | His | Arg | Ile | Thr | Ala | Glu | Glu | Gly | Leu | Ser | Asp | Gln | |
| | | | 100 | | | | | 105 | | | | | 110 | | | |

| GAT | GAG | GAC | GAC | GAC | TAC | GAA | CGC | GGC | CAT | CGG | TCC | AGG | AGG | AGC | GCC | 384 |
| Asp | Glu | Asp | Asp | Asp | Tyr | Glu | Arg | Gly | His | Arg | Ser | Arg | Arg | Ser | Ala | |
| | | 115 | | | | | 120 | | | | | 125 | | | | |

| GAC | CTC | GAG | GAG | GAT | GAG | GGC | GAG | CAG | CAG | AAG | AAC | TTC | ATC | ACC | GAC | 432 |
| Asp | Leu | Glu | Glu | Asp | Glu | Gly | Glu | Gln | Gln | Lys | Asn | Phe | Ile | Thr | Asp | |
| | 130 | | | | | 135 | | | | | 140 | | | | | |

| CTG | GAC | AAG | CGG | GCC | ATC | GAC | GAG | AGC | GAC | ATC | ATC | ATG | ACC | TTC | CTG | 480 |
| Leu | Asp | Lys | Arg | Ala | Ile | Asp | Glu | Ser | Asp | Ile | Ile | Met | Thr | Phe | Leu | |
| 145 | | | | | 150 | | | | | 155 | | | | | 160 | |

| AAC | AAG | CGC | CAC | CAC | AAT | GTG | GAC | GAA | CTG | CGT | CAC | GAG | CAC | GGC | CGT | 528 |
| Asn | Lys | Arg | His | His | Asn | Val | Asp | Glu | Leu | Arg | His | Glu | His | Gly | Arg | |
| | | | | 165 | | | | | 170 | | | | | 175 | | |

| CGC | CTG | TGG | TTC | GAC | GTC | TCC | AAC | GTG | CCC | AAC | GAC | AAC | TAC | CTG | GTG | 576 |
| Arg | Leu | Trp | Phe | Asp | Val | Ser | Asn | Val | Pro | Asn | Asp | Asn | Tyr | Leu | Val | |
| | | | 180 | | | | | 185 | | | | | 190 | | | |

| ATG | GCC | GAG | CTG | CGC | ATC | TAT | CAG | AAC | GCC | AAC | GAG | GGC | AAG | TGG | CTG | 624 |
| Met | Ala | Glu | Leu | Arg | Ile | Tyr | Gln | Asn | Ala | Asn | Glu | Gly | Lys | Trp | Leu | |
| | | 195 | | | | | 200 | | | | | 205 | | | | |

| ACC | GCC | AAC | AGG | GAG | TTC | ACC | ATC | ACG | GTA | TAC | GCC | ATT | GGC | ACC | GGC | 672 |
| Thr | Ala | Asn | Arg | Glu | Phe | Thr | Ile | Thr | Val | Tyr | Ala | Ile | Gly | Thr | Gly | |
| | 210 | | | | | 215 | | | | | 220 | | | | | |

| ACG | CTG | GGC | CAG | CAC | ACC | ATG | GAG | CCG | CTG | TCC | TCG | GTG | AAC | ACC | ACC | 720 |
| Thr | Leu | Gly | Gln | His | Thr | Met | Glu | Pro | Leu | Ser | Ser | Val | Asn | Thr | Thr | |
| 225 | | | | | 230 | | | | | 235 | | | | | 240 | |

| GGG | GAC | TAC | GTG | GGC | TGG | TTG | GAG | CTC | AAC | GTG | ACC | GAG | GGC | CTG | CAC | 768 |
| Gly | Asp | Tyr | Val | Gly | Trp | Leu | Glu | Leu | Asn | Val | Thr | Glu | Gly | Leu | His | |
| | | | | 245 | | | | | 250 | | | | | 255 | | |

| GAG | TGG | CTG | GTC | AAG | TCG | AAG | GAC | AAT | CAT | GGC | ATC | TAC | ATT | GGA | GCA | 816 |

| | | | | | | | | | | | | | | | | |
|---|---|---|---|---|---|---|---|---|---|---|---|---|---|---|---|---|
| Glu | Trp | Leu | Val<br>260 | Lys | Ser | Lys | Asp | Asn<br>265 | His | Gly | Ile | Tyr | Ile<br>270 | Gly | Ala | |
| CAC<br>His | GCT<br>Ala | GTC<br>Val<br>275 | AAC<br>Asn | CGA<br>Arg | CCC<br>Pro | GAC<br>Asp | CGC<br>Arg<br>280 | GAG<br>Glu | GTG<br>Val | AAG<br>Lys | CTG<br>Leu | GAC<br>Asp<br>285 | GAC<br>Asp | ATT<br>Ile | GGA<br>Gly | 864 |
| CTG<br>Leu | ATC<br>Ile<br>290 | CAC<br>His | CGC<br>Arg | AAG<br>Lys | GTG<br>Val | GAC<br>Asp<br>295 | GAC<br>Asp | GAG<br>Glu | TTC<br>Phe | CAG<br>Gln | CCC<br>Pro<br>300 | TTC<br>Phe | ATG<br>Met | ATC<br>Ile | GGC<br>Gly | 912 |
| TTC<br>Phe<br>305 | TTC<br>Phe | CGC<br>Arg | GGA<br>Gly | CCG<br>Pro | GAG<br>Glu<br>310 | CTG<br>Leu | ATC<br>Ile | AAG<br>Lys | GCG<br>Ala | ACG<br>Thr<br>315 | GCC<br>Ala | CAC<br>His | AGC<br>Ser | AGC<br>Ser | CAC<br>His<br>320 | 960 |
| CAC<br>His | AGG<br>Arg | AGC<br>Ser | AAG<br>Lys | CGA<br>Arg<br>325 | AGC<br>Ser | GCC<br>Ala | AGC<br>Ser | CAT<br>His | CCA<br>Pro<br>330 | CGC<br>Arg | AAG<br>Lys | CGC<br>Arg | AAG<br>Lys | AAG<br>Lys<br>335 | TCG<br>Ser | 1008 |
| GTG<br>Val | TCG<br>Ser | CCC<br>Pro | AAC<br>Asn<br>340 | AAC<br>Asn | GTG<br>Val | CCG<br>Pro | CTG<br>Leu | CTG<br>Leu<br>345 | GAA<br>Glu | CCG<br>Pro | ATG<br>Met | GAG<br>Glu | AGC<br>Ser<br>350 | ACG<br>Thr | CGC<br>Arg | 1056 |
| AGC<br>Ser | TGC<br>Cys | CAG<br>Gln | ATG<br>Met<br>355 | CAG<br>Gln | ACC<br>Thr | CTG<br>Leu | TAC<br>Tyr | ATA<br>Ile<br>360 | GAC<br>Asp | TTC<br>Phe | AAG<br>Lys | GAT<br>Asp | CTG<br>Leu<br>365 | GGC<br>Gly | TGG<br>Trp | 1104 |
| CAT<br>His | GAC<br>Asp<br>370 | TGG<br>Trp | ATC<br>Ile | ATC<br>Ile | GCA<br>Ala | CCA<br>Pro<br>375 | GAG<br>Glu | GGC<br>Gly | TAT<br>Tyr | GGC<br>Gly | GCC<br>Ala<br>380 | TTC<br>Phe | TAC<br>Tyr | TGC<br>Cys | AGC<br>Ser | 1152 |
| GGC<br>Gly<br>385 | GAG<br>Glu | TGC<br>Cys | AAT<br>Asn | TTC<br>Phe | CCG<br>Pro<br>390 | CTC<br>Leu | AAT<br>Asn | GCG<br>Ala | CAC<br>His | ATG<br>Met<br>395 | AAC<br>Asn | GCC<br>Ala | ACG<br>Thr | AAC<br>Asn | CAT<br>His<br>400 | 1200 |
| GCG<br>Ala | ATC<br>Ile | GTC<br>Val | CAG<br>Gln | ACC<br>Thr<br>405 | CTG<br>Leu | GTC<br>Val | CAC<br>His | CTG<br>Leu | CTG<br>Leu<br>410 | GAG<br>Glu | CCC<br>Pro | AAG<br>Lys | AAG<br>Lys | GTG<br>Val<br>415 | CCC<br>Pro | 1248 |
| AAG<br>Lys | CCC<br>Pro | TGC<br>Cys | TGC<br>Cys<br>420 | GCT<br>Ala | CCG<br>Pro | ACC<br>Thr | AGG<br>Arg | CTG<br>Leu<br>425 | GGA<br>Gly | GCA<br>Ala | CTA<br>Leu | CCC<br>Pro | GTT<br>Val<br>430 | CTG<br>Leu | TAC<br>Tyr | 1296 |
| CAC<br>His | CTG<br>Leu | AAC<br>Asn | GAC<br>Asp<br>435 | GAG<br>Glu | AAT<br>Asn | GTG<br>Val | AAC<br>Asn | CTG<br>Leu<br>440 | AAA<br>Lys | AAG<br>Lys | TAT<br>Tyr | AGA<br>Arg | AAC<br>Asn<br>445 | ATG<br>Met | ATT<br>Ile | 1344 |
| GTG<br>Val | AAA<br>Lys<br>450 | TCC<br>Ser | TGC<br>Cys | GGG<br>Gly | TGC<br>Cys | CAT<br>His<br>455 | TGA | | | | | | | | | 1368 |

( 2 ) INFORMATION FOR SEQ ID NO:25:

( i ) SEQUENCE CHARACTERISTICS:
        ( A ) LENGTH: 455 amino acids
        ( B ) TYPE: amino acid
        ( D ) TOPOLOGY: linear ( i i ) MOLECULE TYPE: protein ( x i ) SEQUENCE DESCRIPTION: SEQ ID NO:25:

| | | | | | | | | | | | | | | | |
|---|---|---|---|---|---|---|---|---|---|---|---|---|---|---|---|
| Met<br>1 | Ser | Gly | Leu | Arg<br>5 | Asn | Thr | Ser | Glu | Val<br>10 | Ala | Val | Leu | Ala | Ser<br>15 | |
| Leu | Gly | Leu | Gly<br>20 | Met | Val | Leu | Leu | Met<br>25 | Phe | Val | Ala | Thr | Pro<br>30 | Pro | |
| Ala | Val | Glu<br>35 | Ala | Thr | Gln | Ser | Gly<br>40 | Ile | Tyr | Ile | Asp | Asn<br>45 | Gly | Lys | Asp |
| Gln | Thr<br>50 | Ile | Met | His | Arg | Val<br>55 | Leu | Ser | Glu | Asp | Asp<br>60 | Lys | Leu | Asp | Val |
| Ser<br>65 | Tyr | Glu | Ile | Leu | Glu<br>70 | Phe | Leu | Gly | Ile | Ala<br>75 | Glu | Arg | Pro | Thr | His<br>80 |
| Leu | Ser | Ser | His | Gln<br>85 | Leu | Ser | Leu | Arg | Lys<br>90 | Ser | Ala | Pro | Lys | Phe<br>95 | Leu |

| | | | | | | | | | | | | | |
|---|---|---|---|---|---|---|---|---|---|---|---|---|---|
|Leu|Asp|Val|Tyr<br>100|His|Arg|Ile|Thr|Ala<br>105|Glu|Glu|Gly|Leu|Ser|Asp|Gln<br>110|
|Asp|Glu|Asp<br>115|Asp|Asp|Tyr|Glu|Arg<br>120|Gly|His|Arg|Ser<br>125|Arg|Ser|Ala|
|Asp|Leu<br>130|Glu|Glu|Asp|Glu|Gly<br>135|Glu|Gln|Gln|Lys|Asn<br>140|Phe|Ile|Thr|Asp|
|Leu<br>145|Asp|Lys|Arg|Ala|Ile<br>150|Asp|Glu|Ser|Asp|Ile<br>155|Ile|Met|Thr|Phe|Leu<br>160|
|Asn|Lys|Arg|His|His<br>165|Asn|Val|Asp|Glu|Leu<br>170|Arg|His|Glu|His<br>175|Gly|Arg|
|Arg|Leu|Trp|Phe<br>180|Asp|Val|Ser|Asn|Val<br>185|Pro|Asn|Asp|Asn|Tyr<br>190|Leu|Val|
|Met|Ala|Glu<br>195|Leu|Arg|Ile|Tyr|Gln<br>200|Asn|Ala|Asn|Glu|Gly<br>205|Lys|Trp|Leu|
|Thr|Ala<br>210|Asn|Arg|Glu|Phe|Thr<br>215|Ile|Thr|Val|Tyr|Ala<br>220|Ile|Gly|Thr|Gly|
|Thr<br>225|Leu|Gly|Gln|His|Thr<br>230|Met|Glu|Pro|Leu|Ser<br>235|Ser|Val|Asn|Thr|Thr<br>240|
|Gly|Asp|Tyr|Val|Gly<br>245|Trp|Leu|Glu|Leu|Asn<br>250|Val|Thr|Glu|Gly|Leu<br>255|His|
|Glu|Trp|Leu|Val<br>260|Lys|Ser|Lys|Asp|Asn<br>265|His|Gly|Ile|Tyr|Ile<br>270|Gly|Ala|
|His|Ala|Val<br>275|Asn|Arg|Pro|Asp|Arg<br>280|Glu|Val|Lys|Leu|Asp<br>285|Asp|Ile|Gly|
|Leu|Ile<br>290|His|Arg|Lys|Val|Asp<br>295|Asp|Glu|Phe|Gln|Pro<br>300|Phe|Met|Ile|Gly|
|Phe<br>305|Phe|Arg|Gly|Pro|Glu<br>310|Leu|Ile|Lys|Ala|Thr<br>315|Ala|His|Ser|Ser|His<br>320|
|His|Arg|Ser|Lys|Arg<br>325|Ser|Ala|Ser|His|Pro<br>330|Arg|Lys|Arg|Lys<br>335|Lys|Ser|
|Val|Ser|Pro|Asn<br>340|Asn|Val|Pro|Leu|Leu<br>345|Glu|Pro|Met|Glu|Ser<br>350|Thr|Arg|
|Ser|Cys|Gln<br>355|Met|Gln|Thr|Leu|Tyr<br>360|Ile|Asp|Phe|Lys|Asp<br>365|Leu|Gly|Trp|
|His|Asp<br>370|Trp|Ile|Ile|Ala|Pro<br>375|Glu|Gly|Tyr|Gly|Ala<br>380|Phe|Tyr|Cys|Ser|
|Gly<br>385|Glu|Cys|Asn|Phe|Pro<br>390|Leu|Asn|Ala|His|Met<br>395|Asn|Ala|Thr|Asn|His<br>400|
|Ala|Ile|Val|Gln|Thr<br>405|Leu|Val|His|Leu|Leu<br>410|Glu|Pro|Lys|Lys|Val<br>415|Pro|
|Lys|Pro|Cys|Cys<br>420|Ala|Pro|Thr|Arg|Leu<br>425|Gly|Ala|Leu|Pro|Val<br>430|Leu|Tyr|
|His|Leu|Asn<br>435|Asp|Glu|Asn|Val|Asn<br>440|Leu|Lys|Lys|Tyr|Arg<br>445|Asn|Met|Ile|
|Val|Lys<br>450|Ser|Cys|Gly|Cys|His<br>455|

( 2 ) INFORMATION FOR SEQ ID NO:26:

( i ) SEQUENCE CHARACTERISTICS:
        ( A ) LENGTH: 104 amino acids
        ( B ) TYPE: amino acid
        ( C ) STRANDEDNESS: single
        ( D ) TOPOLOGY: linear ( i i ) MOLECULE TYPE: protein ( i x ) FEATURE:
   ( A ) NAME/KEY: Protein
   ( B ) LOCATION: 1..104
   ( D ) OTHER INFORMATION: /label= BMP3

( x i ) SEQUENCE DESCRIPTION: SEQ ID NO:26:

| Cys | Ala | Arg | Arg | Tyr | Leu | Lys | Val | Asp | Phe | Ala | Asp | Ile | Gly | Trp | Ser |
|---|---|---|---|---|---|---|---|---|---|---|---|---|---|---|---|
| 1 | | | | 5 | | | | | 10 | | | | | 15 | |
| Glu | Trp | Ile | Ile | Ser | Pro | Lys | Ser | Phe | Asp | Ala | Tyr | Tyr | Cys | Ser | Gly |
| | | | 20 | | | | 25 | | | | | 30 | | | |
| Ala | Cys | Gln | Phe | Pro | Met | Pro | Lys | Ser | Leu | Lys | Pro | Ser | Asn | His | Ala |
| | | 35 | | | | | 40 | | | | | 45 | | | |
| Thr | Ile | Gln | Ser | Ile | Val | Ala | Arg | Ala | Val | Gly | Val | Val | Pro | Gly | Ile |
| | 50 | | | | | 55 | | | | | 60 | | | | |
| Pro | Glu | Pro | Cys | Cys | Val | Pro | Glu | Lys | Met | Ser | Ser | Leu | Ser | Ile | Leu |
| 65 | | | | | 70 | | | | 75 | | | | | | 80 |
| Phe | Phe | Asp | Glu | Asn | Lys | Asn | Val | Val | Leu | Lys | Val | Tyr | Pro | Asn | Met |
| | | | | 85 | | | | | 90 | | | | | 95 | |
| Thr | Val | Glu | Ser | Cys | Ala | Cys | Arg |
| | | | 100 | | | | |

( 2 ) INFORMATION FOR SEQ ID NO:27:

( i ) SEQUENCE CHARACTERISTICS:
      ( A ) LENGTH: 102 amino acids
      ( B ) TYPE: amino acid
      ( C ) STRANDEDNESS: single
      ( D ) TOPOLOGY: linear ( i i ) MOLECULE TYPE: protein ( i x ) FEATURE:
      ( A ) NAME/KEY: Protein
      ( B ) LOCATION: 1..102
      ( D ) OTHER INFORMATION: /label= BMP5

( x i ) SEQUENCE DESCRIPTION: SEQ ID NO:27:

| Cys | Lys | Lys | His | Glu | Leu | Tyr | Val | Ser | Phe | Arg | Asp | Leu | Gly | Trp | Gln |
|---|---|---|---|---|---|---|---|---|---|---|---|---|---|---|---|
| 1 | | | | 5 | | | | | 10 | | | | | 15 | |
| Asp | Trp | Ile | Ile | Ala | Pro | Glu | Gly | Tyr | Ala | Ala | Phe | Tyr | Cys | Asp | Gly |
| | | | 20 | | | | 25 | | | | | 30 | | | |
| Glu | Cys | Ser | Phe | Pro | Leu | Asn | Ala | His | Met | Asn | Ala | Thr | Asn | His | Ala |
| | | 35 | | | | | 40 | | | | | 45 | | | |
| Ile | Val | Gln | Thr | Leu | Val | His | Leu | Met | Phe | Pro | Asp | His | Val | Pro | Lys |
| | 50 | | | | | 55 | | | | | 60 | | | | |
| Pro | Cys | Cys | Ala | Pro | Thr | Lys | Leu | Asn | Ala | Ile | Ser | Val | Leu | Tyr | Phe |
| 65 | | | | | 70 | | | | 75 | | | | | | 80 |
| Asp | Asp | Ser | Ser | Asn | Val | Ile | Leu | Lys | Lys | Tyr | Arg | Asn | Met | Val | Val |
| | | | | 85 | | | | | 90 | | | | | 95 | |
| Arg | Ser | Cys | Gly | Cys | His |
| | | | 100 | | |

( 2 ) INFORMATION FOR SEQ ID NO:28:

( i ) SEQUENCE CHARACTERISTICS:
      ( A ) LENGTH: 102 amino acids
      ( B ) TYPE: amino acid
      ( C ) STRANDEDNESS: single
      ( D ) TOPOLOGY: linear ( i i ) MOLECULE TYPE: protein ( i x ) FEATURE:

(A) NAME/KEY: Protein
(B) LOCATION: 1..102
(D) OTHER INFORMATION: /label= BMP6

(xi) SEQUENCE DESCRIPTION: SEQ ID NO:28:

| Cys | Arg | Lys | His | Glu | Leu | Tyr | Val | Ser | Phe | Gln | Asp | Leu | Gly | Trp | Gln |
|---|---|---|---|---|---|---|---|---|---|---|---|---|---|---|---|
| 1 | | | | 5 | | | | | 10 | | | | | 15 | |
| Asp | Trp | Ile | Ile | Ala | Pro | Lys | Gly | Tyr | Ala | Ala | Asn | Tyr | Cys | Asp | Gly |
| | | | 20 | | | | | 25 | | | | | 30 | | |
| Glu | Cys | Ser | Phe | Pro | Leu | Asn | Ala | His | Met | Asn | Ala | Thr | Asn | His | Ala |
| | | 35 | | | | | 40 | | | | | 45 | | | |
| Ile | Val | Gln | Thr | Leu | Val | His | Leu | Met | Asn | Pro | Glu | Tyr | Val | Pro | Lys |
| | 50 | | | | | 55 | | | | | 60 | | | | |
| Pro | Cys | Cys | Ala | Pro | Thr | Lys | Leu | Asn | Ala | Ile | Ser | Val | Leu | Tyr | Phe |
| 65 | | | | | 70 | | | | | 75 | | | | | 80 |
| Asp | Asp | Asn | Ser | Asn | Val | Ile | Leu | Lys | Lys | Tyr | Arg | Trp | Met | Val | Val |
| | | | | 85 | | | | | 90 | | | | | 95 | |
| Arg | Ala | Cys | Gly | Cys | His | | | | | | | | | | |
| | | | 100 | | | | | | | | | | | | |

(2) INFORMATION FOR SEQ ID NO:29:

(i) SEQUENCE CHARACTERISTICS:
(A) LENGTH: 102 amino acids
(B) TYPE: amino acid
(C) STRANDEDNESS: single
(D) TOPOLOGY: linear (ii) MOLECULE TYPE: protein (ix) FEATURE:
(A) NAME/KEY: Protein
(B) LOCATION: 1..102
(D) OTHER INFORMATION: /label= OPX
/ note= "WHEREIN XAA AT EACH POS'N IS INDEPENDENTLY
SELECTED FROM THE RESIDUES OCCURING AT THE CORRESPONDING
POS'N IN THE C-TERMINAL SEQUENCE OF MOUSE OR HUMAN OP1 OR OP2 (SEQ. ID NOS. 5,6,7&8 OR 16,18, 20&22"

( x i ) SEQUENCE DESCRIPTION: SEQ ID NO:29:

Cys Xaa Xaa His Glu Leu Tyr Val Xaa Phe Xaa Asp Leu Gly Trp Xaa
1 5 10 15

Asp Trp Xaa Ile Ala Pro Xaa Gly Tyr Xaa Ala Tyr Tyr Cys Glu Gly
20 25 30

Glu Cys Xaa Phe Pro Leu Xaa Ser Xaa Met Asn Ala Thr Asn His Ala
35 40 45

Ile Xaa Gln Xaa Leu Val His Xaa Xaa Xaa Pro Xaa Xaa Val Pro Lys
50 55 60

Xaa Cys Cys Ala Pro Thr Xaa Leu Xaa Ala Xaa Ser Val Leu Tyr Xaa
65 70 75 80

Asp Xaa Ser Xaa Asn Val Xaa Leu Xaa Lys Xaa Arg Asn Met Val Val
85 90 95

Xaa Ala Cys Gly Cys His
100

( 2 ) INFORMATION FOR SEQ ID NO:30:

( i ) SEQUENCE CHARACTERISTICS:
( A ) LENGTH: 97 amino acids
( B ) TYPE: amino acid
( C ) STRANDEDNESS: single
( D ) TOPOLOGY: linear ( i i ) MOLECULE TYPE: protein ( i x ) FEATURE:
    ( A ) NAME/KEY: Protein
    ( B ) LOCATION: 1..97
    ( D ) OTHER INFORMATION: /label= GENERIC-SEQ-5
        / note= "WHEREIN EACH XAA IS INDEPENDENTLY SELECTED FROM
        A GROUP OF ONE OR MORE SPECIFIED AMINO ACIDS AS DEFINED
        IN THE SPECIFICATION"

( x i ) SEQUENCE DESCRIPTION: SEQ ID NO:30:

```
Leu Xaa Xaa Xaa Phe Xaa Xaa Xaa Gly Trp Xaa Xaa Trp Xaa Xaa Xaa
1                5                   10                  15

Pro Xaa Xaa Xaa Xaa Ala Xaa Tyr Cys Xaa Gly Xaa Cys Xaa Xaa Pro
        20                  25                  30

Xaa Xaa Xaa Xaa Xaa Xaa Xaa Xaa Asn His Ala Xaa Xaa Xaa Xaa Xaa
        35                  40                  45

Xaa Xaa Xaa Xaa Xaa Xaa Xaa Xaa Xaa Xaa Xaa Cys Cys Xaa Pro
    50                  55                  60

Xaa Xaa Xaa Xaa Xaa Xaa Xaa Xaa Leu Xaa Xaa Xaa Xaa Xaa Xaa Xaa
65                  70                  75                  80

Val Xaa Leu Xaa Xaa Xaa Xaa Xaa Met Xaa Val Xaa Xaa Cys Xaa Cys
            85                  90                  95

Xaa
```

( 2 ) INFORMATION FOR SEQ ID NO:31:

( i ) SEQUENCE CHARACTERISTICS:
        ( A ) LENGTH: 102 amino acids
        ( B ) TYPE: amino acid
        ( C ) STRANDEDNESS: single
        ( D ) TOPOLOGY: linear ( i i ) MOLECULE TYPE: protein ( i x ) FEATURE:
    ( A ) NAME/KEY: Protein
    ( B ) LOCATION: 1..102
    ( D ) OTHER INFORMATION: /label= GENERIC-SEQ-6
        / note= "WHEREIN EACH XAA IS INDEPENDENTLY SELECTED FROM
        A GROUP OF ONE OR MORE SPECIFIED AMINO ACIDS AS DEFINED
        IN THE SPECIFICATION"

( x i ) SEQUENCE DESCRIPTION: SEQ ID NO:31:

```
Cys Xaa Xaa Xaa Xaa Leu Xaa Xaa Xaa Phe Xaa Xaa Xaa Gly Trp Xaa
1                5                   10                  15

Xaa Trp Xaa Xaa Xaa Pro Xaa Xaa Xaa Xaa Ala Xaa Tyr Cys Xaa Gly
            20                  25                  30

Xaa Cys Xaa Xaa Pro Xaa Xaa Xaa Xaa Xaa Xaa Xaa Xaa Asn His Ala
        35                  40                  45

Xaa Xaa Xaa Xaa Xaa Xaa Xaa Xaa Xaa Xaa Xaa Xaa Xaa Xaa Xaa Xaa
    50                  55                  60

Xaa Cys Cys Xaa Pro Xaa Xaa Xaa Xaa Xaa Xaa Xaa Leu Xaa Xaa
65                  70                  75                  80

Xaa Xaa Xaa Xaa Xaa Val Xaa Leu Xaa Xaa Xaa Xaa Xaa Met Xaa Val
                85                  90                  95

Xaa Xaa Cys Xaa Cys Xaa
            100
```

( 2 ) INFORMATION FOR SEQ ID NO:32:

( i ) SEQUENCE CHARACTERISTICS:
        ( A ) LENGTH: 1247 base pairs
        ( B ) TYPE: nucleic acid
        ( C ) STRANDEDNESS: single ( D ) TOPOLOGY: linear ( i i ) MOLECULE TYPE: cDNA ( i x ) FEATURE:
    ( A ) NAME/KEY: CDS
    ( B ) LOCATION: 84..1199
    ( D ) OTHER INFORMATION: /product= "GDF-1"

( x i ) SEQUENCE DESCRIPTION: SEQ ID NO:32:

```
GGGGACACCG  GCCCCGCCCT  CAGCCCACTG  GTCCCGGGCC  GCCGCGGACC  CTGCGCACTC         60

TCTGGTCATC  GCCTGGGAGG  AAG ATG CCA CCG CCG CAG CAA GGT CCC TGC               110
                            Met Pro Pro Pro Gln Gln Gly Pro Cys
                             1                5

GGC CAC CAC CTC CTC CTC CTC CTG GCC CTG CTG CTG CCC TCG CTG CCC               158
Gly His His Leu Leu Leu Leu Leu Ala Leu Leu Leu Pro Ser Leu Pro
 10              15                  20                  25

CTG ACC CGC GCC CCC GTG CCC CCA GGC CCA GCC GCC GCC CTG CTC CAG               206
Leu Thr Arg Ala Pro Val Pro Pro Gly Pro Ala Ala Ala Leu Leu Gln
                 30              35                      40

GCT CTA GGA CTG CGC GAT GAG CCC CAG GGT GCC CCC AGG CTC CGG CCG               254
Ala Leu Gly Leu Arg Asp Glu Pro Gln Gly Ala Pro Arg Leu Arg Pro
             45              50                      55

GTT CCC CCG GTC ATG TGG CGC CTG TTT CGA CGC CGG GAC CCC CAG GAG               302
Val Pro Pro Val Met Trp Arg Leu Phe Arg Arg Arg Asp Pro Gln Glu
         60              65                  70

ACC AGG TCT GGC TCG CGG CGG ACG TCC CCA GGG GTC ACC CTG CAA CCG               350
Thr Arg Ser Gly Ser Arg Arg Thr Ser Pro Gly Val Thr Leu Gln Pro
     75              80                  85

TGC CAC GTG GAG GAG CTG GGG GTC GCC GGA AAC ATC GTG CGC CAC ATC               398
Cys His Val Glu Glu Leu Gly Val Ala Gly Asn Ile Val Arg His Ile
 90              95                 100                 105

CCG GAC CGC GGT GCG CCC ACC CGG GCC TCG GAG CCT GTC TCG GCC GCG               446
Pro Asp Arg Gly Ala Pro Thr Arg Ala Ser Glu Pro Val Ser Ala Ala
                110                 115                 120

GGG CAT TGC CCT GAG TGG ACA GTC GTC TTC GAC CTG TCG GCT GTG GAA               494
Gly His Cys Pro Glu Trp Thr Val Val Phe Asp Leu Ser Ala Val Glu
             125                 130                 135

CCC GCT GAG CGC CCG AGC CGG GCC CGC CTG GAG CTG CGT TTC GCG GCG               542
Pro Ala Glu Arg Pro Ser Arg Ala Arg Leu Glu Leu Arg Phe Ala Ala
         140                 145                 150

GCG GCG GCG GCA GCC CCG GAG GGC GGC TGG GAG CTG AGC GTG GCG CAA               590
Ala Ala Ala Ala Ala Pro Glu Gly Gly Trp Glu Leu Ser Val Ala Gln
     155                 160                 165

GCG GGC CAG GGC GCG GGC GCG GAC CCC GGG CCG GTG CTG CTC CGC CAG               638
Ala Gly Gln Gly Ala Gly Ala Asp Pro Gly Pro Val Leu Leu Arg Gln
170                 175                 180                 185

TTG GTG CCC GCC CTG GGG CCG CCA GTG CGC GCG GAG CTG CTG GGC GCC               686
Leu Val Pro Ala Leu Gly Pro Pro Val Arg Ala Glu Leu Leu Gly Ala
                190                 195                 200

GCT TGG GCT CGC AAC GCC TCA TGG CCG CGC AGC CTC CGC CTG GCG CTG               734
Ala Trp Ala Arg Asn Ala Ser Trp Pro Arg Ser Leu Arg Leu Ala Leu
             205                 210                 215

GCG CTA CGC CCC CGG GCC CCT GCC GCC TGC GCG CGC CTG GCC GAG GCC               782
Ala Leu Arg Pro Arg Ala Pro Ala Ala Cys Ala Arg Leu Ala Glu Ala
         220                 225                 230

TCG CTG CTG CTG GTG ACC CTC GAC CCG CGC CTG TGC CAC CCC CTG GCC               830
Ser Leu Leu Leu Val Thr Leu Asp Pro Arg Leu Cys His Pro Leu Ala
     235                 240                 245

CGG CCG CGG CGC GAC GCC GAA CCC GTG TTG GGC GGC GGC CCC GGG GGC               878
Arg Pro Arg Arg Asp Ala Glu Pro Val Leu Gly Gly Gly Pro Gly Gly
250                 255                 260                 265
```

```
GCT  TGT  CGC  GCG  CGG  CGG  CTG  TAC  GTG  AGC  TTC  CGC  GAG  GTG  GGC  TGG       926
Ala  Cys  Arg  Ala  Arg  Arg  Leu  Tyr  Val  Ser  Phe  Arg  Glu  Val  Gly  Trp
               270                      275                          280

CAC  CGC  TGG  GTC  ATC  GCG  CCG  CGC  GGC  TTC  CTG  GCC  AAC  TAC  TGC  CAG       974
His  Arg  Trp  Val  Ile  Ala  Pro  Arg  Gly  Phe  Leu  Ala  Asn  Tyr  Cys  Gln
               285                      290                          295

GGT  CAG  TGC  GCG  CTG  CCC  GTC  GCG  CTG  TCG  GGG  TCC  GGG  GGG  CCG  CCG      1022
Gly  Gln  Cys  Ala  Leu  Pro  Val  Ala  Leu  Ser  Gly  Ser  Gly  Gly  Pro  Pro
               300                      305                          310

GCG  CTC  AAC  CAC  GCT  GTG  CTG  CGC  GCG  CTC  ATG  CAC  GCG  GCC  GCC  CCG      1070
Ala  Leu  Asn  His  Ala  Val  Leu  Arg  Ala  Leu  Met  His  Ala  Ala  Ala  Pro
               315                      320                          325

GGA  GCC  GCC  GAC  CTG  CCC  TGC  TGC  GTG  CCC  GCG  CGC  CTG  TCG  CCC  ATC      1118
Gly  Ala  Ala  Asp  Leu  Pro  Cys  Cys  Val  Pro  Ala  Arg  Leu  Ser  Pro  Ile
330                 335                      340                          345

TCC  GTG  CTC  TTC  TTT  GAC  AAC  AGC  GAC  AAC  GTG  GTG  CTG  CGG  CAG  TAT      1166
Ser  Val  Leu  Phe  Phe  Asp  Asn  Ser  Asp  Asn  Val  Val  Leu  Arg  Gln  Tyr
               350                      355                          360

GAG  GAC  ATG  GTG  GTG  GAC  GAG  TGC  GGC  TGC  CGC  TAACCCGGGG  CGGGCAGGGA       1219
Glu  Asp  Met  Val  Val  Asp  Glu  Cys  Gly  Cys  Arg
               365                      370

CCCGGGCCCA  ACAATAAATG  CCGCGTGG                                                    1247
```

( 2 ) INFORMATION FOR SEQ ID NO:33:

( i ) SEQUENCE CHARACTERISTICS:
        ( A ) LENGTH: 372 amino acids
        ( B ) TYPE: amino acid
        ( D ) TOPOLOGY: linear ( i i ) MOLECULE TYPE: protein ( x i ) SEQUENCE DESCRIPTION: SEQ ID NO:33:

```
Met  Pro  Pro  Pro  Gln  Gln  Gly  Pro  Cys  Gly  His  His  Leu  Leu  Leu  Leu
 1                    5                   10                       15

Leu  Ala  Leu  Leu  Leu  Pro  Ser  Leu  Pro  Leu  Thr  Arg  Ala  Pro  Val  Pro
               20                        25                       30

Pro  Gly  Pro  Ala  Ala  Ala  Leu  Leu  Gln  Ala  Leu  Gly  Leu  Arg  Asp  Glu
               35                        40                       45

Pro  Gln  Gly  Ala  Pro  Arg  Leu  Arg  Pro  Val  Pro  Pro  Val  Met  Trp  Arg
      50                        55                        60

Leu  Phe  Arg  Arg  Arg  Asp  Pro  Gln  Glu  Thr  Arg  Ser  Gly  Ser  Arg  Arg
 65                        70                        75                    80

Thr  Ser  Pro  Gly  Val  Thr  Leu  Gln  Pro  Cys  His  Val  Glu  Glu  Leu  Gly
               85                        90                       95

Val  Ala  Gly  Asn  Ile  Val  Arg  His  Ile  Pro  Asp  Arg  Gly  Ala  Pro  Thr
              100                       105                      110

Arg  Ala  Ser  Glu  Pro  Val  Ser  Ala  Ala  Gly  His  Cys  Pro  Glu  Trp  Thr
              115                       120                      125

Val  Val  Phe  Asp  Leu  Ser  Ala  Val  Glu  Pro  Ala  Glu  Arg  Pro  Ser  Arg
              130                       135                      140

Ala  Arg  Leu  Glu  Leu  Arg  Phe  Ala  Ala  Ala  Ala  Ala  Ala  Ala  Pro  Glu
145                       150                       155                      160

Gly  Gly  Trp  Glu  Leu  Ser  Val  Ala  Gln  Ala  Gly  Gln  Gly  Ala  Gly  Ala
                    165                       170                      175

Asp  Pro  Gly  Pro  Val  Leu  Leu  Arg  Gln  Leu  Val  Pro  Ala  Leu  Gly  Pro
              180                       185                      190

Pro  Val  Arg  Ala  Glu  Leu  Leu  Gly  Ala  Ala  Trp  Ala  Arg  Asn  Ala  Ser
```

-continued

|  |  |  | 195 |  |  |  | 200 |  |  |  | 205 |  |  |  |
|---|---|---|---|---|---|---|---|---|---|---|---|---|---|---|
| Trp | Pro 210 | Arg | Ser | Leu | Arg | Leu 215 | Ala | Leu | Ala | Leu | Arg 220 | Pro | Arg | Ala | Pro |
| Ala 225 | Ala | Cys | Ala | Arg | Leu 230 | Ala | Glu | Ala | Ser | Leu 235 | Leu | Leu | Val | Thr | Leu 240 |
| Asp | Pro | Arg | Leu | Cys 245 | His | Pro | Leu | Ala | Arg 250 | Pro | Arg | Arg | Asp | Ala 255 | Glu |
| Pro | Val | Leu | Gly 260 | Gly | Gly | Pro | Gly | Gly 265 | Ala | Cys | Arg | Ala | Arg 270 | Arg | Leu |
| Tyr | Val | Ser 275 | Phe | Arg | Glu | Val | Gly 280 | Trp | His | Arg | Trp | Val 285 | Ile | Ala | Pro |
| Arg | Gly 290 | Phe | Leu | Ala | Asn | Tyr 295 | Cys | Gln | Gly | Gln | Cys 300 | Ala | Leu | Pro | Val |
| Ala 305 | Leu | Ser | Gly | Ser | Gly 310 | Gly | Pro | Pro | Ala | Leu 315 | Asn | His | Ala | Val | Leu 320 |
| Arg | Ala | Leu | Met | His 325 | Ala | Ala | Ala | Pro | Gly 330 | Ala | Ala | Asp | Leu | Pro 335 | Cys |
| Cys | Val | Pro | Ala 340 | Arg | Leu | Ser | Pro | Ile 345 | Ser | Val | Leu | Phe | Phe 350 | Asp | Asn |
| Ser | Asp | Asn 355 | Val | Val | Leu | Arg | Gln 360 | Tyr | Glu | Asp | Met | Val 365 | Val | Asp | Glu |
| Cys | Gly 370 | Cys | Arg |  |  |  |  |  |  |  |  |  |  |  |  |

What is claimed is:

1. A method for inducing regeneration of lost or damaged hepatic tissue in a mammal, the method comprising the step of:
administering a morphogen to a locus of said damaged or lost tissue under conditions such that said morphogen induces tissue-specific regeneration thereat,
said morphogen comprising a dimeric protein having the following properties:
inducing a cascade of tissue-specific morphogenesis culminating in the formation of mammalian bone or liver tissue, and
comprising a pair of folded polypeptides, the amino acid sequence of each of which comprises a sequence sharing at least 70% amino acid sequence homology with the C-terminal seven-cysteine domain of human OP-1, residues 38–139 of Seq. ID No. 5.

2. The method of claim 1 wherein said morphogen is absorbed on a biocompatible, acellular matrix and administered locally to said locus.

3. The method of claim 2 wherein said matrix has components specific for hepatic tissue.

4. The method of claim 2 wherein said matrix is biodegradable.

5. The method of claim 2 wherein said matrix is derived from hepatic tissue.

6. The method of claim 2 wherein said matrix comprises liver specific collagen and liver specific cell attachment factors.

7. The method of claim 2 wherein said matrix comprises a synthetic polymeric material.

8. The method of claim 7 wherein said polymeric material comprises polylactic acid, polybutyric acid, polyglycolic acid, polyanhydride, or copolymers thereof.

9. The method of claim 2 wherein said matrix comprises pores of a dimension sufficient to permit the influx, differentiation and proliferation of migratory progenitor cells from the body of said mammal.

10. The method of claim 1 wherein the amino acid sequences of said morphogen polypeptides comprise an amino acid sequence sharing at least 80% homology with said C-terminal seven-cysteine domain of human OP-1.

11. The method of claim 10 wherein greater than 60% of the amino acid residues within said amino acid sequence sharing at least 80% homology with said domain of human OP-1 are identical to the corresponding aligned residues of said domain of human OP-1.

12. The method of claim 11 wherein greater than 65% of the amino acid residues within said amino acid sequence sharing at least 80% homology with said domain of human OP-1 are identical to the corresponding aligned residues of said domain of human OP-1.

13. The method of claim 12 wherein each of the amino acid residues within said amino acid sequence of at least one of said morphogen polypeptides is identical to, or is a conservative substution of, the corresponding aligned residue of said domain of human OP-1.

14. The method of claim 1 wherein said morphogen polypeptides are associated with morphogen prodomain polypeptides.

15. The method of claim 14 wherein the amino acid sequences of said morphogen prodomain polypeptides comprise residues 30–292 of Seq ID No. 17.

16. A method for inducing regeneration of lost or damaged hepatic tissue in a mammal, the method comprising the step of:
administering a morphogen to a locus of said damaged or lost tissue under conditions such that said morphogen induces tissue-specific regeneration thereat,
said morphogen comprising a dimeric protein having the following properties:
inducing a cascade of tissue-specific morphogenesis culminating in the formation of mammalian bone or liver tissue, and comprising a pair of polypeptides, the amino acid sequence of each of which comprises a sequence defined by Generic Sequence 6, Seq. ID No. 31.

17. The method of claim 16 wherein said sequences of said pair of morphogen polypeptides are defined by OPX, Seq. ID No. 29.

18. The method of claim 1 or 16 wherein said morphogen is obtained from milk, serum or culture supernatant of morphogen-secreting mammalian cells.

19. The method of claim 1 or 16 wherein the amino acid sequences of both of said morphogen polypeptides comprise a sequence selected from the sequences of the group consisting of C-terminal seven-cysteine domains of human OP-1, mouse OP-1, human OP-2, mouse OP-2, DPP, Vgl, Vgr-1, CBMP2A, CBMP2B, BMP3, GDF-1, 60A, BMP5 or BMP6 (Seq. ID Nos. 5 (residues 38–139), 6 (residues 38–139), 7 (residues 38–139), 8 (residues 38–139), 9, 10, 11, 12, 13, 14, 25 (residues 354–455), 26, 27 and 28, respectively); or, conservative substitution variants of any of said sequences, provided that any said conservative substitution variant, when dimerized, induces a cascade of tissue-specific morphogenesis culminating in the formation of mammalian bone or liver tissue.

* * * * *